(12) United States Patent
Alderete

(10) Patent No.: US 10,677,798 B2
(45) Date of Patent: *Jun. 9, 2020

(54) STRINGS OF EPITOPES USEFUL IN DIAGNOSING AND ELICITING IMMUNE RESPONSES TO SEXUALLY TRANSMITTED INFECTIONS

(71) Applicant: WASHINGTON STATE UNIVERSITY, Pullman, WA (US)

(72) Inventor: John F. Alderete, Moscow, ID (US)

(73) Assignee: Washington State University, Pullman, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/194,589

(22) Filed: Nov. 19, 2018

(65) Prior Publication Data

US 2019/0154689 A1 May 23, 2019

Related U.S. Application Data

(60) Provisional application No. 62/589,992, filed on Nov. 22, 2017, provisional application No. 62/673,557, filed on May 18, 2018.

(51) Int. Cl.
| | | |
|---|---|---|
| *A61K 39/00* | (2006.01) | |
| *A61K 38/00* | (2006.01) | |
| *C12Q 1/689* | (2018.01) | |
| *C07H 21/00* | (2006.01) | |
| *A61K 49/08* | (2006.01) | |
| *G01N 33/571* | (2006.01) | |
| *C07K 14/44* | (2006.01) | |

(52) U.S. Cl.
CPC .......... *G01N 33/571* (2013.01); *C07K 14/44* (2013.01); *G01N 2333/20* (2013.01); *G01N 2333/22* (2013.01); *G01N 2333/44* (2013.01)

(58) Field of Classification Search
CPC ........ C12Q 1/689; A61K 38/00; A61K 39/00; A61K 49/085; C07H 21/00
See application file for complete search history.

(56) References Cited

U.S. PATENT DOCUMENTS

| 7,514,230 B2 | 4/2009 | Weart et al. | |
|---|---|---|---|
| 8,017,103 B2 * | 9/2011 | Alderete | G01N 33/56905 424/269.1 |
| 9,910,042 B2 * | 3/2018 | Alderete | G01N 33/571 |
| 10,386,369 B2 * | 8/2019 | Alderete | C07K 14/44 |
| 2004/0136908 A1 | 7/2004 | Olson et al. | |
| 2007/0009974 A1 * | 1/2007 | Alderete | G01N 33/56905 435/7.32 |

FOREIGN PATENT DOCUMENTS

| WO | 2009085216 A2 | 7/2009 |
|---|---|---|
| WO | 2012092934 A1 | 7/2012 |

OTHER PUBLICATIONS

Alderete et al, ImmunoTargets and Therapy, 2013; 2: 91-10 (Year: 2013).*

* cited by examiner

*Primary Examiner* — Gary B Nickol
*Assistant Examiner* — Lakia J Jackson-Tongue
(74) *Attorney, Agent, or Firm* — W & C IP

(57) ABSTRACT

Methods and compositions for detecting and diagnosing sexually transmitted infections using a string of epitopes (SOE) specific for detection of causative microorganisms are provided. The antigenic epitopes may be single epitope sequences, a plurality of epitope sequences joined by amino acid linkers to form a series of epitopes (SOE), or nucleotide sequences encoding one or more SOEs and host cells harboring said SOE nucleotide sequences. SOEs specific for highly immunogenic regions of proteins from *Trichomonas*, *Treponema* and *Neisseria* species are provided. SOEs to detect the presence of *Trichomonas* species comprise regions from *Trichomonas* aldolase, GAPDH, α-enolase and α-actinin proteins. Pharmaceutical compositions comprising SOEs can also be used as vaccines or to elicit an immune response to specific microorganisms.

9 Claims, 24 Drawing Sheets

Specification includes a Sequence Listing.

Trichomonas vaginalis fructose-1-6-biphosphate aldolase
Acc# AAK73099

```
                                                                              A-W1                  60
Tv         MAVSYK---S  LGLV-  -NSK  DIFAKAVNGG  Y-AIPGYNFS  NLEQLQAIT ASVK TESPVI
Tp         MT-SYK---A  LGLV-  -NTK  DLFAKAVKGG  Y-AIPAYNFN  NLEQLQAIIQ     ACVETRSPVI
Ng         MA-------   --LV-  -SMR  QLLDHAAENS  Y-GLPAFNVN  NLEQMRAIME     AADQVNAPVI
Spy        MA-------   --IV-  -SAE  KFVQAAREAG  Y-AVGGFNTN  NLEWTQAILR     AAEAKQAPVL
Spn        MA-------   --IV-  -SAE  KFVQAARDNG  Y-AVGGFNTN  NLEWTQAILR     AAEAKKAPVL
Sa         MA-------   --LV-  -SMK  EMLIDAKENG  Y-AVGQYNIN  NLEFTQAILE     ASQEEKAPVI
Ec         MP-------   ---LV- -SMK  YLLQDAQANG  Y-AVPAFNIH  NAETIQAILE     VCSEMRSPVI
Ca         MAPPAVLS-K  SGVIYGKDVK  DLFDYAQEKG   F-AIPAINVT  SSSTVVAALE     AARDNKAPI-
Sc         MGVEQILKRK  TGVIVGEDVH  NLFTYAKEHK   F-AIPAINVT  SSSTAVAALE     AARDSKSPII
Hs         MIFCSTCN--  -NTQ        RTALLRNLG    FTAIPLHGQM  SQSKRLGSLN     KFKAKARSIL
Consensus  MA-------   --LV----   STK          DLFQXARENG  Y-AIPAFNVN     NLEXTQAILE     AAXXKKAPVI A-M1          A-W2            80                          100                    A-W3                 120
Tv         LQV SAGARKY -ANQTMLRY --------  MAQGAAE FAKEIHPEHK  L--   IPIVLHL DHGDS -----  101
Tp         LQVSSGARKY -ANATLLRN- --------  MARGAVE YAHELGVD--  ---   IPIVLHL DHGDS-  ----  97
Ng         VQASAGARKY -AGAPFLRH- --------  LILAAVE EFP           H--   IPVVMHQ DHGAS-  ----  87
Spy        IQTSMGAAKY MGGYKVCQT- --------  LITNLVE SM-  -----    GI    VPVAIHL DHGH-   ----  88
Spn        IQTSMGAAKY MGGYKVARN- --------  LIANLVE SM-  -----    GI    VPVAIHL DHGH-   ----  88
Sa         LGVSEGAARY MSGFYTIVK- --------  MVEGLM- -HDLNIT-     --    IPVAIHL DHGSS-  ----  89
Ec         LAGTPGTFKH IALEEIYAL- --------  -CSAYSTT Y---           --    MPLALHL DHHES-  ----  86
Ca         LQTSQGGAAY FAGKGVDNKD QAASIAGSIA AAHYIRAIAP         TYGI PVVLHT DHCAKKLLPW     118
Sc         LQTSNGGAAY FAGKGISNEG QNASIKGAIA AAHYIRSIAP         AYGI PVVLHS DHCAKKLLPW     119
Hs         LATDVASRGL ---------- --------  -A------  -         -DIP---HV  D-----      67
Consensus  LQTSXGAAKY -AGXXVLRX- --------  -XIAGAVE  -A------  T---  IPVVLHL DHGAS------

140                                     160                      ALD12         180
Tv         FELCKSCIDL  GF--------  SSVMIDGSHH   P-------YD  ENVALTKKVV     EYAHS RPDYV
Tp         LELCIDCIES  GF--------  SSVMIDGSAL   P-------YD  ENVALSRKVC     EYAHARADYV
Ng         PDVCQRSIQL  GF--------  SSVMMDGSLL   EDGKTPSSYE  YNVNATRTVV     NFSHACG--V
Spy        YEDALECIEV  GY--------  TSIMFDGSHL   P-------VE  ENLAKTAEVV     KIAHAKG--V
Spn        YEDALECIEV  GY--------  TSIMFDGSHL   P-------VE  ENLKLAKDVV     EKAHAKG--I
Sa         FEKCKEAIDA  GF--------  TSVMIDASHS   P-------FE  ENVATTKKVV     EYAHEKG--V
Ec         LDDIRRKVHA  GV--------  RSAMIDGSHF   P-------FD  ENVKLVKSVV     DFCHSQD--C
Ca         FDGMLKADEE  FFAKTGTPLF  SSHMLDLSEE   TD------D   ENIATCAKYF     ERMAKMGQW-
Sc         FDGMLEADEA  YFKEHGEPLF  SSHMLDLSEE   TD------E   ENISTCVKYF     KRMAAMDQW-
Hs         ----------  ----------  --VVV-----   --------    -NFDIPTHSK     DYIHRVGR--
Consensus  FEDCLECIEA  GF--------  SSVMIDGSHL   P-------YE  ENVALTKKVV     EYAHAKG--V
```

```
                    380 A-W7/A-M3      A-W8           400                    420
Tv   ----------------  --HPDWFDPR QYLGEARTKL TEMYMRKDQE VLGCAGHA-- --------- --------
Tp   ----------------  --KVDEFDPR KYLGPARDEL KKLYMHKNKE VLGSAGRA-- --------- --------
Ng   ----------------  --NPSDFDPR KYLGKTIEAM KQICLDRYL- AFGCEGQAGK --------- --------
Spy  ----EANEAE------  YDGKKLFDPR KFLAPGMKAV QGAVEERI-D VFGSANKA-- --------- --------
Spn  ----EANEAE------  YDKKKLFDPR KFLADGVKAI QASVEERI-D VFGSEGKA-- --------- --------
Sa   ----------------  --DKEVYDPR KYLGPAREAI KETVKGKIKE -FGTSNRA-- --------- --------
Ec   ----------------  --NPQGNDPR YYMRVGMDAM KEVVRNKIN- VCGSANRNSA --------- --------
Ca   ---APVGNPEGAD---  KPNKKYFDPR VWVREGEKTM SKRIAEAL-D IFHTKGQL-- --------- --------
Sc   ---SPVGNPEGPE---  KPNKKFFDPR VWVREGEKTM GAKITKSL-E TFRTTNTL-- --------- --------
Hs   ----------------  ---DTE GAIGVRNKVA GGKMKKR--- ----KGR--- --------- --------
                      --NKKLFDPR KYLGXGRKAM KEKVXEXI-E VFGSAGRA-- IKPVSLEKMA

Tv   ---------------- ---------- FD 328
Tp   ---------------- ---------- -- 332
Ng   -SRYAKGELNQ----- ---------- IVK 354
Spy  ---------------- ---------- --- 293
Spn  ---------------- ---------- --K 293
Sa   ---------------- ---------- --- 286
Ec   ---------------- ---------- --- 286
Ca   ---------------- ---------- --- 359
Sc   ---------------- ---------- --- 359
Hs   ---------------- ---------- --- 189
```

FIG. 3C

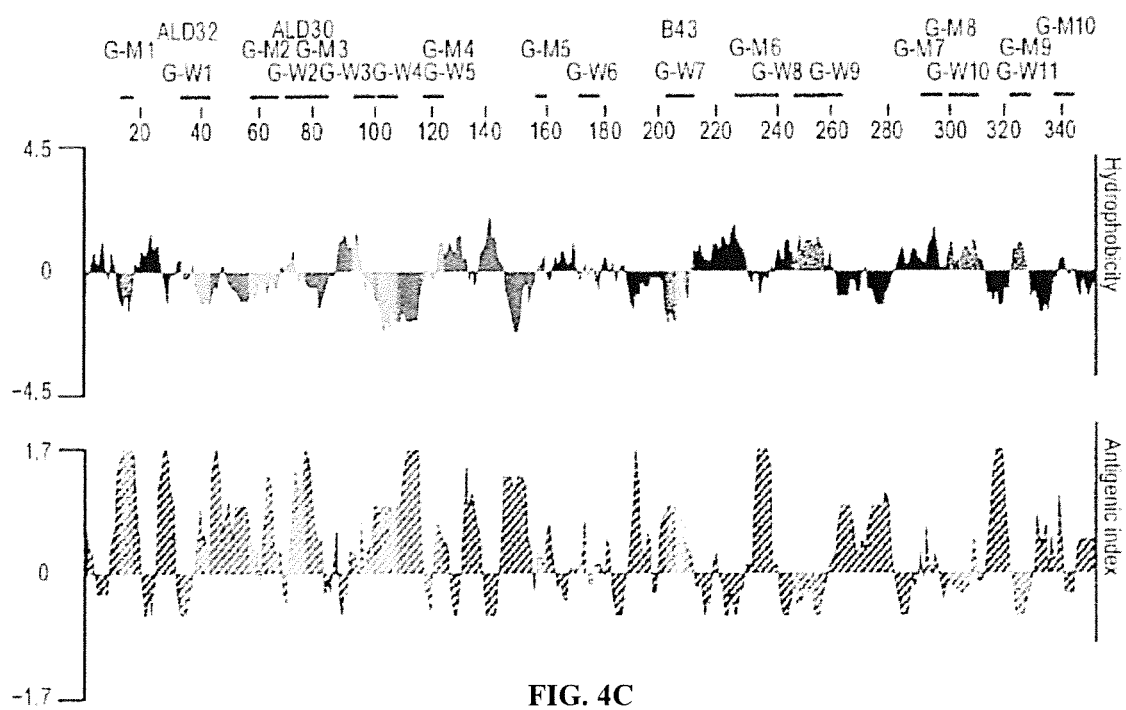
FIG. 4C
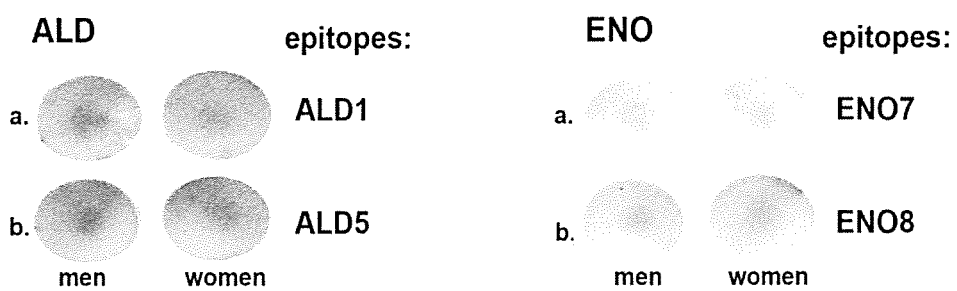
FIG. 5A
FIG. 5B
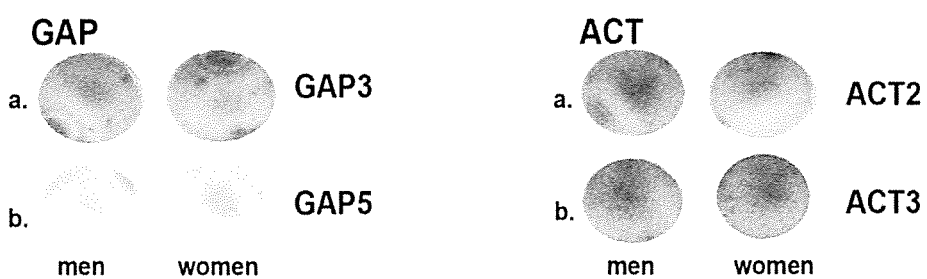
FIG. 5C
FIG. 5D

SEQ ID NO: 145

111 amino acid sequence of 13.35-kDa recombinant SOP protein encoding epitopes

GAP2      GAP3      ENO6

MKK-QEFTVGEGADKWVVK-KK-WVVKSIGGRLGPSQL-KK-SSEFYDEEKKLYEVE-KK-

ENO7      ALD4      ALD5

DYENWTKLNARLGQR-KK-HTYTRPEEVQDFVSK-KK-SSSIPQEYVEMVNKY-KK-HHHHHH

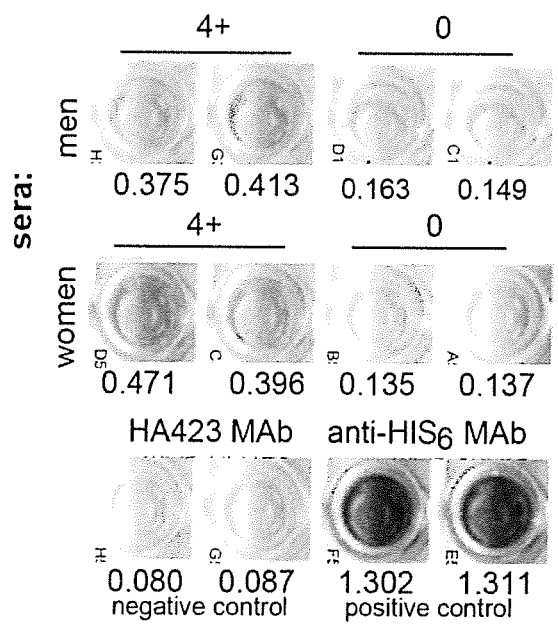
FIG. 8A
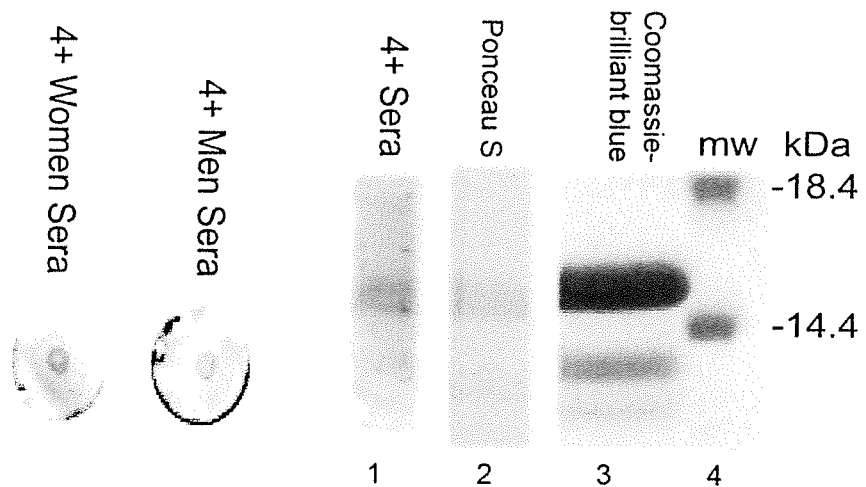
FIG. 8B
FIG. 8C

Recombinant SOP protein encoding sequential epitopes of the α-actinin protein of *T. vaginalis* immunoreactive with women and men seropositive sera as a diagnostic target.

```
        ACT1                    ACT2                    ACT3
GG-SVRREGLLDDAWEKT-GG-LARQIQFETIETDFE-GG-PSKWHKQPKMMVQKR-

ACT4                    ACT5                    ACT6
GG-QGYEHVAVNNFTTSW-GG-GIYVYLDPEDVIDTT-GG-KIAAMADKIKRTVAI-

ACT7                    ACT8                    ACT9
GG-IPGIRGKLASVISYN-GG-CKSGNRPIPEIPQGL-GG-SVNRHHSQLITYIKH-

ACT10                   ACT11                   ACT12
GG-AQPLYDEAIAFKEEV-GG-ELVEFKLNYKVTYTY-GG-EFKLNYKVTYTYSDA-

ACT13
GG-FKDTFKYFDKDKSNS-GG-HHHHHH
``` general informaton: 229 amino acids
25,198.23 daltons

SEQ ID NO: 146

FIG. 9

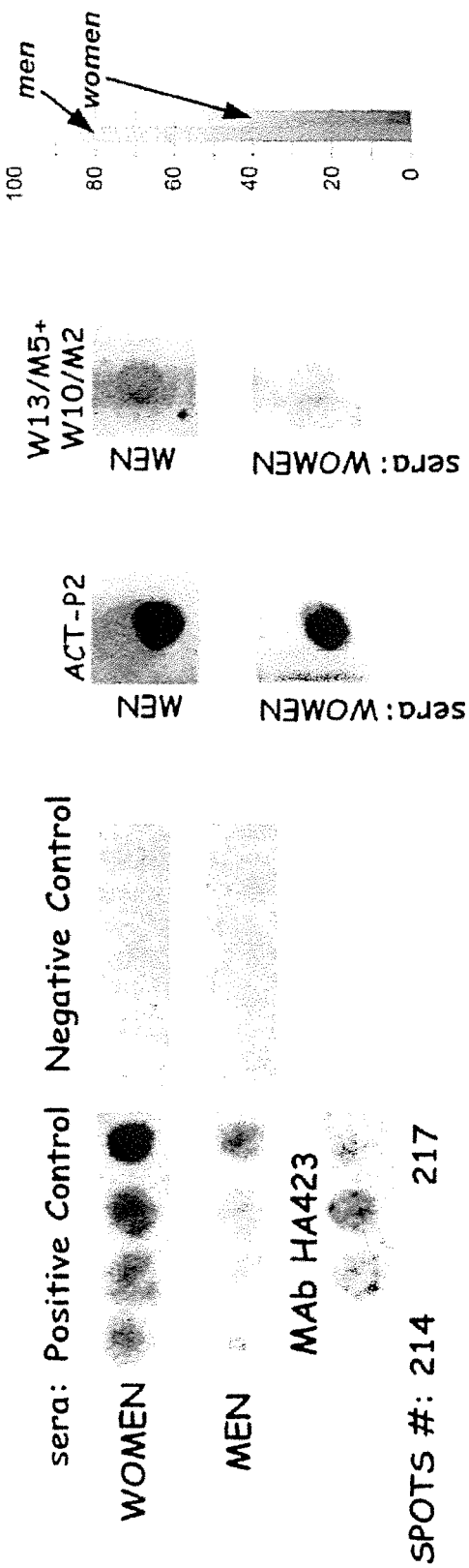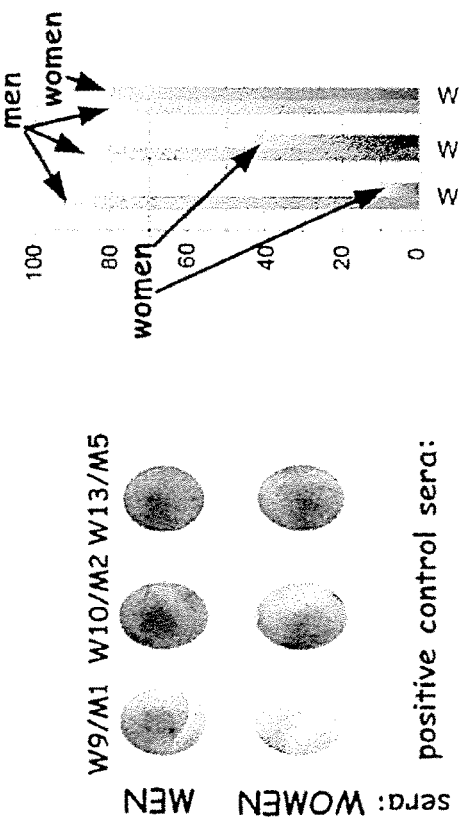
FIG. 12A
FIG. 12B
640-NELVEFKLNYK SEQ ID NO:162
VEFKLNYKVTY SEQ ID NO:163
KLNYKVTYTYS SEQ ID NO:164
YKVTYTYSDAT-659 SEQ ID NO:165
FIG. 12C
FIG. 12D
FIG. 12E
FIG. 12F
FIG. 12G

```
                                    W1                              20                        40
Trichomonas vaginalis      MSV RREG.... .............. ............LLDDAW-EKT  Q-IKVFSRWV- -QKQLLARQI
     Tritrichomonas suis   VKDR-.... .............. ............NDE           QRRARFEKY- .........
       Candida albicans    MFQKQK-... .............V SPWEYLQEAT LVK--WVNTK    LIEDTLSPQT PTSSCKNISE
Saccharomyces cerevisiae   MNIVKLQVRK FPILTQEDLF STIEKFRAID LDDKGWVEKQ         QALEAVSKDG -DATYDEARE
            Homo sapiens   MNQIEPGVQY NYVYDEDEYM IQEEEWDRDL LDDPAW-EKQ         Q-RKTFTAWC -NSHLRKAGT
               Consensus   MNQRXXG--- ---------- S---E----- LLD-AW-EKQ         Q-RKTFSKWX -XSXLXXAXE W2                        80                      100                 120
Trichomonas vaginalis      QFETIETDFE DGTKLLNLLE II........ ........GKE PMPSKWH KQP  KMMVQKRENV   79
     Tritrichomonas suis   -YSQLDKDGS GHLNYEEFFKK FL........ ........... .........  -VTYNKKEMP   46
       Candida albicans    TINNLTSDLH DSLVLTKLVN RLIYEVTLNP DHPMNKKANL YYLTPIYTKP   TFKLQKLENL  105
Saccharomyces cerevisiae   TLKHVGVDAS GRVELDDYVG LV-------- .....AKL R-ESKTGAAP   QTTFNVAPNS  103
            Homo sapiens   QIENIEEDFR NGLKLMLLLE VI-------- .....SGE RLPKP-.DRG   KMRFHKIANV  100
               Consensus   XIENXEXDFS XGLKLXXLXE XX-------- -----AKX R-PSX--XXP   KMTFXKKENV  100

140                    160                       180
Trichomonas vaginalis      DLALKYINEV KKIRTVG-IG ADDIINKNLK LTLGLTWTCI NKFMIEEISV EEATA-....
     Tritrichomonas suis   EKQYEFFFRG ADIDAGGSIG KEELF..... LTLGLVWSL- ----TL VEALYKNDQL
       Candida albicans    SDLLKFLNLI LSINVSS-IS PENIFDGDLK LTLGLVWSL- ----FIFNTASV FPGTPTYSGI
Saccharomyces cerevisiae   TPIVSTAATG LQHKGKG-TQ AKIIVAGS-- QTGTTHT-- -INEEER REFTK-....
            Homo sapiens   NKALDYIAS- KGVKLVS-IG AEEIVDGNVK MTLGMIWTII LRFAIQDISV EETSA-....
               Consensus   XKALKXIXXG XXIKXVG-IG AEEIXDGNLK LTLGLTWT-- --F-INEISV EEATA-....

200                    220                        240
Trichomonas vaginalis      RDALLLWAKK NTQG YEHVAV NNFTI--SWN TGLAFAALIN KFRPNL...L DYSALDYNDH  188
     Tritrichomonas suis   YINKLFFRAV DKDRSREIEA DEF....... --VVMAELNG REMSKEDAAA QIERLTGG-.  132
       Candida albicans    KTILLKWIN- --GILTDTSI RNFSKDWANE PETILCEIIS NYDANIPCGM NLSEL-....  213
Saccharomyces cerevisiae   HINSVLAGDQ DIGDLLPFPT DTFQLFDECR DGLVLSKLIN DSVPDT-..I DTRVLNW-PK  204
            Homo sapiens   KEGLLLWCOR KTAPYRNVNI QNFHT--SWK DGLGLCALIH RHRPDL-..I DYSKLNKDDP  208
               Consensus   KINLLLWXXX DTGXXRXVXI DNFXT--SWX DGLVLXXLIN RXRPXL---I DYSXLNX-D-
```

|  | 740 | | | 780 | |
|---|---|---|---|---|---|
| Trichomonas vaginalis | ELDQARLD-- | -LKQIILAKK | TFLEEEERKA | RINN----Y | TVKADEH--- | -MNEAHALDG |
| Tritrichomonas suis | DKDNSR--- | -------- | -------- | -------- | -------- | -------- |
| Candida albicans | NIDPIST-- | KLEQLITLDS | LILAE----- | -------- | -------- | --ISE |
| Sacchararomyces cerevisiae | EISRFKA--- | ------LEN | TNYAVDLGRA | K-------- | -------- | ---GF |
| Homo sapiens | TMDELRTKWD | KVKQLVPIRD | QSLQEELARQ | HANERLRRQF | AAQANAIGPW | IQNKMEEIAR |
| Consensus | EIDXXRT--- | -LKQLI-LXX | TXLAEEL-RA | -------- | -------- | ----IXX |

|  | 800 | | | 840 | | |
|---|---|---|---|---|---|---|
| Trichomonas vaginalis | KINSVDGE-L | EPKRQKLYEV | REEV-NAKK- | -EKAAEELTP | IYEDLEKDQL | HLEITSTPAS 764 |
| Tritrichomonas suis | -------- | -------- | -------- | -------- | -------- | -------- 280 |
| Candida albicans | VILNTNSEEL | FIKLSKLKDV | K-------- | -------- | ------TK | HKSVKTECET 462 |
| Sacchararomyces cerevisiae | SLVGIEGS-D | IVDGNKLL- | -------- | -------- | -------- | ----T 510 |
| Homo sapiens | SSIQITGA-L | EDQMNQLKQY | EHNIINYKNN | IDKLEGDHQL | IQEALVFDNK | HTNYTME--H 719 |
| Consensus | SIXXIXGE-L | EXXXNKLK-V | -------- | -------- | -------K | H---T-E--T |

|  | 880 | | | 900 | | |
|---|---|---|---|---|---|---|
| Trichomonas vaginalis | INIFFENLIA | HIDTLVKEID | AAIAAAKGLE | ISEEELNEFK | DT[KYFDKQK | SNSLEYFELK |
| Tritrichomonas suis | -------- | --KVSVAEMK | DAVQNVMGKT | FTPEEFTA-- | -------- | -------- |
| Candida albicans | TIEYFLGFFR | KLEMFESSLQ | SS--PPLKY | FEARDPPDFD | ITPDIFNQFK | TVILRH--- |
| Sacchararomyces cerevisiae | LGLVWQLMRR | NISITMKTLS | SS-----GRD | MSDSQILKWA | QD-QVTKGGK | NSTIRSFKDQ |
| Homo sapiens | IRVGWELLLT | TIARTINEVE | TQILTRDAKG | ITQEQMNEFR | ASFNHFDRRK | NGLMDHEDFR |
| Consensus | IXXXXELLXR | XIXXTVKELX | SXI--XXGKX | XXXEXXNEFX | XTFXXFDXXK | NXXLRHF--- |

|  | 920 | | | 960 | | |
|---|---|---|---|---|---|---|
| Trichomonas vaginalis | ACLTALGEDI | TDGQAKEYCK | KYNSK----- | -GEGTALEFD | DYVRFMLDHF | SKAETTETTM 878 |
| Tritrichomonas suis | QCKLEFGANK | KELEFWEFYK | LITGET--- | --IDKATOPY | DGKLPAEKSK 350 |
| Candida albicans | NNCHHDKLFR | VLQEQFVPSD | FSNTTLEFFT | RLIPIKASPI | SSNDSSFDLT 565 |
| Sacchararomyces cerevisiae | A------L | SNAHF--LLD | VLNGI----- | -APG----- | -YVDY-DLV | TPGNTEEERY 599 |
| Homo sapiens | ACLISMGYDL | GEAEFARIMT | LVDPN---- | -GQGT-VTFQ | SFIDFMTRET | ADTDTAEQVI 832 |
| Consensus | ACL---G-DL | XXAXFXELXK | XLNGX---- | -GXGT----F- | -YIDFMTDPX | SXXDTAEXXX |

FIG. 14D

SEQ ID NO:175

```
        A (W4)              A (W8)           E (ALD13)        E (W1, ALD55)           73
EEHTYTRPEEVQDFVSKEELGEARTKLTEMYMRKEEAEHDAIVKECIAEAAEEVKYLGRVTLAARSSAEEVTL

E (M1)          E (W3/M3)           E (W4/M4)            E (W5)           E (M7)  147
AARSSAPSGASTEETDGTVLKKNIGGNASEEDKVPKKFKLPSPFFNEEKLGGLLVKKYGLSAKEEILVKKYGLS

E (M8)                 E (M9)           G (M1)           G (W1, ALD32)  220
AKNLDEFEEASSEFYDEEKKLYEVEEDYENWTKLNARLGQRVEERASRKLYPKDIQVVAEENVYLLKYDTAHR

G (M2)          G (W2, ALD30)        G (W3)                G (W4)         293
AFPEEQEFTVGEGADKWVVKEEWVVKSIGGRLGPSQLEEVVLESTGIFRTKAEKEEKDAEGKIKKDDGYDGHE

G (W6)              317
ETLNNAFGIRNGFMTTVHHHHHH
```

| MW 35896.31, pI 5.05, 8 MALE EPITOPES, 11 FEMALE EPITOPES, 4 MAb EPITOPEs |
|---|
| 2 Glutamic acid Linkers plus HHHHHH.     ALD13, 55, 32, 30 are MAbs. |

FIG. 15

|  | Condition According to Gold Standard α-actinin | | Total | |
|---|---|---|---|---|
| | Present | Absent | | |
| Diagnostic Test Result — Positive | a = True positives 54 | b = False positives 4 | a + b 58 | Predictive Value (+) $PPV = \frac{a}{a+b}$ 93% probability person has disease |
| Diagnostic Test Result — Negative | c = False negatives 5 | d = True negatives 21 | c + d 26 | Predictive Value (−) $NPV = \frac{d}{c+d}$ 81% probability person does not have |
| Total | a + c 59 | b + d 25 | | Grand Total a + b + c + d 84 |
| | Sensitivity $\frac{a}{a+c}$ 92% (with disease) | Specificity $\frac{d}{b+d}$ 84% (without disease) | | |

FIG. 18

| sera and antibodies | dilution | α-Actinin | AEG::SOE2 |
|---|---|---|---|
| secondary peroxidase-goat anti-human IgG | 1:1000 | 0.055, 0.056 | 0.052, 0.051 |
| pooled negative human sera | 1:25 | 0.105, 0.110 | 0.104, 0.107 |
| pooled positive human sera 1 | 1:25 | 0.510, 0.502 | 0.428, 0.470 |
| pooled positive human sera 2 | 1:25 | 0.364, 0.375 | 0.365, 0.375 |
| pooled positive human sera 3 | 1:25 | 0.490, 0.485 | 0.403, 0.428 |
| mouse anti-*Tv* serum | 1:100 | 0.388, 0.386 | 0.353, 0.350 |
| AEG MAb cocktail mix | 1:1:1:1 (v/v) | 0.056, 0.059 | 0.260, 0.250 |
| α-actinin MAb HA423 | none | 0.450, 0.425 | 0.060, 0.055 |
| MAb L64 negative control | none | 0.055, 0.055 | 0.051, 0.050 |

FIG. 19

STRINGS OF EPITOPES USEFUL IN DIAGNOSING AND ELICITING IMMUNE RESPONSES TO SEXUALLY TRANSMITTED INFECTIONS

FIELD OF THE INVENTION

The invention relates to compositions and methods used to detect and/or diagnose infections caused by, for example, *Trichomonas, Treponema*, and *Neisseria* species. The invention further relates to compositions and methods for eliciting an immune response and/or vaccinating against infection by *Trichomonas, Treponema*, and *Neisseria* species.

BACKGROUND OF THE INVENTION

Sexually transmitted infections (STIs) are a major global cause of acute illness, infertility, long term disability and death, with severe medical and psychological consequences for millions of men, women and infants. WHO estimated that 340 million new cases of syphilis, gonorrhoea, *Chlamydia* and trichomoniasis occurred throughout the world in 1999 in men and women aged 15-49 years, and incidence has risen steadily since then.

*Trichomonas vaginalis* causes vaginitis in women and non-gonococcal, non-chlamydial urethritis in men. Among men, the most recent findings indicate a relationship between seropositivity to *T. vaginalis* and prostate cancer. This parasite is now the number one, non-viral sexually transmitted disease agent. In 2013, the incidence of this sexually transmitted infection (STI) referred to as trichomonosis or trichomoniasis is estimated to be 10 million women in the United States and 270 to 350 million women worldwide. Health consequences to women include cervical cancer, pelvic inflammatory disease, infertility, increased HPV and herpes susceptibility, and adverse pregnancy outcomes accompanied with low-birth-weight infants. Significantly, 25% of HIV seroconversions are the direct result of trichomonosis, which is known to increase the portal of exit and entry of HIV infectious viral particles. Therefore, control of trichomonosis may be one of the most effective means of reducing HIV transmission risk and of preventing prostate and cervical cancers worldwide.

It is clear that the public health costs as a result of this STI are enormous, and interference strategies are needed. The most important interference strategy is the availability of rapid, accurate diagnostics with exceptional sensitivity and specificity toward this STI agent. Despite the impact of this STI to public health, fundamental aspects of *T. vaginalis* cell biology and mechanisms of pathogenesis remain unknown. As previously disclosed in U.S. Pat. No. 8,017,103 B2, incorporated by reference herein, α-actinin is expressed by *Trichomonas* species and can be used to detect the presence of *Trichomonas* infection. However, the antibodies to parasite proteins available hitherto are inferior in their ability to detect the immunoreactive trichomonad protein antigens.

SUMMARY OF THE INVENTION

The antibodies, proteins, and epitopes to the proteins detected by the human antibody described herein are novel and have increased utility for diagnostics to STIs. Antigenicity and specificity is increased with the microorganism-specific target protein antigens and epitopes described herein compared to previously available diagnostics. Furthermore, the present disclosure overcomes prior shortcomings in the art by providing epitopes for detecting antibody in sera of humans exposed to and/or infected with *T. vaginalis* and other microorganisms that cause STIs, such as *Treponema pallidum* and *Neisseria gonorrhoeae*. In addition to compositions and methods relating to detection and diagnosis of STIs, embodiments of the disclosure includes compositions and methods for eliciting an immune response and providing vaccines that can protect subjects from STIs.

An embodiment of the disclosure is a method of detecting the presence of a microorganism in a biological sample from a subject, comprising the steps of identifying at least one protein that is expressed by the microorganism of interest, determining regions of the protein that are highly immunogenic, and designing epitopes encoding those regions. In some embodiments, the epitopes are embedded within a 15-mer peptide. The disclosure is further directed to synthesizing a plurality of epitopes in a linear array to form a series of epitopes (SOE), wherein the epitopes are joined with amino acid linkers. In some embodiments, the linkers are a number of any amino acid residues. In some embodiments, the linkers are repeats of amino acid residues such as glycine (-GG-), lysine (-KK-), glutamic acid (-EE-), and mixtures thereof within the SOE. The SOE is then contacted with a biological sample under conditions whereby an antigen-antibody complex can form, and formation of at least one said antigen-antibody complex is an indication of the presence of the microorganism of interest. The SOE typically comprises at least six of said epitopes, but may comprise fewer or greater numbers of epitopes. A composition may comprise SOEs to detect multiple proteins from a single species or family of microorganisms, or from a group of unrelated microorganisms.

Sequences encoding epitopes and SOEs are provided to detect, diagnose or treat infections caused by *Trichomonas, Treponema*, and *Neisseria* species. Aspects of the disclosure are applicable to other species. Exemplary SOEs detect *Trichomonas* species including *Trichomonas* (T.) *vaginalis*, *T. vaginalis* isolates T016, T068-II, UT40, and VB102, *Tritrichomonas* (Tt.) *foetus, T. foetus, Tt enteris, T. paviovi, Tt. suis, Tt. rotunda, T. buttreyi, Tt. ovis, Tt. equi, T. equibuccalis, T. anatis, Tt. eberthi, T. gallinae, T. gallinarum, Tt. caviae, Tt muris, Tt. wenoni, Tt. Minuta, T. microti, T. canistomae, T. felistomae, T. tenax, Tt. hominis*, and *T. macacovaginae*. Epitopes, 15-mer epitopes and SOE sequences are provided to detect, diagnose, or treat infections caused by *Treponema pallidum* and *Neisseria gonorrhoeae*.

Additional bacterial pathogens may be detected, diagnosed, or vaccinated against, with SOEs encoding highly immunogenic regions of one or more proteins expressed by a microorganism or bacterial pathogen of interest. Other microorganisms include, but are not limited to *Chlamydia trachomatis, Saccharomyces cerevisiae, Candida albicans, Streptococcus pyogenes, Streptococcus pneumoniae*, and *Staphylococcus aureus*.

In one embodiment, detection is performed by immunoassay. A preferred immunoassay is an enzyme-linked immunosorbent assay (ELISA). The biological sample can be saliva, urine, blood, serum or plasma, a lung lavage or sputum sample, and the subject may be male or female. Biological samples can also be vaginal fluid or washing, or semen or prostatic fluid.

In some embodiments, the biological sample is cerebrospinal fluid, joint fluid, body cavity fluid, whole cells, cell extracts, tissue, biopsy material, aspirates, exudates, pap smear samples, pap smear preparations, slide preparations, fixed cells, and tissue sections. The biological samples can be collected from a subject that may be human, non-human primate, dog, cat, cattle, sheep, swine, horse, bird, mouse and rat.

In one exemplary embodiment, a method of diagnosing a *Trichomonas* infection in a subject comprises the steps of identifying at least one protein that is expressed by a *Trichomonas* species, determining one or more regions of at least one protein from *Trichomonas* that is/are highly immunogenic, designing epitopes encoding said regions of the protein, and synthesizing a plurality of epitopes in a linear array to form a series of epitopes (SOE) wherein the epitopes are joined with an amino acid linker. For example, any SOE may contain a mixture of two or more of -GG-, -KK-, and -EE- repeats. A biological sample from a subject is contacted with at least one SOE that binds an antibody to a *Trichomonas*-specific protein selected from the group consisting of aldolase, GAPDH, α-enolase and α-actinin, under conditions whereby an epitope-antibody complex can form, and detecting formation of at least one epitope-antibody complex as an indication of *Trichomonas* infection. The biological sample may be serum, plasma, blood, saliva, semen, cerebrospinal fluid, semen, prostatic fluid, urine, sputum, joint fluid, body cavity fluid, whole cells, cell extracts, tissue, biopsy material, aspirates, exudates, vaginal washings, pap smear samples, pap smear preparations, slide preparations, fixed cells, or tissue sections. The method of detecting the epitope-antibody may be performed using an immunoassay. In one exemplary embodiment, the immunoassay is an enzyme-linked immunosorbent assay (ELISA). The *Trichomonas* species that can be identified include *Trichomonas* (T.) *vaginalis*, *T. vaginalis* isolates T016, T068-II, UT40, and VB102, *Tritrichomonas* (Tt.) *foetus*, *T. foetus*, *Tt enteris*, *T. paviovi*, *Tt. suis*, *Tt. rotunda*, *T. buttreyi*, *Tt. ovis*, *Tt. equi*, *T. equibuccalis*, *T. anatis*, *Tt. eberthi*, *T. gallinae*, *T. gallinarum*, *Tt. caviae*, *Tt muris*, *Tt. wenoni*, *Tt. minuta*, *T. microti*, *T. canistomae*, *T. felistomae*, *T. tenax*, *Tt. hominis*, and *T. macacovaginae*. A subject may be any animal that can be infected by trichomonads. In certain embodiments, the subject is human.

An exemplary embodiment includes a method of diagnosing in a subject a sexually transmitted infection (STI) selected from the group consisting of trichomoniasis, gonorrohoeae, and syphilis. This embodiment involves the steps of identifying at least one protein that is expressed by the microorganism of interest, determining regions of at least one protein that is highly immunogenic, designing epitopes encoding the highly immunogenic regions of the protein, and synthesizing a plurality of said epitopes in a linear array to form a series of epitopes (SOE) wherein the 15-mer epitopes are joined with amino acid linkers. Variations on this method further comprise assaying biological samples from a subject that are collected at two or more different time points. The interval of time may be days, weeks, or months, as deemed appropriate by one of ordinary skill in the art of STI diagnosis. The assay can be an immunoassay, with at least one SOE encoding at least one protein specific to one or more microorganisms suspected of causing a STI, under conditions whereby an epitope-antibody or antigen-antibody complex can form; and detecting formation of at least one epitope-antibody complex in the two or more samples. Detection readout at the first time point is compared with detection readout of the second or later time point and the comparison is used to determine the status of a STI in said subject.

Embodiments of the invention include a monoclonal antibody that recognizes an epitope selected from the group of ALDwsu-1, ALDwsu-2, ALD12A, ALD64A, B44, ENOwsu-2, ENOwsu-3, ENOwsu-4, ENOwsu-6, B43, GAPwsu-2, GAPwsu-3, and HA423 (Tables 1 and 2A).

Embodiments also include an epitope selected from the group consisting of SEQ ID NO:1-53, 66-78, 104-106, 121-126, 139-143 and 162-174; or 15-mer epitope selected from the group consisting of SEQ ID NO:79-102, 107-119, and 128-133. The invention is further a string of epitopes (SOE), comprising a plurality of epitopes linked by an amino acid linker, selected from the group consisting of SEQ ID NO:120, 127, 134, 145, 146, and 175.

Embodiments further include a nucleic acid encoding at least one epitope, or at least one 15-mer epitope, or at least one string of epitopes (SOE), wherein the protein product of the nucleic acid binds to at least one antibody type in a biological sample and at least one antibody type is reactive with at least one *Trichomonas* protein selected from the group consisting of aldolase, alpha-enolase, GAPDH, and alpha-actinin.

Embodiments also include a host cell comprising a transgene encoding a string of epitopes (SOE), wherein the SOE comprises a plurality of epitopes selected from NO:1-53, 66-78, 104-106, 121-126, AND 139-143, or a plurality of 15-mer epitopes selected from the group consisting of SEQ ID NO:79-102, 107-119, AND 128-133, wherein each SOE binds to at least one antibody type in a biological sample and the antibody type is reactive with at least one protein from a microorganism of interest. For *Trichomonas*, the protein is selected from the group consisting of aldolase, alpha-enolase, GAPDH, and alpha-actinin.

In addition, embodiments include a kit for diagnosis of a sexually transmitted infection (STI) in a subject, comprising at least one string of epitopes (SOE) able to bind at least one antibody type in a biological sample that is reactive with at least one protein from a microorganism selected from the group consisting of *Trichomonas*, *Treponema*, and *Neiserria* species. The kit may comprise one or more reagents to perform an immunoassay of antibody-epitope or antibody-antigen complexes that form when the SOE of the kit contacts at least one antibody type in a biological sample, and may include a suitable vessel for performing said immunoassay, and a package insert describing steps required for performing said immunoassay, wherein detection of an antibody epitope or antibody-antigen complexes is diagnostic for a STI.

Embodiments also include eliciting an immune response to a microorganism in a subject. These involve identifying at least one protein that is expressed by the microorganism, determining regions of said at least one protein that are highly immunogenic, designing epitopes encoding said regions of said at least one protein, and synthesizing a plurality of said epitopes in a linear array to form a series of epitopes (SOE) wherein said epitopes are joined with amino acid linkers. A pharmaceutical composition preferably includes at least one SOE with a suitable carrier and adjuvant, which is administered to a subject in an amount sufficient to stimulate formation of antibodies to the SOE by the immune system of the subject.

BRIEF DESCRIPTION OF THE DRAWINGS

The following drawings are provided to assist in the understanding of the invention, but do not the limit the invention and its uses.

FIGS. 3A, 3B, and 3C show sequence alignment of fructose-1,6-bisphosphate aldolase sequences from *T. vaginalis* (SEQ ID NO:147), *T. pallidum* (SEQ ID NO:148), *N. gonorrhoeae* (SEQ ID NO:149), *S. pyogenes* (SEQ ID NO:150), *S. pneumoniae* (SEQ ID NO:151), *S. aureus* (SEQ ID NO:152), *E. coli* (SEQ ID NO:153), *C. albicans* (SEQ ID NO:154), *Saccharomyces cerevisiae* (SEQ ID NO:155) and *Homo sapiens* (SEQ ID NO:176).

FIG. 4C shows hydrophobicity and antigenicity profile of *T. vaginalis* α-glyceraldehyde-3-phosphate dehydrogenase (GAP).

FIGS. 5A, 5B, 5C, and 5D show representative dot blots of individual 15-mer peptide epitopes.

FIG. 8A shows immunodetection of rSOE by ELISA.

FIG. 8B shows immunodetection of rSOE by dot blot.

FIG. 8C shows immunodetection of rSOE by immunoblotting after SDS-PAGE.

FIG. 9 is an example of an SOE comprising thirteen epitopes detected by women and men exposed to *T. vaginalis* are arranged sequentially within individual 15-mer peptides separated by a diglycine. The sequence is that of SEQ ID NO:146.

FIGS. 12A-12G show SPOTs analysis with positive control sera from women and men, detecting overlapping peptides on SPOTs membranes of a representative epitope and reactions with immobilized ACT-P2 and synthetic 15-mer peptides used in combination or singly. 12A shows IgG antibody detection of overlapping peptides from spots 214-217. 12B shows the corresponding amino acid sequences of the individual oligopeptides (SEQ ID NO:162-165). 12C and 12D show signal intensities obtained for 1 microgram of ACT-P2 or 2/13M5+W10/M2 immobilized on nitrocellulose membranes and detected by IgG of positive control sera. 12E shows densitometric scans of the dots shown in C2 to provide relative intensities. 12F shows relative reaction of 1 µgram of 15-mer epitopes from Table 1, immobilized on nitrocellulose membranes. 12G shows denitometric scans to provide relative intensities of dots.

Figure 14B:
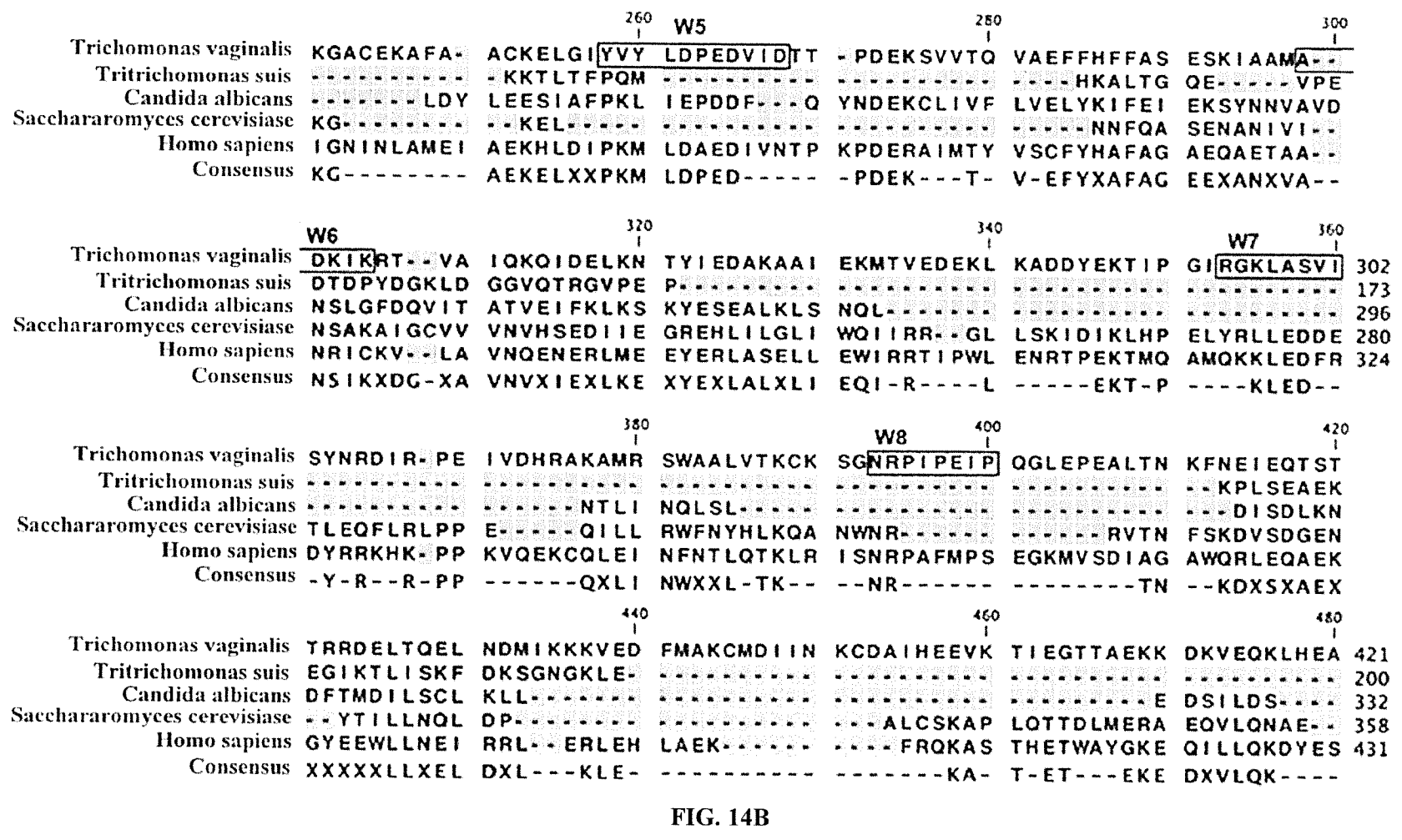
Figure 14C:
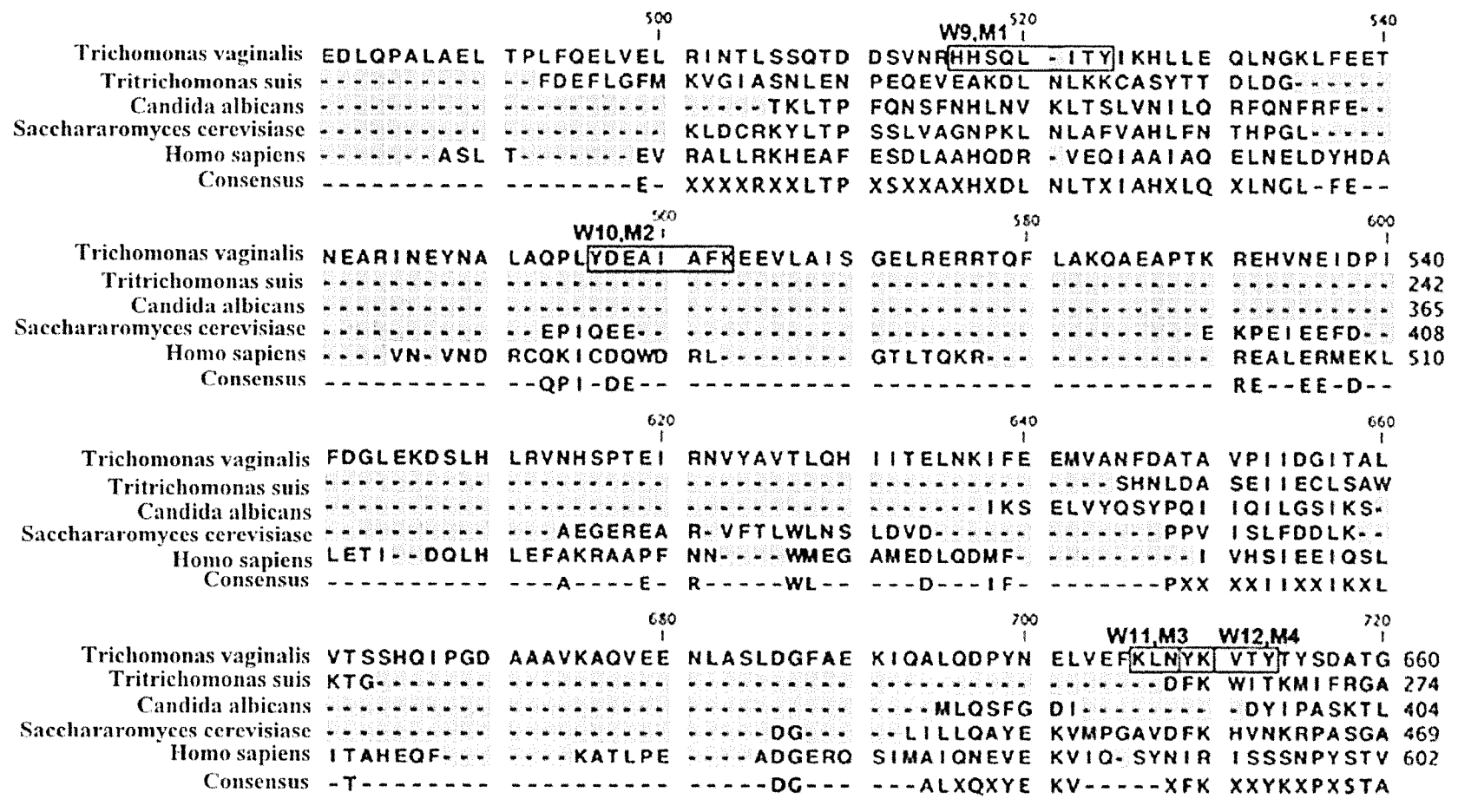

FIGS. 14A, 14B, 14C, and 14D show an amino acid sequence alignment of *T. vaginalis* α-actinin (SEQ ID NO:156) with representative pathogenic organisms *T. suis* (SEQ ID NO:177), *C. albicans* (SEQ ID NO:178), *S. cerevisiae* (SEQ ID NO:179) and HuACTN1 (SEQ ID NO:157).

FIG. 15 shows an SOE chimeric construct having 18 epitopes unique to *T. vaginalis* (SEQ ID NO:175).

FIG. 18 shows a classic 2×2 table for classifying individuals after testing.

FIG. 19 shows results of an ELISA comparing negative and positive women/men sera and mouse anti-Tv serum for detection of IgG antibody to AEG:SOE2 and ACT-P2 as targets.

DETAILED DESCRIPTION

Figure 1:
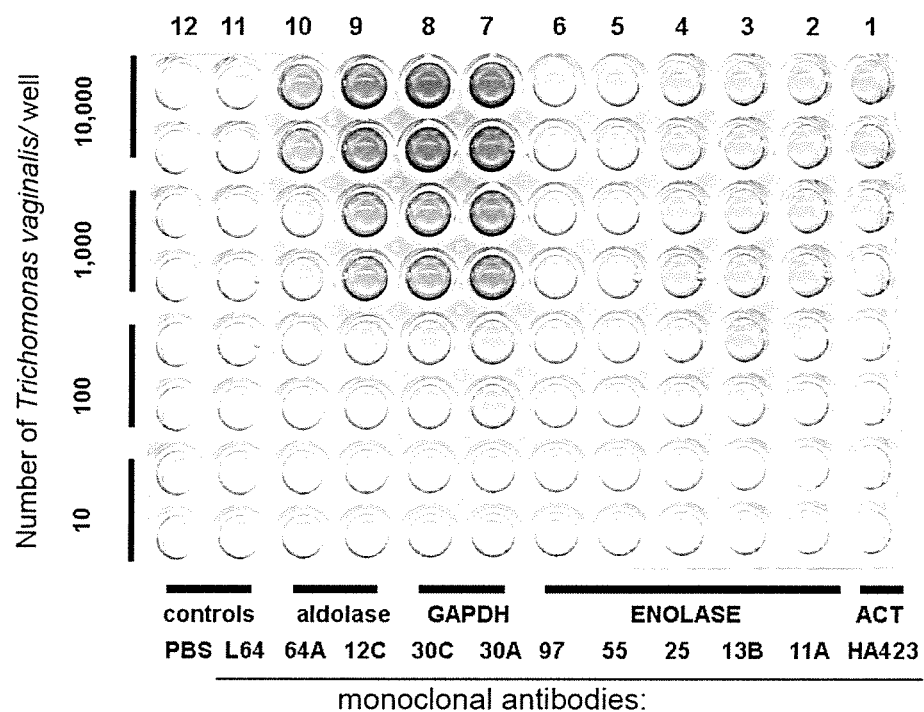
FIG. 1 shows an ELISA assay of trichomonads to detect *T. vaginalis* aldolase, GAPDH, and α-enolase.

The present disclosure provides peptide and nucleotide sequences encoding peptides that are highly immunogenic and may be used to detect the presence of microorganisms in a biological sample, or diagnose an infection of the microorganisms in a subject. The methods can comprise detection of one or more microorganism-specific proteins in one or more biological samples, or detection of antibodies that a subject has produced in response to exposure or infection caused by microorganisms. The disclosure further provides compositions and methods for eliciting an immune response in a subject, or vaccinating against a STI, such as trichomoniasis, gonorrhea or syphilis.

The disclosure further provides methods of arraying the highly immunogenic peptides in a linear macromolecule described herein as a series of epitopes (SOE), recombinant series of epitopes (rSOE), or string of pearls (SOP). In one embodiment, an SOE is synthetic DNA encoding a protein comprising sequential peptides. The DNA encoding the SOE can be ligated into a plasmid and used to transform or transfect a suitable host cell that will express the SOE as a recombinant protein. In another embodiment, an SOE can be synthesized as a polypeptide sequence encoding sequential peptides, such as 15-mer peptides. Amino acid linkers, such as repeats of glycine (-GG-), lysine (-KK-), or glutamic acid (-EE-) may be placed between the peptides, either encoded as nucleotides in DNA, or as amino acid residues in a synthetic polypeptide. In some embodiments, at least six epitopes linked with amino acid linkers are used, however, more epitopes may be added to a synthetic DNA construct or to a synthetic peptide. In another embodiment, several SOE species may be included in a composition. Each of the SOE species may differ in the identity of the epitopes included in each, or they may further be epitopes from different proteins or even different microorganisms.

The disclosure is based on the unexpected discovery that infection with *T. vaginalis* and other *Trichomonas* species can be diagnosed by detecting individually or in combination *T. vaginalis* or other *Trichomonas* species aldolase, GAPDH, α-enolase and/or α-actinin proteins or epitopes of the proteins either singly or in combination and/or antibodies to AGEA proteins or epitopes of the proteins either singly or in combination. Similar to embodiments relating to *T. vaginalis*, further embodiments of the disclosure are methods of detecting, diagnosing, treating, or preventing infection of *N. gonorrhoeae* and/or *T. pallidum*. These embodiments make use of highly immunogenic peptides, e.g. 15-mer peptides, and SOEs that elicit an immune response to either *N. gonorrohoeae* or *T. pallidum*, and sequence listings are provided for each of the microorganisms of interest. Each of the embodiments of the disclosure may be practiced by substituting the SOE or antibodies specific to a microorganism of interest, such as a species of the *Trichomonas, Neiserria* or *Treponema* families. Further, amino acid sequences of other sexually transmitted bacterial pathogens (*Chlamydia trachomatis*), of yeast (*Saccharomyces cerevisiae* and *Candida albicans*), and of other human bacterial pathogens (*Streptococcus pyogenes, Streptococcus pneumoniae*, and *Staphylococcus aureus*) may be identified and incorporated into SOEs for detection and diagnosis, and may also be used to elicit immune response and provide protection from infection.

Thus, in some embodiments, the present disclosure provides a method of diagnosing a *T. vaginalis* infection in a subject. Highly immunogenic regions of microorganism-specific proteins selected from the group consisting of *T. vaginalis* aldolase, GAPDH, α-enolase and/or α-actinin are identified and at least one SOE comprising peptides encoding the highly immunogenic regions. In some embodiments, the peptides are 15-mer peptides. In some embodiments, the peptides are linked with an amino acid linker such as with -GG-, -KK-, or -EE- amino acids. A biological sample from the subject suspected of having an infection caused by the *T. vaginalis* under conditions whereby an antigen/antibody complex can form; and b) detecting formation of an antigen/antibody complex, thereby detecting *T. vaginalis* AGEA proteins or epitopes of the proteins either singly or in combination in the sample and thereby diagnosing a *T. vaginalis* infection in the subject.

Additionally provided is a method of identifying an acute *T. vaginalis* infection in a subject, comprising: a) at a first time point, contacting a first sample from the subject with a *T. vaginalis* protein selected from a) aldolase, GAPDH, α-enolase and/or α-actinin proteins or epitopes of proteins either singly or in combination, under conditions whereby an antigen/antibody complex can form; b) detecting the formation of an antigen/antibody complex in step a); c) at a second time point, contacting a second sample from the subject with a *T. vaginalis* protein or epitopes of proteins selected from aldolase, GAPDH, α-enolase and/or α-actinin proteins, under conditions whereby an antigen/antibody complex can form; d) detecting the formation of an antigen/antibody complex in step (c); and e) comparing the amount of antigen/antibody complex of step (b) with the amount of antigen/antibody complex of step (d), whereby a difference in the amount of antigen/antibody complex identifies an acute *T. vaginalis* infection in the subject.

Typically, the biological samples used in practicing the invention are vaginal washings, pap smear or other cell preparations, urine, blood or serum, or saliva samples. However, the sample in all the above various embodiments of the invention can be any biological fluid or tissue that can be used in an immunoassay that either detects antibody in the biological fluid or detects protein in the biological fluid with available polyclonal and/or monoclonal antibodies to the proteins of this disclosure, including but not limited to, lung aspirates, semen, cerebrospinal fluid, semen, prostatic fluid, sputum, joint fluid, body cavity fluid, whole cells, cell extracts, tissue, biopsy material, aspirates, exudates, vaginal washings, pap smear samples, pap smear preparations, slide preparations, fixed cells, or tissue sections from a subject, where the subject can be either female or male. Several recent reports examining infections in the lungs of immunocompromised individuals or patients with acute respiratory distress syndrome have shown the presence of *T. vaginalis* as primary or secondary infection. Therefore, it is understood that the invention may be useful for diagnosis and treatment of patients regardless of STI status, and that any biological sample may be used.

In the embodiment of identifying an acute infection in a subject, a first sample is taken at a first time point and a second sample is taken at a second time point and the amount of antibody or antigen and/or the type of antigen or antibody present in the two samples is compared. A change in the amount and/or type of antibody or antigen is indicative of an acute infection and no change in the amount and/or type of antibody or antigen is indicative of a past or chronic infection. For example, a decrease in the amount of antibody or antigen in the sample taken at the second time point (e.g., after treatment of the subject for a *T. vaginalis* infection) is indicative that the infection at the time the first sample was taken was an acute infection. Furthermore, if there is an increase in titer of antibody or amount of antigen, this would indicate an ongoing/active infection that was not diagnosed initially or that was not eliminated upon diagnosis and drug treatment. This would necessitate additional examination of body sites and tissues for the presence of organism, antigen, or antibody.

Furthermore, a *T. vaginalis* protein of this disclosure can detect, but is not limited to, a recombinant α-enolase, aldolase, GAPDH and/or α-actinin protein as described in the EXAMPLES section set forth herein, as well as peptides of the reactive epitopes, fragments, and immunologically-similar variants of such proteins, peptides and fragments. Such epitopes and recombinant proteins and peptides can be produced according to methods well known in the art and can also be produced by fractionation and/or isolation techniques, synthesis techniques, etc. that are known for producing proteins and peptides for use in immunoassays.

The term "*Trichomonas*" as used herein, includes, but is not limited to a protozoan parasite of the order Trichomonadida, genera *Ditrichomonas, Trichomonas, Tritrichomonas* and *Pentatrichomonas*, comprising multiple species that infects both humans and animals. "*Trichomonas*" refers to any *Trichomonas* species, e.g., *Tritrichomonas foetus* (also known as *Trichomonas foetus, Tt. fetus*), *Tt enteris* and *T. paviovi*, which infect cattle; *Tt. suis, Tt. rotunda* and *T. buttreyi*, which infect swine; *Dt. ovis*, which infects sheep; *Tt. equi* and *T. equibuccalis*, which infect horses; *T. anatis, Tt. eberthi, T. gallinae* and *T. gallinarum*, which infect birds; *Tt. caviae, Tt muris, Tt. wenoni, Tt. minuta* and *T. microti*, which infect rodents; *T. canistomae* and *T. felistomae*, which infect dogs and cats; and *T. tenax, T. vaginalis, Pt. hominis*, and *T. macacovaginae*, which infect primates (including humans). *Trichomonas vaginalis* as described herein includes isolates T016, T068-II, UT40, and VB102, as well as any other *T. vaginalis* isolate now known or later identified.

The term "antibody" as used herein, includes, but is not limited to a polypeptide encoded by an immunoglobulin gene or immunoglobulin genes, or fragments thereof. An antibody may be produced in a species other than the species of the subject putatively affected by a *Trichomonas* infection. "Antibody" also includes, but is not limited to, a polypeptide encoded by an immunoglobulin gene or immunoglobulin genes, or fragments thereof, which specifically binds to and recognizes the antigen-specific binding region (idiotype) of an antibody produced by the host in response to exposure to *T. vaginalis* or other *Trichomonas* species antigen(s). Antibodies may also be produced using recombinant DNA gene engineering to generate synthetic linear or conformational antibodies that recognize and bind to their cognate antigen(s).

The term "epitope" means an antigenic determinant that is specifically bound by an antibody. Epitopes usually consist of surface groupings of molecules, such as amino acids and/or sugar side chains, and may be linear or have specific three-dimensional structural characteristics, as well as specific charge characteristics.

The term "15-mer epitope" and "15-mer amino acid sequences" are used interchangeably to describe the building blocks of a "series of epitopes" (see definition of series of epitopes below). An epitope typically comprises about 3 to 15 residues which are highly immunogenic. The epitope should have enough amino acid residues so that the peptide product is large enough to be recognized, which will generally be at least 4-5 amino acids, but can be up to 11, 12, 13, 14, 15, 16, 17, 18, 19, 20, 21, 22, 23, 24, 25, 26, 27, 28, 29, 30, 31, 32, 33, 34, 35, 36, 37, 38, 39, or at least 40 amino acids. The peptide 15-mers encode highly immunogenic epitope regions (from a protein expressed by a pathogenic microorganism of interest), having at one or both ends 1 to 7 or more, e.g. 3 to 5, amino acids of naturally occurring sequence in order to mimic the tertiary structure of protein folding to recapitulate the native protein domain. These sequences are also called 15-mer epitopes in order to distinguish them from the epitope within the native protein. However, they could easily be made small or larger, generally within the range of 3 to 50 amino acids, 10 to 25 amino acids, or 12 to 20 amino acids. Those of skill in the art will recognize that 15 amino acids is considered to be a starting point or "default" size for designing short peptide sequences of epitopes. A 15-mer is thought to be sufficiently large enough to allow correct folding and presentation of an immunogenic site or protein domain, without having extraneous free ends that might hinder access to the site of interest. It can be easily understood that a 14-mer, 16-mer, or any other oligopeptide of about 3-50 amino acids could also be used in practicing the invention, so long as it comprises the essential core of the immunogenic amino acids provided in each sequence of the invention, shown in various tables herein, and is functionally immunogenic.

The terms "series of epitopes" or "string of epitopes" (SOE), "recombinant series of epitopes" (rSOE), and "string of pearls" (SOP) are used interchangeably to refer to a synthetic macromolecule encoding a plurality of epitopes, e.g. two or more epitopes. The epitopes encoded in the SOE, rSOE, or SOP macromolecules may be peptide 15-mers (or 15-mer amino acid sequences) comprising about 3 to 15 residues which are highly immunogenic. In some embodiments, the epitopes comprise more than 15 total residues. For example, a 16-mer to 40-mer epitope may include about 3 to 15 immunogenic residues. Selection of epitopes and/or 15-mer epitopes to be included in a SOE is based specificity of the sequence, i.e., having no identity to other proteins in databases. This is especially true with the SOEs that have epitopes and/or 15-mer epitopes from proteins expressed by other organisms. Thus, selecting unique sequences helps to eliminate false positives that may occur due to recognition of proteins or antibodies to proteins from other organisms. The plurality of epitopes are typically arrayed in a linear molecule linked with amino acid linkers. rSOE protein can be expressed in host cells transfected or transformed with a vector carrying a nucleic acid encoding SOE or SOP sequences.

The SOE macromolecule may include 2, 3, 4, 5, 6, 7, 8, 9, 10, 11, 12, 13, 14, 15, 16, 17, 18, 19, 20, 21, 22, 23, 24, 25, 26, 27, 28, 29, 30 or more epitopes. For example, in some embodiments up to 100 or more epitopes are included in the SOE macromolecule. As the size of the SOE macromolecule increases, the isoelectric point (pI) becomes important for the stability of the SOE macromolecule. The isoelectric point is the pH at which the macromolecule carries no net electrical charge or is electrically neutral in the statistical mean. In some embodiments, the SOE macromolecule has a pI from 3.00 to 7.00, from 4.50 to 5.50, or from 4.90 to 5.10. In some embodiments, the pI is about 5.05. When constructing such a SOE chimeric protein, the pI may be high (>9.0), which has high probability that the recombinant *E. coli* will place the protein into inclusion bodies and be unrecoverable. Decreasing the pI through selection of amino acid linkers increases the probability that *E. coli* will synthesize the protein in a soluble form for ease of recovery.

The epitopes in the SOE macromolecule may be connected by amino acid linkers. The linkers may comprise 1 to 50 or more amino acids in any sequence. In some embodiments, the linker comprises repeats of 1, 2, 3, 4, 5, or more amino acids. For example, the linker may comprise repeats of any amino acid including, but not limited to, glycine (-GG-), lysine (-KK-), glutamic acid (-EE-), asparagine (-NN-), threonine (-TT-), alanine (-AA-), leucine (-LL-), arginine (-RR-), histidine (-HH-), aspartic acid (-DD-), serine (-SS-), glutamine (-QQ-), cysteine (-CC), proline (-PP-), valine (-VV-), isoleucine (-II-), methionine (-MM-), phenylalanine (-FF-), tyrosine (-YY-), tryptophan (-WW-), and mixtures thereof. The linkers within a single SOE macromolecule may be the same or different. Selection of linker is based on the final pI of the SOE chimeric protein as well as hydrophobicity and antigenicity profiles that affects solubility of the protein.

The term "highly immunogenic" means that the amino acids encoded by the sequences indicated will selectively and specifically bind to antibodies raised against a particular sequence during a natural infection and/or immunization. For example, the epitopes, 15-mer epitopes, and SOEs of the invention from regions of *T. vaginalis* α-actinin will detect the presence of *T. vaginalis* antibodies in in vitro detection assays. Accordingly, antibodies raised against the epitopes, 15-mer epitopes, and SOEs of the invention from regions of *T. vaginalis* α-actinin will detect the presence of *T. vaginalis* α-actinin protein or protein fragments.

The terms "specifically binds to" and "specifically reactive with" refer to a binding reaction that is determinative of the presence of the antigen and antibody in the presence of a heterogeneous population of proteins and other biologics. Thus, under designated assay conditions, the specified antibodies and antigens bind to one another and do not bind in a significant amount to other components present in a sample. Specific binding to a target analyte under such conditions may require a binding moiety that is selected for its specificity for a particular target analyte. A variety of immunoassay formats may be used to select antibodies specifically reactive with a particular antigen. For example, solid-phase enzyme-linked immunosorbent assays (ELISA) are routinely used to select monoclonal antibodies specifically immunoreactive with an analyte. See Harlow and Lane (ANTIBODIES: A LABORATORY MANUAL, Cold Springs Harbor Publications, New York, (1988)) for a description of immunoassay formats and conditions that can be used to determine specific immunoreactivity. Typically a specific or selective reaction will be at least twice background signal to noise and more typically more than 10 to 100 times greater than background.

An "immunologically reactive fragment" of a protein refers to a portion of the protein or peptide that is immunologically reactive with a binding partner, e.g., an antibody, which is immunologically reactive with the protein itself.

As used herein, the term "antibody-antigen complex" can refer to an immune complex that forms when an antibody binds to its preferred or recognized antigen. The antigen may be a full-length native protein, or it may be a protein fragment, either naturally occurring or synthetic. The antigen may further be an epitope, and that epitope may be synthetic. An antigen may further be a 15-mer epitope or an SOE, as defined above. As disclosed herein, a discussion of antibody-epitope complex may further mean a complex of one or more 15-mer epitopes or SOEs and one or more antibody types. An immune complex comprising an antibody and an epitope may also be referred to as an antibody-epitope complex to distinguish it from an antibody-antigen complex, however, both antibody-epitope complexes and antibody-antigen complexes can be collectively referred to as immune complexes.

As used herein, the term "vaccine" refers to a composition that may be used to treat an individual or to provide protection against challenge, and more specifically it provides protection against a challenge mounted by exposure to or infection with a microorganism. For example, an SOE composed of an array of *T. vaginalis* epitopes in a solution suitable for injection into a subject may provide protection from trichomoniasis. An SOE comprising an array of *N. gonorrohoeae* epitopes may provide protection from gonorrohea, and an SOE comprising an array of *T. pallidum* epitopes may provide protection from syphilis.

As used herein, the term "immunogenic composition" refers to a composition comprising a SOE, rSOE, and/or SOP composed of epitopes that elicit an immune response. For example, an SOE composed of an array of *T. vaginalis* epitopes in a solution suitable for injection into a subject may elicit an immune response to *T. vaginalis* infection. An SOE comprising an array of *N. gonorrohoeae* epitopes may elicit an immune response to *N. gonorrohoeae* infection, and an SOE comprising an array of *T. pallidum* epitopes may elicit an immune response to *T. pallidum* infection.

Antibodies to *T. vaginalis* proteins can be generated using methods that are well known in the art. Such antibodies can include, but are not limited to, polyclonal, monoclonal, chimeric, humanized, single chain, Fab fragments, and fragments produced by an expression library, including phage display. (See, e.g., Paul, FUNDAMENTAL IMMUNOLOGY, 3rd Ed., 1993, Raven Press, New York, for antibody structure and terminology.)

Antibody fragments that contain specific binding sites for a *T. vaginalis* protein can also be generated. For example, such fragments include, but are not limited to, the $F(ab')_2$ fragments that can be produced by pepsin digestion of the antibody molecule, and the Fab fragments that can be generated by reducing the disulfide bridges of the $F(ab')_2$ fragments. Alternatively, Fab expression libraries can be constructed to allow rapid and easy identification of monoclonal antibody Fab fragments with the desired specificity (Huse et al., *Science* 254, 1275-1281 (1989)).

For the production of antibodies, various hosts including goats, rabbits, rats, mice, humans, and others, may be immunized by injection of chemically-stabilized whole organisms or any extract or lysate of organisms comprising total proteins or with a *T. vaginalis* protein (e.g., individual or a combination of aldolase, GAPDH, α-enolase and/or α-actinin proteins) or any fragment or oligopeptide or conjugate thereof that has immunogenic properties. One or more epitopes, 15-mer epitopes and/or SOEs may be used for injection into hosts for the production of antibodies. Depending on the host species, various adjuvants can be used to increase the immunological response. Such adjuvants include, but are not limited to, Freund's complete and incomplete adjuvant, mineral gels such as aluminum hydroxide, and surface active substances such as lysolecithin, pluronic polyols, polyanions, peptides, oil emulsions, keyhole limpet hemocyanin, and dinitrophenol. Examples of adjuvants used in humans include BCG (bacilli Calmette-Guerin) and *Corynebacterium parvum*.

Monoclonal antibodies (MAbs) to *Trichomonas vaginalis* proteins can be prepared using any technique that provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell Biol.* 62:109-120). Briefly, the procedure is as follows: an animal is immunized with a *T. vaginalis* protein, such as individual or a combination of aldolase, GAPDH, α-enolase and/or α-actinin proteins, or immunogenic fragment or oligopeptide or conjugate thereof. For example, haptenic oligopeptides of a *T. vaginalis* protein can be conjugated to a carrier protein to be used as an immunogen. Lymphoid cells (e.g., splenic lymphocytes) are then obtained from the immunized animal and fused with immortal cells (e.g., myeloma or heteromyeloma) to produce hybrid cells. The hybrid cells are screened to identify those that produce the desired antibody.

Human hybridomas that secrete human MAb can be produced by the Kohler and Milstein technique. Although human antibodies are especially preferred for treatment of humans, in general, the generation of stable human-human hybridomas for long-term production of human MAb can be difficult. Hybridoma production in rodents, especially mouse, is a very well established procedure and thus, stable murine hybridomas provide an unlimited source of antibody of select characteristics. As an alternative to human antibodies, the mouse antibodies can be converted to chimeric murine/human antibodies by genetic engineering techniques. See Oi, et al., *Bio Techniques* 4(4):214-221 (1986); Sun, et al., *Hybridoma* 5 (1986).

The MAbs of this invention specific for *T. vaginalis* protein epitopes can also be used to produce anti-idiotypic (paratope-specific) antibodies. (See e.g., McNamara et al., *Science* 220, 1325-26 (1984); Kennedy et al., *Science* 232: 220 (1986).) These antibodies resemble the *T. vaginalis* protein epitope and thus can be used as an antigen to stimulate an immune response against the *T. vaginalis* protein.

In addition, techniques developed for the production of "chimeric antibodies," the splicing of mouse antibody genes to human antibody genes to obtain a molecule with appropriate antigen specificity and biological activity can be used (Morrison, et al., *Proc. Natl. Acad. Sci.* 81:6851-6855 (1984); Neuberger, et al., *Nature* 312:604-608 (1984); Takeda, et al., *Nature* 314:452-454 (1985)). Alternatively, techniques described for the production of single chain antibodies can be adapted, using methods known in the art, to produce *T. vaginalis* protein-specific single chain antibodies. Antibodies with related specificity, but of distinct idiotypic composition, can be generated by chain shuffling from random combinatorial immunoglobin libraries (Burton, *Proc. Natl. Acad. Sci.* 88:11120-3 (1991)).

Antibodies can also be produced by inducing in vivo production in the lymphocyte population or by screening immunoglobulin libraries or panels of highly specific binding reagents as described in the literature (Orlandi, et al., *Proc. Natl. Acad. Sci.* 86:3833-3837 (1989)); Winter, et al., *Nature* 349:293-299 (1991)).

Various immunoassays can be used to identify antibodies of this invention having the desired specificity. Furthermore, a wide variety of immunoassays may be employed in the methods of this disclosure to detect antibodies and antigens of *T. vaginalis* proteins for diagnosis of *T. vaginalis* infection. Such immunoassays typically involve the measurement of antigen/antibody complex formation between a *T. vaginalis* protein or peptide and its specific antibody.

The immunoassays of the invention can be either competitive or noncompetitive. In competitive binding assays, *T. vaginalis* antigen or antibody competes with a detectably labeled *T. vaginalis* antigen or antibody for specific binding to a capture site bound to a solid surface. The concentration of labeled antigen or antibody bound to the capture agent is inversely proportional to the amount of free antigen or antibody present in the sample.

Noncompetitive assays can be, for example, sandwich assays, in which the sample analyte (target antibody) is bound between two analyte-specific binding reagents. One of the binding agents is used as a capture agent and is bound to a solid surface. The other binding agent is labeled and is used to measure or detect the resultant antigen/antibody complex by e.g., visual or instrument means. A number of combinations of capture agent and labeled binding agent can be used. For instance, antigens derived from the *T. vaginalis* can be used as the capture agent and labeled anti-human antibodies specific for the constant region of human antibodies can be used as the labeled binding agent to detect antibodies in a sample that bind the *T. vaginalis* antigen. Goat, sheep and other non-human antibodies specific for human immunoglobulin constant regions are well known in the art. Alternatively, the anti-human antibodies can be the capture agent and the antigen can be labeled. Other proteins capable of specifically binding human immunoglobulin constant regions, such as protein A, protein L or protein G can also be used as the capture agent or labeled binding agent. These proteins are normal constituents of the cell walls of streptococcal bacteria. They exhibit a strong non-immunogenic reactivity with immunoglobulin constant regions from a variety of species. (See, e.g., Kronval, et al., *J. Immunol.*, 111:1401-1406 (1973); Akerstrom, et al., *J. Immunol.*, 135: 2589-2542 (1985)).

The non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or *T. vaginalis* protein or epitopes of proteins either singly or in combination of aldolase, GAPDH, α-enolase and/or α-actinin proteins, can be conjugated or otherwise linked or connected (e.g., covalently or non-covalently) to a solid support (e.g., bead, plate, slide, dish, membrane or well) in accordance with known techniques. Further, a plasmid construct encoding a recombinant protein that contains the epitopes of aldolase, GAPDH, α-enolase and/or α-actinin proteins detected by human antibodies following infection by and exposure to *T. vaginalis* can be used. This protein comprised by a series of the epitope sequences is referred to as a SOE, rSOE, or SOP with each "pearl" representing an individual epitope, and the epitope can be separated by amino acid linkers, such as glycine (-GG-), lysine (-KK-), or glutamic acid (-EE-) repeats. Antibodies can also be conjugated or otherwise linked or connected to detectable groups such as radiolabels (e.g., $^{35}S$, $^{125}I$, $^{32}P$, $^{13}H$, $^{14}C$, $^{131}I$), enzyme labels (e.g., horseradish peroxidase, alkaline phosphatase), gold beads, chemiluminescent labels, ligands (e.g., biotin) and/or fluorescence labels (e.g., fluorescein isothiocyanate) in accordance with known techniques.

A variety of organic and inorganic polymers, both natural and synthetic can be used as the material for the solid surface. Non-limiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, etc., immunoprecipitation, competitive binding assays and immunohistochemical staining. These and other assays are described, among other places, in Hampton et al. (*Serological Methods, a Laboratory Manual*, APS Press, St Paul, Minn. (1990)) and Maddox, et al. (*J. Exp. Med.* 158:1211-1216 (1993)).

The methods of this disclosure can also be carried out using a variety of solid phase systems, such as described in U.S. Pat. No. 5,879,881, as well as in a dry strip lateral flow system, such as described, for example, in U.S. Patent Publication No. 20030073147, the entire contents of each of which are incorporated by reference herein.

A subject is any animal that can be infected by *Trichomonas vaginalis*. In certain embodiments, the subject is human.

In addition, a nucleic acid (DNA) having the nucleotide sequence or a substantially similar nucleotide sequence of the gene encoding the *T. vaginalis* protein of this disclosure can be used as a probe in a nucleic acid hybridization assay for the detection of a *T. vaginalis* protein in various tissues or body fluids of a subject. Further, DNA encoding the sequence of the epitopes, 15-mer epitopes, and/or SOEs detected by human serum following infection by and exposure to *T. vaginalis* can be used as a probe in a nucleic acid hybridization assay for the detection of a *T. vaginalis* protein in various tissues or body fluids of a subject. The probe can be used in any type of nucleic acid hybridization assay including Southern blots (Southern, 1975, *J. Mol. Biol.*

98:508), Northern blots (Thomas et al., 1980, *Proc. Natl Acad. Sci. U.S.A.* 77:5201-05), colony blots (Grunstein, et al., 1975, *Proc. Natl Acad. Sci. U.S.A.* 72:3961-65), slot blots, dot blots, etc. Stringency of hybridization can be varied depending on the requirements of the assay according to methods well known in the art. Assays for detecting nucleic acid encoding a *T. vaginalis* protein in a cell, or the amount thereof, typically involve, first contacting the cells or extracts of the cells containing nucleic acids therefrom with an oligonucleotide probe that specifically binds to nucleic acid encoding a *T. vaginalis* protein or peptide as described herein (typically under conditions that permit access of the oligonucleotide to intracellular material), and then detecting the presence or absence of binding of the oligonucleotide probe thereto. Any suitable assay format can be employed (see, e.g., U.S. Pat. Nos. 4,358,535; 4,302,204; 4,994,373; 4,486,539; 4,563,419; and 4,868,104, the disclosures of each of which are incorporated herein by reference in their entireties).

The antibodies of this disclosure can be used in in vitro, in vivo and/or in in situ assays to detect a *T. vaginalis* protein or peptide of this disclosure.

Also as used herein, the terms peptide and polypeptide are used to describe a chain of amino acids, which correspond to those encoded by a nucleic acid (DNA). A peptide usually describes a chain of amino acids of from two to about 30 amino acids and polypeptide usually describes a chain of amino acids having more than about 30 amino acids. It is understood, however, that 30 is an arbitrary number with regard to distinguishing peptides and polypeptides and the terms may be used interchangeably for a chain of amino acids around 30. The peptides and polypeptides of the present invention are obtained by isolation and purification of the peptides and polypeptides from cells where they are produced naturally or by expression of a recombinant and/or synthetic nucleic acid encoding the peptide or polypeptide. The peptides and polypeptides of this invention can be obtained by chemical synthesis, by proteolytic cleavage of a polypeptide and/or by synthesis from nucleic acid encoding the peptide or polypeptide. The term polypeptide can refer to a linear chain of amino acids or it can refer to a chain of amino acids, which have been processed and folded into a functional protein. The term polypeptide can refer also the sequence of the epitopes. Using *T. vaginalis* as an example, the selected epitopes from the proteins of aldolase, GAPDH, α-enolase, and/or α-actinin are arranged so that each epitope is separated by an amino acid linker, such as repeats of glycine, lysine, or glutamic acid in the form of an SOE, rSOE, or SOP.

It is also understood that the peptides and polypeptides of this disclosure may also contain conservative substitutions where a naturally occurring amino acid is replaced by one having similar properties and which does not alter the function of the peptide or polypeptide. Such conservative substitutions are well known in the art. Thus, it is understood that, where desired, modifications and changes may be made in the nucleic acid and/or amino acid sequence of the peptides and polypeptides of the present invention and still obtain a peptide or polypeptide having like or otherwise desirable characteristics. Such changes may occur in natural isolates or may be synthetically introduced using site-specific mutagenesis, the procedures for which, such as mismatch polymerase chain reaction (PCR), are well known in the art. One of skill in the art will also understand that polypeptides and nucleic acids that contain modified amino acids and nucleotides, respectively (e.g., to increase the half-life and/or the therapeutic efficacy of the molecule), can be used in the methods of the invention.

"Nucleic acid" as used herein refers to single- or double-stranded molecules which may be DNA, comprised of the nucleotide bases A, T, C and G, or RNA, comprised of the bases A, U (substitutes for T), C, and G. The nucleic acid may represent a coding strand or its complement. Nucleic acids may be identical in sequence to a sequence that is naturally occurring or may include alternative codons that encode the same amino acid as that which is found in the naturally occurring sequence. Furthermore, nucleic acids may include codons that represent conservative substitutions of amino acids as are well known in the art. The nucleic acids of this invention can also comprise any nucleotide analogs and/or derivatives as are well known in the art.

As used herein, the term "isolated nucleic acid" means a nucleic acid separated or substantially free from at least some of the other components of the naturally-occurring organism, for example, the cell structural components commonly found associated with nucleic acids in a cellular environment and/or other nucleic acids. The isolation of nucleic acids can therefore be accomplished by well-known techniques such as cell lysis followed by phenol plus chloroform extraction, followed by ethanol precipitation of the nucleic acids. The nucleic acids of this disclosure can be isolated from cells according to methods well known in the art for isolating nucleic acids. Alternatively, the nucleic acids can be synthesized according to standard protocols well described in the literature for synthesizing nucleic acids. Modifications to the nucleic acids are also contemplated, provided that the essential structure and function of the peptide or polypeptide encoded by the nucleic acid are maintained.

The nucleic acid encoding the peptide or polypeptide of this disclosure can be part of a recombinant nucleic acid construct comprising any combination of restriction sites and/or functional elements as are well known in the art that facilitate molecular cloning and other recombinant DNA manipulations. Thus, the present disclosure further provides a recombinant nucleic acid construct comprising a nucleic acid encoding a peptide and/or polypeptide of this disclosure. The protein products of combinations of genetic sequences into a recombinant nucleic acid are sometimes referred to as chimeric proteins, polypeptides and/or peptides, and the SOEs of the disclosure can be called such.

The present disclosure further provides a vector comprising a nucleic acid encoding a peptide and/or polypeptide of this disclosure. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise, for example, viral nucleic acid including, but not limited to, vaccinia virus, adenovirus, retrovirus, alphavirus and/or adeno-associated virus nucleic acid. The nucleic acid or vector can also be in a liposome or a delivery vehicle, which can be taken up by a cell via receptor-mediated or other type of endocytosis.

The nucleic acid can be in a cell, which can be a cell expressing the nucleic acid whereby a peptide and/or polypeptide of this disclosure is produced in the cell. In addition, the vector can be in a cell, which can be a cell expressing the nucleic acid of the vector whereby a peptide and/or polypeptide of this disclosure is produced in the cell. It is also contemplated that the nucleic acids and/or vectors can be present in a host (e.g., a bacterial cell, a cell line, a transgenic animal, etc.) that can express the peptides and/or polypeptides of the present disclosure.

In some embodiments, for recombinant production of the chimeric proteins, polypeptides and/or peptides of this disclosure in prokaryotes, there are numerous *Escherichia coli* (*E. coli*) expression vectors known to one of ordinary skill in the art useful for the expression of nucleic acid encoding proteins or peptides of this invention. Other microbial hosts suitable for use include bacilli, such as *Bacillus subtilis*, and other enterobacteria, such as *Salmonella, Shigella*, and *Serratia*, as well as various *Pseudomonas* species. These prokaryotic hosts can support expression vectors that will typically contain sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence and have ribosome binding site sequences for example, for initiating and completing transcription and translation. If necessary, an amino terminal methionine can be provided by insertion of a Met codon 5' and in-frame with the coding sequence of the protein. Also, the carboxy-terminal extension of the protein can be removed using standard oligonucleotide mutagenesis procedures.

Additionally, yeast expression systems and baculovirus systems, which are well known in the art, can be used to produce the chimeric peptides and polypeptides of this disclosure.

The vectors of this disclosure can be transferred into a cell by well-known methods, which vary depending on the type of cell host. For example, calcium chloride transfection is commonly utilized for prokaryotic cells, whereas calcium phosphate treatment, lipofection or electroporation can be used for other cell hosts.

The present disclosure further provides a kit for detection of microorganism-specific proteins. In the case of *T. vaginalis*, at least one antibody is selected from the group consisting of aldolase, GAPDH, α-enolase and/or α-actinin antibodies, as disclosed in the sequence listings and tables herein. Such a kit can comprise one or more proteins or antibodies of the disclosure, along with suitable buffers, wash solutions, dilution buffers, secondary antibodies, and detection reagents for the detection of antigen/antibody complex formation under various conditions. In another embodiment, a kit can comprise at least one amino acid sequence selected from the group consisting of SOE, polypeptide, a peptide, and antigenic fragment comprising the amino acid sequence (epitope) detected by the monoclonal antibody and/or a fusion protein or peptide comprising an individually or in combination the epitopes of interest, along with suitable buffers, wash solutions, dilution buffers, secondary antibodies, detection reagents, etc. for the detection of antigen/antibody complex formation under various conditions.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the hundredth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The present invention is more particularly described in the Examples set forth below, which are not intended to be limiting of the embodiments of this invention.

Example 1. Monoclonal Antibodies (MAbs) that Specifically Bind a *Trichomonas vaginalis* Fructose-1,6-Biphosphate Aldolase (Aldolase), glyceraldehyde-3-phosphate Dehydrogenase (GAPDH), and/or α-Enolase Proteins Detecting a *T. vaginalis* protein selected from aldolase, GAPDH, α-enolase and/or α-actinin proteins, in a sample, includes contacting a sample with an antibody that specifically binds a *T. vaginalis* protein or epitopes of proteins either singly or in combination selected from the group of aldolase, GAPDH, α-enolase and α-actinin proteins, under conditions whereby an antigen/antibody complex can form, and detecting formation of an antigen/antibody complex, thereby detecting the protein in the sample. The method may be performed using an immunoassay, such as a dot blot, ELISA, or other high-throughput immunoassay, with ELISA being the preferred immunoassay.

In particular embodiments, the antibody employed in the methods of this disclosure is an antibody that specifically binds a *T. vaginalis* protein or epitopes of the proteins either singly or in combination selected from aldolase, GAPDH, α-enolase and/or α-actinin proteins. A non-limiting example of an antibody that specifically binds the known amino sequence of the epitope of a *T. vaginalis* protein selected from aldolase, GAPDH, α-enolase and/or α-actinin proteins is monoclonal antibody ALDwsu1 (aldolase), ALDwsu2 (aldolase), GAPwsu2 (GAPDH), GAPwsu3 (GAPDH), ENOwsu2 (α-enolase), ENOwsu3 (α-enolase), ENOwsu4 (α-enolase), ENOwsu6 (α-enolase) and HA423 (α-actinin).

A library of new monoclonal antibodies (MAbs) was generated toward the *T. vaginalis* proteins aldolase, glyceraldehyde-3-phosphate-dehydrogenase, and α-enolase proteins. The newly-generated MAbs are all $IgG_1$ isotype. MAbs B44, B43, and HA423 are included for comparative purposes and were generated at the University of Texas Health Science Center at San Antonio but the epitope amino acid sequences were unknown until now. All of the newly-generated MAbs readily detect the surface of trichomonads as evidenced by whole cell-enzyme-linked immunosorbent assay (WC-ELISA) and fluorescence of non-permeabilized organisms. The respective proteins are detected by immunoblot after SDS-PAGE blotting the proteins onto nitrocellulose after probing with individual MAbs. The amino acid sequences detected by the respective MAbs (epitopes) are provided, and it is noteworthy that the epitopes detected by the MAbs generated at WSU are different from that B44 and B43 MAbs.

In certain embodiments, an antibody of this disclosure is not cross-reactive with human epithelial cell extracts or other protozoan protein extracts (e.g., *G. lamblia*, *E. histolytica*, *A. castellanii*, *L. major*), fungi (*Candida* and *Pneumocystis*), and bacteria (oral and vaginal bacterial flora). In yet other embodiments, an antibody of this disclosure does not bind or react with *T. vaginalis* adhesin proteins.

Detection of Fixed *Trichomonas vaginalis* Protein in Fixed Cell Preparations.

Pap smears were prepared using methanol (MeOH) as a fixative with MeOH in the range of 20% to 80%. Trichomonads are readily fixed by incubation in MeOH prepared in PBS buffer and retain integrity as visualized by darkfield microscopy. Surface-exposed epitopes are readily detected by MAbs as shown in Table 1.

The following ELISA protocol used for pap smear was used to show immuno-detection of protein on MeOH-fixed trichomonads immobilized onto wells of microtiter plates.

1. Overnight (o/n) cultures of *T. vaginalis* grown using standard protocols in medium were washed twice with ice-cold PBS.
2. Trichomonads were fixed o/n at 4° C. (12 h to 18 h) using 20% MeOH (different concentrations of MeOH yield similar results) at a density of $10^7$ per milliliter (ml).
3. 100 microliters (μl) of different dilutions of parasites in MeOH fixative were added to individual wells of 96-well microtiter plates, and plates were placed in 37° C. incubator overnight.
4. To dried wells was added 100 μl of a solution of 1% BSA in PBS-1% Tween (PBS-T) and incubated at 37° C. for 30 min.
5. Wells were then washed 3-times (3×) with PBS-T followed by addition of 100 μl of each MAb (primary antibody) to wells. Negative controls included PBS (absence of primary MAb) and the addition of MAb L64, which detects a small-sized (17-kDa) cytoplasmic protein. (NOTE: This MAb of the same isotype ($IgG_1$) does not detect the parasite surface showing the integrity of parasites by fixation.) Wells were incubated for 60 min at 37° C.

TABLE 1

New MAbs generated and reactive with aldolase (ALD), GAPDH (GAP), α-enolase (ENO) and α-actinin.

| | protein | original name | WSU MAb, designation[1] | amino acid numbers in protein | epitope sequence | surface detection | size (kDa) |
|---|---|---|---|---|---|---|---|
| SEQ ID NO: 1 | ALD | ALD12A | ALDwsu-1 | 142-149 | RPDYVTVE | yes | 36.3 |
| SEQ ID NO: 2 | ALD | ALD64A | ALDwsu-2 | 166-173 | KLITYTRPE | yes | " |
| SEQ ID NO: 3 | ALD | B44 | N/A | 448-455 | ERIQKYTR | yes | 52 |
| SEQ ID NO: 4 | ALD | ALD11A | ENOwsu-2 | 364-371 | DDLYTTNP | yes | " |
| SEQ ID NO: 5 | ALD | ALD13B | ENOwsu-3 | 7-14 | AIVKECIA | yes | " |
| SEQ ID NO: 6 | ALD | ALD25 | ENOwsu-4 | 463-470 | LKEHDMLA | yes | " |
| SEQ ID NO: 7 | ENO | ALD55 | ENOwsu-6 | 64-71 | YLGRVTLA | yes | " |
| SEQ ID NO: 8 | GAP | B43 | N/A | 205-212 | RRARAAGM | yes | 39.2 |
| SEQ ID NO: 9 | GAP | ALD30A | GAPwsu-2 | 70-77 | KSIGGRLG | yes | " |
| SEQ ID NO: 10 | GAP | ALD32C | GAPwsu-3 | 34-44 | YLLKYDTAHRA | yes | " |
| SEQ ID NO: 11 | ACT | HA423 | N/A | 649-653 | YKVTY | yes | 106.2 |

6. After washing 3× with PBS-T, 100 μl of a solution of secondary horseradish peroxidase-conjugated goat anti-mouse IgG antibody was added to wells followed by incubation at 37° C. for 30 min.
7. The wells were again washed 3× with PBS-T prior to addition of 100 μl of color development reagent. After 15 min, the microtiter well plates were read for intensity of optical density at 405 nm wavelength to measure absorbance values. A higher the absorbance value at 405 nm indicates strong immunoreactivity by MAb with the protein antigen on the surface of MeOH-fixed parasites.

Figure 2:
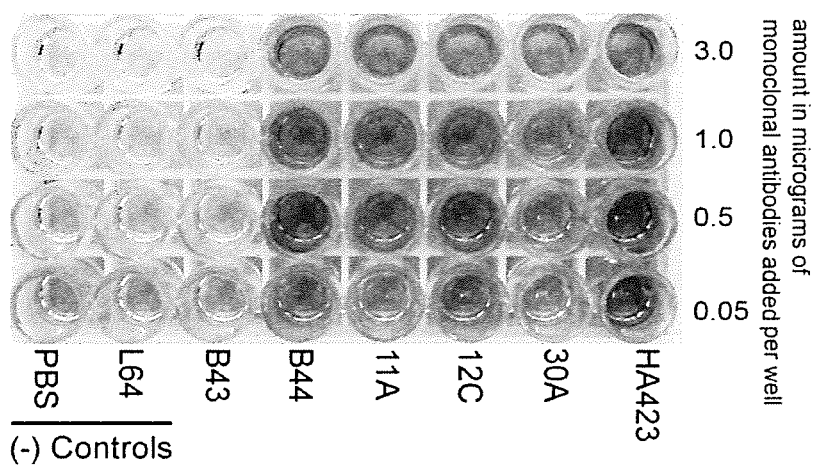
FIG. 2 shows detection of *T. vaginalis* using different amounts of individual MAbs to show specificity of the MAbs.

Results are shown in FIGS. 1 and 2. Among noteworthy findings are the following:
a) Sensitivity was ≥1 organism per μl of sample. Wells were incubated with 100 μl of the parasite suspension ≥10³/ml. At the lowest density, this is equal to 100 organisms added to each well.
b) All trichomonad isolates are readily detected.
c) Parasite preparations made with a poly-bacterial contamination does not interfere with MAb detection.
d) The presence of epithelial cells contaminating trichomonad preparations does not interfere with MAb detection.
e) Newly-generated MAbs give higher signal compared to the HA423 MAb patented to the University of Texas system.
f) Protein was detected using the range of MeOH for fixation.
g) The signal was enhanced when a cocktail of three MAbs, one each for aldolase, GAPDH, and α-enolase, was used.

Example 2. Detection of *Trichomonas vaginalis* Proteins and Antibodies in Saliva

*T. vaginalis* is a urogenital, mucosal parasite. Presently, there exists a point-of-care, antigen detection, lateral flow, immunochromagraphic diagnostic that is used for women. This diagnostic is not useful for diagnosis in men. This diagnostic is invasive for women, because it requires obtaining a vaginal swab. Therefore, there is a need for a different, non-invasive diagnostic that will work for both men and women.

Both female and male patients make specific anti-trichomonad surface protein IgG antibody. This antibody is detectable in serum and vaginal washes in women and serum in males. Antibody at one mucosal site makes it possible to detect the antibody at distant mucosal sites. Patients are known to make antibody to the proteins aldolase, GAPDH, α-enolase and α-actinin, making these proteins candidates for detection by saliva. Therefore, a diagnostic based on saliva antibody that detects these proteins or epitopes of the proteins either singly or in combination immobilized on a platform represents a diagnostic that is used for both female and male patients.

The availability of the MAbs to these proteins permits purification of recombinant proteins from cDNA expression libraries or by purification by MAb-affinity column chromatography. Alternatively, the epitopes known to be reactive by sera of both women and men represent targets that can be synthesized and immobilized for detection by saliva. Therefore, the individual or combination of aldolase, GAPDH, and α-enolase proteins or the combination of reactive epitopes of the proteins aldolase, GAPDH, and α-enolase are reagents used in a non-invasive, oral-saliva based diagnostic. Finally, the polypeptide either synthesized or derived from recombinant DNA that possess the sequence of the epitopes in the proteins of aldolase, GAPDH, α-enolase, and/or α-actinin whereby each epitope is separated by such amino acids as glycine, lysine, or glutamic acid (SOE) is a reagent used in a non-invasive, oral-saliva based diagnostic.

Patient saliva has antibody specific to whole cell *T. vaginalis* and to trichomonad proteins of aldolase, GAPDH, α-enolase, and/or α-actinin. A whole cell-ELISA was carried out, in which microtiter wells were coated with whole *T. vaginalis* cells. Saliva of individual *T. vaginalis*-infected patients and pooled saliva of healthy, uninfected individuals were then tested for reactive IgG using horse radish peroxidase-conjugated anti-human IgG secondary antibody. Each patient shows elevated absorbance values compared to the control pooled saliva of uninfected individuals. This study demonstrates the presence of IgG antibody reactive to whole *T. vaginalis* proteins. Wells coated with whole cells tested separately using rabbit anti-*T. vaginalis* serum or with a MAb served as positive controls and were also used for standardization to show similar reactions among wells. Non-reactive serum of men and women and prebleed normal rabbit serum served as negative controls.

In separate experiments, the individual sera of women and men highly reactive with the whole cell-ELISA and with each of the aldolase, GAPDH, α-enolase, and α-actinin proteins above were each reacted with overlapping, synthetically-made dodecapeptides comprising the entire amino acid sequence of the aldolase, GAPDH, α-enolase proteins and α-actinin proteins. The overlapping dodecapeptides were spotted (immobilized) onto a membrane that was then probed individually with 10% dilution of highly WC-ELISA reactive sera of women or men. The sera detected all of the epitopes to which antibody was present. No dodecapeptides were detected by negative control, unreactive sera of women and men. This study demonstrates the existence and immunoreactivity of sera of both women and men to various epitopes and also demonstrated that the women and men sera detected the same epitopes recognized by the MAbs included in Table 1 to the aldolase, GAPDH, α-enolase and α-actinin proteins.

In yet another experiment, the individual sera of women and men highly reactive with *T. vaginalis* organisms and with each of the aldolase, GAPDH, α-enolase, and α-actinin proteins above were each reacted with synthetic 15-mer peptides possessing the epitopes of the aldolase, GAPDH, α-enolase, and α-actinin proteins either singly or in combination were immobilized onto a membrane that was then probed individually with 10% dilution of highly WC-ELISA reactive sera of women or men. The sera detected all of the epitopes to epitopes singly and in combination. No peptides singly or in combination were detected by negative control, unreactive sera of women and men. This study demonstrates the existence and immunoreactivity of sera of both women and men to various epitopes and also demonstrated that the women and men sera detected the same epitopes recognized by the MAbs included in Table 1 to the aldolase, GAPDH, α-enolase and α-actinin proteins.

In yet another experiment, the individual sera of women and men highly reactive with *T. vaginalis* organisms and with each of the aldolase, GAPDH, α-enolase, and α-actinin proteins above were each reacted with a recombinant polypeptide possessing the epitopes of the aldolase, GAPDH, α-enolase, and α-actinin proteins (SOE) immobilized onto a membrane that was then probed individually with 10% dilution of highly WC-ELISA reactive sera of women or men. The sera detected all of the epitopes this recombinant polypeptide possessing the epitopes of the aldolase, GAPDH, α-enolase, and α-actinin proteins. No peptides singly or in combination were detected by negative control, unreactive sera of women and men. This study demonstrates the existence and immunoreactivity of sera of both women and men to various epitopes and also demonstrated that the women and men sera detected the same epitopes recognized by the MAbs included in Table 1 to the aldolase, GAPDH, α-enolase and α-actinin proteins.

No crossreactivity of saliva antibody between *T. vaginalis* and the opportunistic oral *T. tenax*. Saliva of humans uninfected with *T. vaginalis* has no detectable antibody using any of the ELISA assays mentioned above. Thus, the existence of immunocrossreactive antibodies in saliva of patients to *T. tenax*, the oral trichomonad will be non-existent. *T. tenax* organisms are not readily apparent in the oral cavity and are not detectable in individuals even if there is severe periodontitis.

Demonstration of specific anti-*T. vaginalis* antibody in saliva of patients. Standard ELISA can demonstrate the existence of saliva antibody in all patients. The assays can be optimized to minimize any crossreactive antibody to *T. tenax* and to monitor the level of saliva antibody among the patients, although, as just mentioned above, there is no evidence of salivary antibody crossreactivity with *T. tenax*. Three different assays provide a basis by which to determine the level of antibody to trichomonad proteins in saliva. ELISA protocols that bind non-specific sites on the coated wells with irrelevant proteins, such as BSA and/or or skim milk, can be employed. The first ELISA has whole intact trichomonads coated onto 96-well microtiter plates as antigen for saliva antibody detection, and this whole cell-ELISA employs standard conditions. For this whole cell ELISA, MeOH-fixed trichomonads can be used, or, alternatively, PBS-washed organisms can be added to wells and allowed to dry overnight. Then ethanol is added to the dried wells, and wells allowed to dry and fix the trichomonads onto the wells. The second ELISA has purified IgG of high-titered rabbit antisera to total trichomonad proteins coated onto microtiter wells. Then, trichomonad protein antigens from a detergent extract of *T. vaginalis* will bind to the IgG-coated wells after incubation. The bound trichomonad proteins provide antigen detectable by saliva antibody. Similarly, the third assay has a cocktail of MAbs to aldolase, GAPDH, α-enolase and α-actinin-coated onto microtiter wells. These MAbs-coated wells bind protein antigen from the trichomonal extract. These parasite proteins bound to MAbs will now serve as antigen for saliva antibody. The second and third sandwich-ELISAs take advantage of the knowledge that women and men make serum antibody to various epitopes of each protein (Table 1). It is expected that saliva antibody, like serum antibody, is directed to epitopes different from those of rabbit antiserum and that we have now shown are detected by serum antibody of women and men infected and exposed to *T. vaginalis*.

After treatment of freshly prepared ELISA plates with skim milk to decrease non-specific interactions, select samples of saliva from patients and from uninfected control individuals can be diluted in PBS without or with a *T. tenax* detergent extract prior to addition of standard 100 μl volumes to microtiter wells. PBS without *T. tenax* extract provides duplicates of the same saliva. Initial data shows that saliva does not have any antibody to *T. tenax*, and data suggests that any concern of crossreactivity is nonexistent. Experiments indicate that a 60 min to 120 min incubation at 37° C. is optimal. After washing, horseradish peroxidase-conjugated secondary goat anti-human IgG, anti-IgA, or Ig (IgG+IgA+IgM) Ab is added, followed by color development with substrate. In these assays, purified trichomonad protein called P230 that is a prominent immunogen eliciting a vaginal IgG antibody response will serve as a positive control for saliva IgG antibody.

Saliva antibody from women infected with *T. vaginalis* and after treatment is tested. Saliva can be obtained on at least two occasions post-treatment to assess the nature of the antibody response following removal of trichomonads from the urogenital tract through drug treatment. Saliva from male partners of infected women can also be examined to confirm the validity of this diagnostic for both infected partners.

Example 3. *Trichomonas vaginalis* Proteins Detected in Urine by MAbs

The numerous proteins that are increased in expression during infection, found in secretions of patients, and are readily secreted by trichomonads have been identified and include aldolase, GAPDH, α-enolase and α-actinin. Both women and men patients infected with *T. vaginalis* have trichomonads in urine. This means that many proteins and/or intact organisms may be detected in urine samples for both women and men. Among the many secreted proteins found in large amounts are those to which the new MAbs have been generated, and these proteins are aldolase, GAPDH, and/or α-enolase. These proteins are readily detected by immunoblots with the MAbs to aldolase, GAPDH, α-enolase and/or α-actinin. Therefore, these proteins in soluble form in urine can be immobilized through filtration and can then be detected by the MAbs. Although the present invention has been described with reference to specific details of certain embodiments thereof, it is not intended that such details should be regarded as limitations upon the scope of the invention except as and to the extent that they are included in the accompanying claims. Throughout this application, various patents, patent publications and non-patent publications are referenced. The disclosures of these patents, patent publications, and non-patent publications in their entireties are incorporated by reference into this application in order to more fully describe the state of the art to which this invention pertains.

Overview of Examples 4 Through 7: Identification of Diagnostic Immunogenic Epitopes of Aldolase, GAPDH, α-Enolase, and α-Actinin that are Reactive with Sera of Female and Male Patients and Monoclonal Antibodies (MAbs) and are Unique to *Trichomonas vaginalis*

We have identified epitopes of the *T. vaginalis* proteins aldolase, GAPDH, α-enolase, and α-actinin with little or no identity to other sexually transmitted microorganisms [*Treponema pallidum* (syphilis), *Chlamydia trachomatis* (chlamydia), *Neisseria gonorrhoeae* (gonorrhea), and *Candida albicans* (yeast)], normal flora bacteria (*E. coli*), yeast (*Saccharomyces cerevisiae*), and humans (*Homo sapiens*) and are, therefore, unique targets to diagnose infection and exposure to *T. vaginalis*. These peptide epitopes have significance for diagnosis of infection with *T. vaginalis*. The experimental approach likewise identified epitopes in the trichomonad GAPDH and α-enolase proteins with significant identity to peptide epitopes in the human proteins to which individuals infected with *T. vaginalis* make antibody. Such antibody during a *T. vaginalis* infection may have consequences for autoimmunity. The GAPDH peptide epitopes were found to have high sequence identity to the GAPDH protein of *Tritrichomonas suis* parasite of porcine, which is a synonym for *Tritrichomonas foetus*-bovine, the causative agent of fetal wastage in cattle, *Tritrichomonas foetus*-cat, causative agent for chronic large-bowel diarrhea, and *Tritrichomonas mobilensis*, enteric protozoan of squirrel monkeys (Lun, Z.-R., et al., Trends in Parasitol., 21:122-125, 2005; Reinmann, K., et al., Veterinary Parasitol., published ahead of print, doi: 10.1016/j.vetpar.2011.09.032.). Therefore, these epitope characterization experiments have identified diagnostic epitopes of the important pathogenic porcine, cattle, cat, and squirrel monkey trichomonads (*Tritrichomonas suis, T. foetus*-bovine, *T. foetus*-cat, and *T. mobilensis*).

Overlapping dodecapeptides of each of the aldolase, GAPDH, α-enolase and α-actinin proteins were examined for immunoreactivity with the sera of women and men patients and MAbs. The overlapping dodecapeptides for each of the proteins were immobilized in succeeding spots on a template that permitted detection by antibodies. This procedure is standard for identification of epitopes immunogenic during infection or that react with serum antibody and MAbs. This approach permits analysis of the antibody responses that are similar and distinct between the sera of women and men patients in addition to localizing the epitopes detected by MAbs. Further, it is possible to perform comparative analysis of the amino acid sequences of similar functional proteins of humans (*Homo sapiens*), of other sexually transmitted bacterial pathogens (*Neisseria gonorrhoeae, Treponema pallidum* subsp. *pallidum* strain Nichols, and *Chlamydia trachomatis*), of yeast (*Saccharomyces cerevisiae* and *Candida albicans*), and of other human bacterial pathogens (*Streptococcus pyogenes, Streptococcus pneumoniae*, and *Staphylococcus aureus*). Alignment of the amino acid sequences reveals whether the peptide sequences are unique to *Trichomonas vaginalis*, are identical and common to other *Trichomonas* sp. (*T. suis* and synonyms *T. foetus*-bovine, *T. foetus*-cat, and *T. mobilensis*), and share high or identical sequence identity with humans (*H. sapiens*) that may have significance for autoimmune reactions.

Accompanying each of the following experiments are tables showing the diagnostic immunogenic sequences reactive with female and male sera and MAbs that are unique to *T. vaginalis*. Other tables illustrate the extent of sequence identity between the *T. vaginalis* amino acid sequences with those of other bacteria, yeast, and human. These alignments were obtained from BLAST amino acid sequence alignments of proteins. Spot numbers on the overlapping peptides and the numbers of amino acids in the *T. vaginalis* peptide epitopes reactive with female (F) and male (M) sera and MAbs and that are unique to *T. vaginalis* are provided under the column labeled "unique Tv epitope for diagnosis" and given a positive (+) sign. *T. vaginalis* peptide epitopes with high sequence identity to *Tritrichomonas suis* (synonym with *T. foetus*-bovine, *T. foetus*-cat, and *T. mobilensis*) protein epitope sequences are also disclosed. These peptides are reactive with female or male sera or both, and illustrate their utility also for diagnosis of porcine, cattle, cat, and squirrel monkey trichomonads. The peptides of the proteins α-enolase and GAPDH with high sequence identity to human protein epitopes and with possible autoimmune crossreactivity are listed, and the *T. vaginalis* (Tv) peptide sequences are aligned with the human sequences (Hu).

Example 4. Identification of Diagnostic Immunogenic Epitopes of Aldolase Unique to *T. vaginalis*

TABLE 2

Identification of diagnostic immunogenic epitopes of fructose-1,6-biphosphate aldolase protein that are unique to *T. vaginalis* (Tv).

| | no. amino acid sequence | epitope sequence | female patient sera reactivity | male patient sera reactivity | Mab reactivity | unique To Tv |
|---|---|---|---|---|---|---|
| SEQ ID NO: 12 | 40-47 | AIITASVK | F1 | | | |
| SEQ ID NO: 13 | 58-65 | AGARKYAN | | M1 | | |
| SEQ ID NO: 14 | 61-71 | RKYANQTMLRY | F2 | | | |
| SEQ ID NO: 15 | 91-101 | PIVLHLDHGDS | F3 | | | |
| SEQ ID NO: 1 | 142-149 | RPDYVTVE | | | ALD12A | |
| SEQ ID NO: 2 | 166-173 | KHYTYTRPE | | | ALD64A | + |
| SEQ ID NO: 16 | 169-179 | YTRPEEVQDFV | F4 | | | |
| SEQ ID NO: 17 | 193-203 | TSHGAYKFPPG | F5 | | | |
| SEQ ID NO: 18 | 231-241 | SIPQEYVEMVN | F6 | | | |
| SEQ ID NO: 19 | 277-287 | RMVMTGTIRRL | | M2 | | |
| SEQ ID NO: 20 | 298-305 | RQYLGEAR | F7 | M3 | | |
| SEQ ID NO: 21 | 304-311 | ARTKLTEM | F8 | | | + |

Figure 3B:
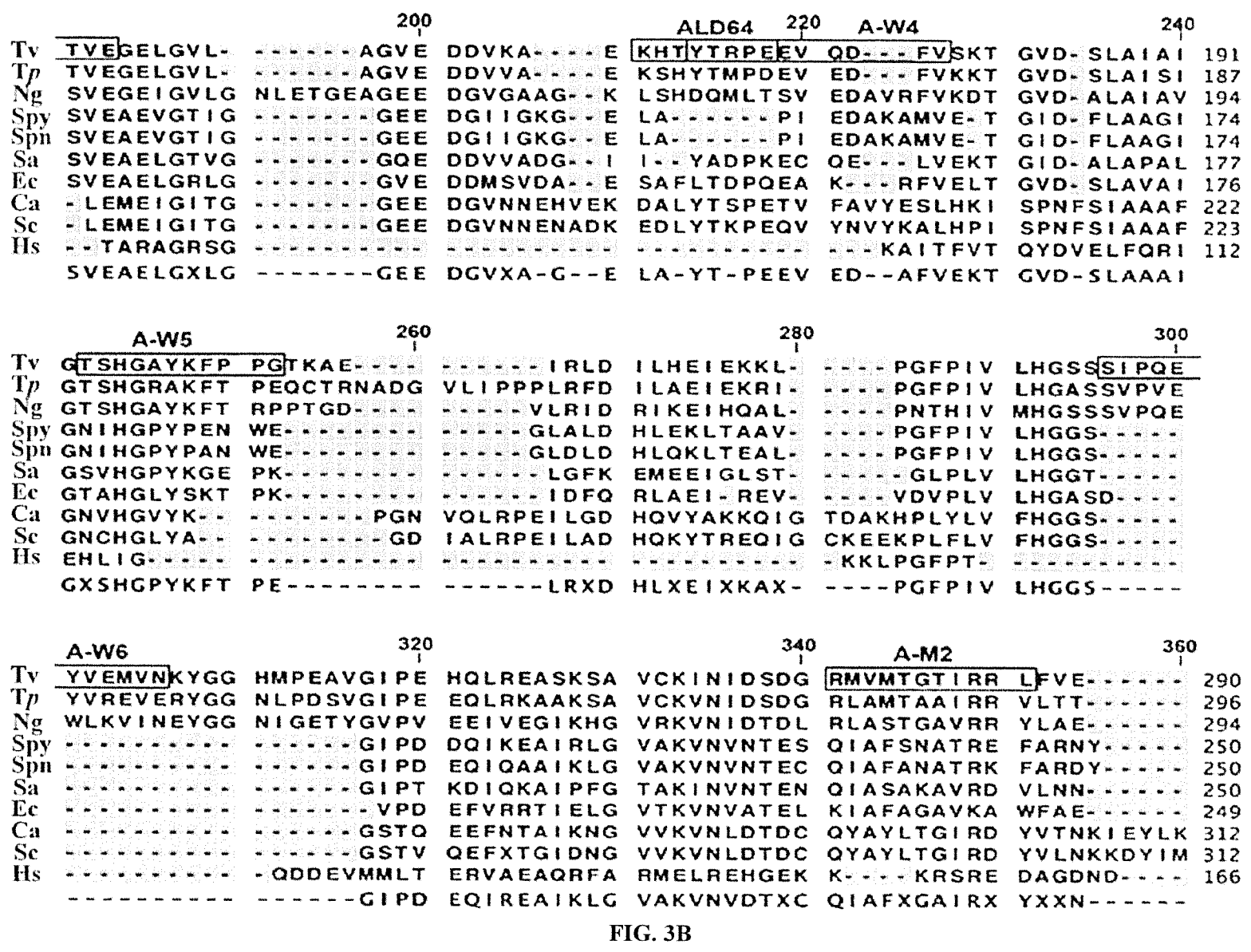

The range of percent identity of these peptide epitopes with selected pathogens and humans is illustrated in the sequence alignment data of FIGS. 3A, 3B, and 3C. Abbreviations F and M refer to female and male patient sera reactive with corresponding epitopes. The plus (+) sign refers to the epitope sequences that are unique to *T. vaginalis*, as evidenced by absence of sequence identity shown in FIGS. 3A, 3B, and 3C.

Sequence Alignment of the *T. vaginalis* Fructose-1,6-Bisphosphate Aldolase (ALD) Protein with ALD Proteins of Other Representative Organisms and *H. sapiens*.

FIGS. 3A, 3B, and 3C shows the amino acid sequence comparison of *T. vaginalis* (Tv, SEQ ID NO:147) ALD with the homolog proteins from *Treponema pallidum* (Tp, SEQ ID NO:148), *Neisseria gonorrhoeae* (Ng, SEQ ID NO:149), *Streptococcus pyogenes* (Spy, SEQ ID NO:150), *Streptococcus pneumoniae* (Spn, SEQ ID NO:151), *Staphylococcus aureus* (Sa, SEQ ID NO:152), *Escherichia coli, Candida albicans, Saccharomyces cerevisiae*, and *Homo sapiens*. The boxed amino acids contained in the *T. vaginalis* sequence are the epitopes presented in Table 2. The order from top to bottom of the sequences is based on from highest to lowest percent identity compared to *T. vaginalis* ALD sequence. All microorganisms represented are pathogens, and 15-mer epitopes and/or SOEs derived from the ALD or other proteins may be used to practice the invention.

TABLE 3

Aldolase percent epitope sequence identity comparisons with bacterial, yeast, and human sequences from alignment shown in FIGS. 3A, 3B, and 3C. ALD12A and ALD64A are MAbs.

| Organism | Epitope | | | | | | | | | | | |
|---|---|---|---|---|---|---|---|---|---|---|---|---|
| | F1 | M1 | F2 | F3 | ALD12A | ALD64A | F4 | F5 | F6 | M2 | F7 M3 | F8 |
| *T. vaginalis* | 100 | 100 | 100 | 100 | 100 | 100 | 100 | 100 | 100 | 100 | 100 | 100 |
| *T. pallidum* | 62.5 | 87 | 72.7 | 100 | 87 | 50 | 72.7 | 63.6 | 54.5 | 54.5 | 75 | 37.5 |
| *N. gonorrhoeae* | 37.5 | 87.5 | 54.5 | 63.6 | 37.5 | 0 | 28.57 | 72.7 | 45.4 | 45.4 | 50 | 0 |
| *S. pyogenes* | 37.5 | 44.4 | 16.7 | 54.5 | 37.5 | 0 | 14.3 | 27.3 | 0 | 9.1 | 25 | 0 |
| *S. pneumoniae* | 37.5 | 44.4 | 25 | 54.5 | 25.00 | 0 | 14.29 | 27.3 | 0 | 9.1 | 25 | 0 |
| *S. aureus* | 50 | 33.3 | 8.3 | 63.6 | 37.5 | 25 | 45.4 | 45.4 | 0 | 9.1 | 75 | 37.5 |
| *E. coli* | 25 | 33.3 | 16.7 | 63.6 | 25 | 25 | 41.7 | 45.4 | 0 | 9.1 | 25 | 12.5 |
| *C. albicans* | 25 | 33.3 | 16.7 | 54.5 | 12.5 | 50 | 35.7 | 36.4 | 0 | 18.2 | 25 | 0 |
| *S. cerevisiae* | 25 | 33.3 | 16.7 | 54.5 | 12.5 | 50 | 35.7 | 27.3 | 0 | 18.2 | 25 | 0 |
| *Homo sapiens* | 0 | 12.5 | 9.1 | 27.3 | 0 | 0 | 0 | 9 | 0 | 9.1 | 12.5 | 0 |

Hydrophobicity and Antigenicity Profiles of the ALD, ENO, and GAP Sequences.

Figure 4A:
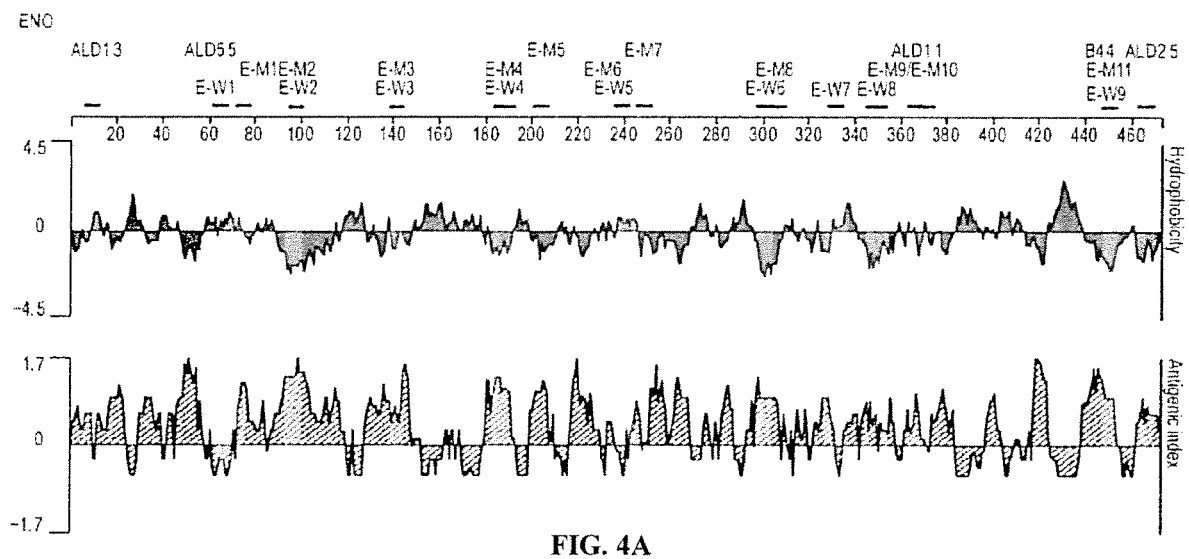
FIG. 4A shows hydrophobicity and antigenicity profile of *T. vaginalis* α-enolase (ENO).
Figure 4B:
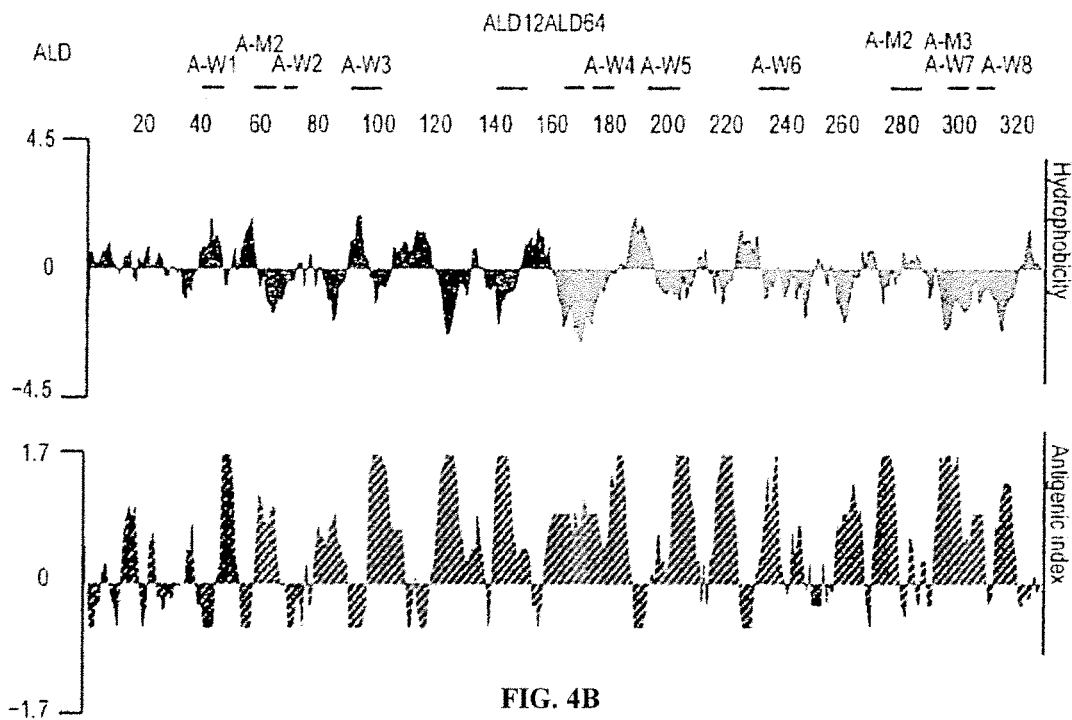
FIG. 4B shows hydrophobicity and antigenicity profile of *T. vaginalis* fructose-1,6-bisphosphate aldolase (ALD).

FIG. 4 presents analyses of hydrophobicity and antigenicity alignments in reference to epitopes along the protein. Of interest is that with few exceptions the epitopes represent hydrophilic regions contained within the protein, perhaps consistent with presentation of amino acids for antibody synthesis and recognition.

Based on the features of the epitopes, 7 epitopes for ALD, 8 for ENO, and 6 for GAP were selected for synthesis of 15-mer peptides encoding in an SOE. The individual amino acid sequence encoding the epitope is bold and underlined.

Example 5. Identification of Diagnostic Immunogenic Epitopes of α-Enolase Unique to *Trichomonas vaginalis*

TABLE 4

Identification of diagnostic immunogenic epitopes of α-enolase protein unique to *T. vaginalis* (Tv). Epitope amino acid sequences unique to the *T. vaginalis* protein are based on percent identity shown in Table 5.

| SEQ ID NO: | no. amino acid sequence | epitope sequence | female patient sera reactivity | male patient sera reactivity | MAb reactivity | unique to Tv |
|---|---|---|---|---|---|---|
| 22 | 6-14 | AIVKECIA | | | ALD13A | + |
| 23 | 64-71 | YLGRVTLA | F1 | | ALD55 | + |
| 24 | 70-77 | LAARSSAP | | M1 | | + |
| 25 | 94-101 | DKARYGGK | F2 | M2 | | |

TABLE 4-continued

Identification of diagnostic immunogenic epitopes of α-enolase protein unique to T. vaginalis (Tv). Epitope amino acid sequences unique to the T. vaginalis protein are based on percent identity shown in Table 5.

| SEQ ID NO: | no. amino acid sequence | epitope sequence | female patient sera reactivity | male patient sera reactivity | MAb reactivity | unique to Tv |
|---|---|---|---|---|---|---|
| 26 | 139-146 | TVLKKNIG | F3 | M3 | | + |
| 27 | 184-194 | VPKKFKLPSPF | F4 | M4 | | + |
| 28 | 238-246 | GGLLVKKY | F5 | | | + |
| 29 | 245-252 | KYGLSAKN | | M7 | | + |
| 30 | 298-305 | FYDEEKKL | | M8 | | + |
| 31 | 328-338 | KKHPAIVSIED | F6 | | | |
| 32 | 343-362 | ENWTKLNARLG | F7 | | | |
| 33 | 364-371 | DDLYTTNP | | | ALD11A | |
| 34 | 448-455 | ERIQKYTR | F9 | M11 | B44 | |
| 35 | 463-471 | LKEHDMLA | | | ALD25 | + |

TABLE 5

The extent of sequence identity of the *T. vaginalis* α-enolase with the protein sequences of bacteria, yeasts, and human. The epitopes are indicated by F1 through F9, M1 through M7, and the MAbs ALD13A/B, ALD55, ALD11A, and ALD25 are as listed in the Table.

| | Epitope | | | | | | |
|---|---|---|---|---|---|---|---|
| Organism | ALD13A | F1 ALD55 | M1 | F2 M2 | F3 M3 | F4 M4 | F5 |
| *T. vaginalis* | 100 | 100 | 100 | 100 | 100 | 100 | 100 |
| *T. pallidum* | 0.00 | 0.00 | 25 | 71.4 | 37.5 | 27.3 | 37.5 |
| *N. gonorrhoeae* | 0 | 0 | 25 | 71.4 | 50 | 27.3 | 25 |
| *C. trachomatis* | 0 | 0 | 12.5 | 57.1 | 37.5 | 27.3 | 12.5 |
| *S. pyogenes* | 0 | 0 | 25 | 71.4 | 37.5 | 27.3 | 12.5 |
| *S. pneumoniae* | 0 | 0 | 25 | 85.7 | 37.5 | 27.3 | 12.5 |
| *S. aureus* | 0 | 0 | 25 | 71.4 | 37.5 | 27.3 | 25 |
| *E. coli* | 0 | 0 | 25 | 57.1 | 37.5 | 36.4 | 25 |
| *C. albicans* | 0 | 12.5 | 50 | 42.8 | 37.5 | 54.5 | 50 |
| *S. cerevisiae* | 0 | 0 | 37.5 | 42.8 | 37.5 | 36.4 | 37.5 |
| *Homo sapiens* | 0 | 12.5 | 37.5 | 71.4 | 37.5 | 27.3 | 37.5 |

| | Epitope | | | | | | |
|---|---|---|---|---|---|---|---|
| Organism | M5 | F6 M6 | F7 | F8 | ALD11A | F9 M7 B44 | ALD25 |
| *T. vaginalis* | 100 | 100 | 100 | 100 | 100 | 100 | 100 |
| *T. pallidum* | 0 | 25 | 63.6 | 27.3 | 50 | 37.5 | 5.5 |
| *N. gonorrhoeae* | 12.5 | 25 | 54.5 | 45.4 | 75 | 37 | 10.5 |
| *C. trachomatis* | 0 | 37.5 | 54.5 | 45.4 | 62.5 | 75 | 0 |
| *S. pyogenes* | 12.5 | 37.5 | 54.5 | 45.4 | 50 | 50 | 10.5 |
| *S. pneumoniae* | 12.5 | 37.5 | 54.5 | 45.4 | 50 | 50 | 10.5 |

TABLE 5-continued

The extent of sequence identity of the *T. vaginalis* α-enolase with the protein sequences of bacteria, yeasts, and human. The epitopes are indicated by F1 through F9, M1 through M7, and the MAbs ALD13A/B, ALD55, ALD11A, and ALD25 are as listed in the Table.

| | | | | | | | |
|---|---|---|---|---|---|---|---|
| S. aureus | 12.5 | 25 | 54.5 | 36.4 | 62.5 | 50 | 10.5 |
| E. coli | 25 | 25 | 72.7 | 18.3 | 62.5 | 37.5 | 10 |
| C. albicans | 75 | 37.5 | 63.6 | 27.3 | 75 | 37.5 | 6.3 |
| S. cerevisiae | 62.5 | 25 | 73.7 | 27.3 | 75 | 37.5 | 6.3 |
| Homo sapiens | 62.5 | 37.5 | 54.5 | 36.4 | 75 | 50 | 6.3 |

Abbreviations:
F, female antibody reacting with epitope;
M, male antibody reacting with epitope;
ALD refers to MAbs.

TABLE 6

Identification of epitopes of *Trichomonas vaginalis* (Tv) α-enolase reactive with human sera.[1]

| | spots number on membrane | amino acid sequence | epitope sequence | female patient sera | pooled reactive male sera | MAb reactions | unique to Tv | % identity with human sequence |
|---|---|---|---|---|---|---|---|---|
| SEQ ID NO: 22 | 2.3 | 6-14 | AIVKECIA | | | ALD13A | + | |
| SEQ ID NO: 23 | 21-23 | 64-71 | YLGRVTLA | F1 | | ALD55 | + | |
| SEQ ID NO: 24 | 23-25 | 70-77 | LAARSSAP | | M1 | | + | |
| SEQ ID NO: 25 | 31-33 | 94-101 | DKARYGGK | F2 | M2 | | | 71% |
| SEQ ID NO: 26 | 46-47 | 139-146 | TVLKKNIG | F3 | M3 | | + | |
| SEQ ID NO: 27 | 62 | 184-194 | VPKKFKLPSPF | F4 | M4 | | + | |
| SEQ ID NO: 135 | 67 | 199-209 | NGGKHAGGNLK | | M5 | | | |
| SEQ ID NO: 136 | 76 | 226-236 | OLRMVAEVYQK | | M6 | | | |
| SEQ ID NO: 28 | 79-81 | 238-746 | GGLLVKKY | F5 | | | + | |
| SEQ ID NO: 29 | 81-82 | 245-252 | KYGLSAKN | | M7 | | | 62.5% |
| SEQ ID NO: 30 | 99-100 | 298-305 | FYDEEKKL | | M8 | | + | |
| SEQ ID NO: 31 | 110 | 328-338 | KKHPAIVSIED | F6 | | | + | |
| SEQ ID NO: 32 | 115-118 | 343-362 | ENWTKLNARLG | F7 | | | + | |
| SEQ ID NO: 137 | 117-118 | 352-359 | NARLGQRV | | M9 | | | |
| SEQ ID NO: 33 | 121-123 | 364-371 | DDLYTTNP | | | ALD11A | | 75% |
| SEQ ID NO: 138 | 123-124 | 370-377 | NPITIKKG | F8 | M10 | | | |
| SEQ ID NO: 34 | 149-151 | 448-455 | ERIQKYTR | F9 | M11 | B44 | + | |
| SEQ ID NO: 35 | 154-155 | 463-471 | LKEHDMLA | | | ALD25 | + | |

Example 6. Identification of Diagnostic Immunogenic Epitopes of GAPDH Unique to *Trichomonas vaginalis*, and Diagnostic Epitopes Identical to or with High Sequence Identity to *Tritrichomonas suis* (Synonym with *T. foetus* Bovine, *T. foetus* Cat, and *T. mobilensis*)

TABLE 7

Identification of diagnostic immunogenic epitopes of GAPDH protein unique to *T. vaginalis*.

| | no. amino acid sequence | epitope sequence | female patient sera reactivity | male patient sera reactivity | MAb reactivity | unique to Tv |
|---|---|---|---|---|---|---|
| SEQ ID NO: 36 | 13-17 | LYPKD | | M1 | | + |
| SEQ ID NO: 37 | 34-44 | YLLKYDTAHRA | F1 | | ALD32C | + |
| SEQ ID NO: 38 | 58-68 | FTVGEGADKWV | | M2 | | + |
| SEQ ID NO: 39 | 70-77 | KSIGGRLG | F2 | | ALD30A | + |
| SEQ ID NO: 40 | 94-101 | STGIFRTK | F3 | | | + |
| SEQ ID NO: 41 | 106-113 | AEGKIKKD | F4 | | | + |
| SEQ ID NO: 42 | 118-125 | HLVSGAKK | F5 | M4 | | |
| SEQ ID NO: 43 | 157-161 | SNASC | | M5 | | |
| SEQ ID NO: 44 | 175-182 | NAEGIRNG | F6 | | | + |
| SEQ ID NO: 45 | 205-912 | RRARAAGM | F7 | | B43 | |
| SEQ ID NO: 46 | 217-274 | TSTGAAIA | F8 | | | |
| SEQ ID NO: 47 | 229-233 | CHGLP | | M6 | | |
| SEQ ID NO: 48 | 250-260 | SLVDLTVNVNA | F9 | | | |
| SEQ ID NO: 49 | 292-299 | VSSDIIGC | | M7 | | |
| SEQ ID NO: 50 | 298-305 | GCQYSSIV | | M8 | | |
| SEQ ID NO: 51 | 301-311 | YSSIVDALSTK | F10 | | | |
| SEQ ID NO: 52 | 325-335 | VSWYDNEWMY | F11 | M9 | | |
| SEQ ID NO: 53 | 337-341 | CRCAD | | M10 | | |

TABLE 8

The extent of sequence identity of the *T. vaginalis* GAPDH with the protein sequences of bacteria, yeasts, and human from alignment shown in FIG. 3.

| | Epitope | | | | | | | | | | | | | | | | | | | | |
|---|---|---|---|---|---|---|---|---|---|---|---|---|---|---|---|---|---|---|---|---|---|
| Organism | M1 | F1 ALD32 | M2 | F2 ALD30 | M3 | F3 | F4 | F5 M4 | M5 | F6 | F7 B43 | F8 | M6 | F9 | M7 | M8 | F10 | F11 M9 | M10 | Overall |
| *T. vaginalis* | 100 | 100 | 100 | 100 | 100 | 100 | 100 | 100 | 100 | 100 | 100 | 100 | 100 | 100 | 100 | 100 | 100 | 100 | 100 | 100 |
| *T. suis* | 80 | 55 | 73 | 63 | 100 | 75 | 38 | 75 | 100 | 75 | 88 | 100 | 20 | 64 | 88 | 63 | 73 | 100 | 100 | 70 |
| *C. albicans* | 0 | 45 | 9 | 25 | 40 | 50 | 13 | 56 | 100 | 50 | 38 | 75 | 20 | 55 | 50 | 63 | 45 | 64 | 40 | 40 |
| *S. cerevisiae* | 0 | 45 | 9 | 13 | 60 | 50 | 13 | 56 | 100 | 63 | 38 | 75 | 20 | 61 | 63 | 50 | 45 | 64 | 40 | 39 |
| *C. trachomatis* | 0 | 55 | 0 | 0 | 60 | 50 | 13 | 67 | 100 | 50 | 38 | 75 | 20 | 55 | 88 | 75 | 55 | 55 | 40 | 38 |
| *T. pallidum* | 40 | 45 | 9 | 44 | 100 | 38 | 0 | 56 | 100 | 38 | 50 | 63 | 0 | 45 | 50 | 63 | 55 | 82 | 40 | 40 |
| *N. gonorrhoeae* | 0 | 45 | 9 | 13 | 60 | 38 | 13 | 78 | 100 | 38 | 50 | 75 | 20 | 45 | 38 | 13 | 45 | 64 | 20 | 41 |
| *S. pneumoniae* | 0 | 55 | 9 | 25 | 40 | 38 | 25 | 67 | 80 | 38 | 63 | 75 | 20 | 18 | 75 | 38 | 55 | 73 | 0 | 40 |
| *S. pyogenes* | 0 | 55 | 9 | 25 | 20 | 38 | 25 | 67 | 80 | 63 | 63 | 75 | 20 | 27 | 75 | 38 | 55 | 73 | 0 | 40 |
| *S. aureus* | 0 | 45 | 0 | 25 | 60 | 38 | 13 | 56 | 100 | 75 | 50 | 88 | 20 | 55 | 38 | 25 | 55 | 73 | 40 | 40 |

TABLE 8-continued

The extent of sequence identity of the *T. vaginalis* GAPDH with the protein sequences of bacteria, yeasts, and human from alignment shown in FIG. 3.

| | Epitope | | | | | | | | | | | | | | | | | | | |
|---|---|---|---|---|---|---|---|---|---|---|---|---|---|---|---|---|---|---|---|---|
| Organism | M1 | F1 ALD32 | M2 | F2 ALD30 | M3 | F3 | F4 | F5 M4 | M5 | F6 | F7 B43 | F8 | M6 | F9 | M7 | M8 | F10 | F11 M9 | M10 | Overall |
| *E. coli* | 0 | 55 | 9 | 13 | 40 | 38 | 0 | 56 | 100 | 50 | 38 | 75 | 20 | 55 | 50 | 25 | 27 | 64 | 20 | 40 |
| *Homo sapiens* | 0 | 45 | 0 | 0 | 60 | 38 | 0 | 33 | 36 | 50 | 38 | 75 | 20 | 45 | 50 | 50 | 45 | 64 | 40 | 30 |

TABLE 9

Identification of epitopes of *Trichomonas vaginalis* (Tv) GAPDH reactive with human sera and MAbs and with identity to human and *T. suis*.

| | SPOTS peptide no. | amino acid sequence | epitope sequence | female patient serum | pooled reactive male sera | MAb reactions | unique Tv epitope for diagnosis | % identity with human peptide sequence | % identity with *T. suis* peptide sequence |
|---|---|---|---|---|---|---|---|---|---|
| SEQ ID NO: 36 | 3-5 | 13-17 | LYPKD | | M1 | | + | | 80 |
| SEQ ID NO: 37 | 12 | 34-44 | YLLKYDTAHRA | F1 | | ALD32C | + | | 55 |
| SEQ ID NO: 38 | 20 | 58-68 | FTVGEGADKWV | | M2 | | + | | 73 |
| SEQ ID NO: 39 | 73-74 | 70-77 | KSIGGRLG | F2 | | ALD30A | + | | 63 |
| SEQ ID NO: 139 | 25-27 | 79-83 | SQLPW | | M3 | | | 60 | 100 |
| SEQ ID NO: 40 | 31-33 | 94-101 | STGIERTK | F3 | | | + | | 75 |
| SEQ ID NO: 41 | 35-37 | 106-113 | AEGKIKKD | F4 | | | + | | 25 |
| SEQ ID NO: 42 | 39-41 | 118-125 | HLVSGAKK | F5 | M4 | | | | 75 |
| SEQ ID NO: 43 | 51-53 | 157-161 | SNASC | | M5 | | | 50 | 100 |
| SEQ ID NO: 44 | 57-59 | 175-182 | NAEGIRNG | F6 | | | | 50 | 75 |
| SEQ ID NO: 45 | 67-69 | 205-212 | RRARAAGM | F7 | | B43 | | | 88 |
| SEQ ID NO: 46 | 72-74 | 217-224 | TSTGAAIA | F8 | | | | 75 | 100 |
| SEQ ID NO: 47 | 75-77 | 229-233 | CHGLP | | M6 | | + | | 20 |
| SEQ ID NO: 48 | 84 | 250-260 | SLVDLTVNVNA | F9 | | | + | | 64 |
| SEQ ID NO: 49 | 97-98 | 292-299 | VSSDIIGC | | M7 | | | 50 | 88 |
| SEQ ID NO: 50 | 99-100 | 298-305 | GCQYSSIV | | M8 | | | 50 | 63 |
| SEQ ID NO: 51 | 101 | 301-311 | YSSIVDALSTK | F10 | | | + | | 73 |
| SEQ ID NO: 52 | 109 | 325-335 | VLSWYDNEWMY | F11 | M9 | | | 64 | 100 |
| SEQ ID NO: 53 | 111-113 | 337-341 | CRCAD | | M10 | | + | | 100 |

TABLE 10

Identification of T. vaginalis (Tv) GAPDH peptide epitopes that have high sequence identity to GAPDH of and are diagnostic for Tritrichomonas suis (Ts). Only peptide epitopes of T. vaginalis with ≥50% identity were selected.

|  | no. amino acid sequence | (Tv) epitope sequence | SEQ ID NO: | (Ts) epitope sequence | Ts percent identity |
|---|---|---|---|---|---|
| SEQ ID NO: 36 | 13-17 | LYPKD | 54 | LYPK<u>E</u> | 80 |
| SEQ ID NO: 37 | 34-44 | YLLKYDTAHRA | 55 | HLL<u>N</u>YD<u>S</u>AH<u>QR</u> | 55 |
| SEQ ID NO: 38 | 58-68 | FTVGEGADKWV | 56 | F<u>E</u>VG<u>TG</u>SDKWV | 73 |
| SEQ ID NO: 39 | 70-77 | KSIGGRLG | 57 | K<u>NL</u>TGRLG | 62.5 |
| SEQ ID NO: 40 | 94-101 | STGIFRTK | 58 | STG<u>L</u>FRT<u>H</u> | 75 |
| SEQ ID NO: 41 | 118-125 | HLVSGAKK | 59 | HL<u>LA</u>GAKK | 75 |
| SEQ ID NO: 43 | 157-161 | SNASC | 60 | SNASC | 100 |
| SEQ ID NO: 140 | 172-179 | TLNNAFGI | 61 | <u>V</u>LN<u>DT</u>EGI | 57 |
| SEQ ID NO: 141 | 202-212 | KDLRRARAAGM | 62 | RRARAAGM | 100 |
| SEQ ID NO: 142 | 247-257 | ITGSLVDLTVN | 63 | ITGSLVD<u>I</u>TVN | 91 |
| SEQ ID NO: 51 | 301-311 | YSSIVDALSTKV | 64 | <u>H</u>SSIVD<u>S</u>LST<u>M</u>V | 75 |
| SEQ ID NO: 143 | 322-329 | LVKVLSWY | 65 | LVKVLSWY | 100 |

Additional noteworthy evidence of the GAPDH crossreactivity between T. vaginalis and T. suis (T. foetus) is evidenced by data obtained by detection on nitrocellulose of the T. foetus GAPDH after SDS-PAGE and immunoblotting of total proteins of different T. foetus isolates. The MAbs generated to the T. vaginalis GAPDH (Table 1) were used as probes to detect the T. foetus protein.

Example 7. Identification of Diagnostic Immunogenic Epitopes of α-Actinin Unique to Trichomonas vaginalis

TABLE 11

Identification of diagnostic immunogenic epitopes of α-actinin protein unique to T. vaginalis (Tv)

|  | SPOTS numbers | amino acid sequence | epitope name | sequence | woman patient serum | reactive men serum | MAb | unique to Tv |
|---|---|---|---|---|---|---|---|---|
| SEQ ID NO: 66 | 2 | 4-14 | ACT1 | RREGLLDDAWE | F1 |  |  | + |
| SEQ ID NO: 67 | 11-12 | 34-41 | ACT2 | IQFETIET | F2 |  |  | + |
| SEQ ID NO: 68 | 21-23 | 67-71 | ACT3 | KQPKM | F3 |  |  | + |
| SEQ ID NO: 69 | 50 | 148-158 | ACT4 | YEHVAVNNFTT | F4 |  |  | + |
| SEQ ID NO: 70 | 69 | 205-215 | ACT5 | YVYLDPEDVID | F5 |  |  | + |
| SEQ ID NO: 71 | 80-82 | 244-248 | ACT6 | ADKIK | F6 |  |  | + |
| SEQ ID NO: 72 | 97-99 | 295-302 | ACT7 | RGKLASVI | F7 |  |  | + |
| SEQ ID NO: 73 | 111-112 | 334-341 | ACT8 | NRPIPEIP | F8 |  |  | + |
| SEQ ID NO: 74 | 152-153 | 457-464 | ACT9 | HHSQLITY | F9 | M1 |  | + |
| SEQ ID NO: 75 | 165-166 | 496-503 | ACT10 | YDEAIAFK | F10 | M2 |  | + |
| SEQ ID NO: 76 | 214-216 | 646-650 | ACT11 | KLNYK | F11 | M3 |  | + |

TABLE 11-continued

Identification of diagnostic immunogenic
epitopes of α-actinin protein unique to
T. vaginalis (Tv)

| | SPOTS numbers | amino acid sequence | epitope name | sequence | woman patient serum | reactive men serum | MAb | unique to Tv |
|---|---|---|---|---|---|---|---|---|
| SEQ ID NO: 77 | 215-217 | 649-653 | ACT12 | YKVTY | F12 | M4 | HA423 | + |
| SEQ ID NO: 78 | 268-270 | 808-812 | ACT13 | KYFDK | F13 | M5 | | + |

TABLE 12

The extent of sequence identity of the *T. vaginalis* α-actinin with the protein sequences of bacteria, yeasts, and human.

| Epitope | T. suis | C. albicans | S. cerevisiae | HuACTN1 |
|---|---|---|---|---|
| ACT-F1 (W1) | 9 | 9 | 11 | 21 |
| ACT-F2 (W2) | 0 | 0 | 0 | 50 |
| ACT-F3 (W3) | 0 | 20 | 20 | 40 |
| ACT-F4 (W4) | 9 | 18 | 9 | 46 |
| ACT-F5 (W5) | 0 | 18 | 0 | 36 |
| ACT-F6 (W6) | 14 | 14 | 20 | 40 |
| ACT-F7 (W7) | 0 | 0 | 13 | 25 |
| ACT-F8 (W8) | 0 | 0 | 25 | 38 |
| ACT-F1/M1 (W9/M1) | 11 | 22 | 11 | 13 |
| ACT-F10/M2 (W10/M2) | 0 | 0 | 13 | 13 |
| ACT-F11/M3 (W11/M3) | 20 | 0 | 20 | 20 |
| ACT-F12/M4 (W12/M4/HA423) | 20 | 20 | 20 | 0 |
| ACT-F13/M5 (W13/M5) | 0 | 20 | 0 | 40 |

Note absence of sequence identity with all proteins for representative organisms shown in Table 12. There is no identity of epitopes with other proteins of bacteria, fungi, protists, and humans in databanks.

Example 8. Synthesis of 15-Mer Peptide Epitopes of ALD, ENO, GAP, and ACT Unique to *Trichomonas vaginalis* to Demonstrate Immunoreactivity with Women and Men Sera Based examination of the sequences with algorithms for hydrophobicity and antigenicity, we then selected 7 epitopes for ALD, 8 for ENO, and 6 for GAP, and the 13 for ACT (taken from Table 11) for synthesis of 15-mer peptides encoding the epitopes. Table 13 shows the epitopes and includes 3 for ACT to which data are presented below. The individual amino acid sequence encoding the epitope within each 15-mer peptide is shown in bold and underlined.

Peptide epitopes from each protein were selected based on low percent identity and solubility. The 15-mer amino acid sequences were sent to Sigma-Aldrich (The Woodlands, Tex.) and synthesized using their Custom PepScreen Peptide service. Each individual 15-mer peptide contained was acetylated at the amino-terminus and was amidylated at the carboxy-terminus. Each 15-mer peptide was screened by mass spectrometry to determine yield and purity of each product. Peptide epitopes were received with a pass/fail designation and the amount provided. Three α-actinin 15-mer peptides of ACT were used as positive controls in the experiments presented below. These peptides were designated ACT2, ACT3, and ACT1 and corresponded to the amino acid sequences

```
                                        (SEQ ID NO: 101)
AQPLYDEAIAFKEEV, (SEQ ID NO: 102)
FKDTFKYFDKDKSNS
and (SEQ ID NO: 100)
SVNRHHSQLITYIKH,
``` respectively (shown in Table 13).

TABLE 13

List of synthetic 15-mer peptides of representative epitopes of ALD, ENO, GAP, and ACT for reactivity with immunoreactive women and men sera.

| | women/men epitope designation | peptide name | amino acid numbers | amino acid sequence |
|---|---|---|---|---|
| SEQ ID NO: 79 | A-W1 | ALD1 | 36-50 | EQLQAIITASVKTES |
| SEQ ID NO: 80 | A-ALD12 | ALD2 | 138-152 | EAHSRPDYVTVEGEL |
| SEQ ID NO: 81 | A-ALD64 | ALD3 | 159-173 | EDDVKAEKHTYTRPE |
| SEQ ID NO: 82 | A-W4 | ALD4 | 167-181 | HTYTRPEEVQDFVSK |
| SEQ ID NO: 83 | A-W6 | ALD5 | 230-244 | SSSIPQEYVEMVNKY |
| SEQ ID NO: 84 | A-M2 | ALD6 | 275-289 | DGRMVMTGTIRRLFV |
| SEQ ID NO: 85 | A-W8 | ALD7 | 301-315 | LGEARTKLTEMYMRK |
| SEQ ID NO: 86 | E-W1 | ENO1 | 57-71 | VKYLGRVTLAARSSA |

TABLE 13-continued

List of synthetic 15-mer peptides of representative epitopes of ALD, ENO, GAP, and ACT for reactivity with immunoreactive women and men sera.

| | women/men epitope designation | peptide name | amino acid numbers | amino acid sequence |
|---|---|---|---|---|
| SEQ ID NO: 87 | E-M1 | ENO2 | 70-84 | VTLAARSSAPSGAST |
| SEQ ID NO: 88 | E-W3,E-M3 | ENO3 | 136-150 | TDGTVLKKNIGGNAC |
| SEQ ID NO: 89 | E-F4/M4 | ENO4 | 182-196 | DKVPKKFKLPSPFFN |
| SEQ ID NO: 90 | E-W5 | ENO5 | 236-250 | KLGGLLVKKYGLSAK |
| SEQ ID NO: 91 | E-M8 | ENO6 | 295-309 | SSEFYDEEKKLYEVE |
| SEQ ID NO: 92 | E-W7/M9 | ENO7 | 344-358 | DYENWTKLNARLGQR |
| SEQ ID NO: 93 | E-W8,E-M10 | ENO8 | 366-380 | LYTTNPITIKKGLEG |
| SEQ ID NO: 94 | G-M1 | GAP1 | 8-97 | RACRKLYPKDIQVVA |
| SEQ ID NO: 95 | G-M2 | GAP2 | 56-70 | QEFTVGEGADKWVVK |
| SEQ ID NO: 96 | G-W2 | GAP3 | 67-81 | WVVKSIGGRLGPSQL |
| SEQ ID NO: 97 | G-W4 | GAP4 | 104-118 | KDAEGKIKKDDGYDGH |
| SEQ ID NO: 98 | G-M6 | GAP5 | 224-238 | ALPKVCHGLPPKSLD |
| SEQ ID NO: 99 | G-M10 | GAP6 | 332-346 | EWMYSCRCADIFHRL |
| SEQ ID NO: 100 | ACT-W9,M1 | ACT1 | 463-467 | SVNRHHSQLITYIKH |
| SEQ ID NO: 101 | ACT-W10,M2 | ACT2 | 492-506 | AQPLYDEAIAFKEEV |
| SEQ ID NO: 102 | ACT-W13,M5 | ACT3 | 803-817 | FKDTFKYFDKDKSNS |

Approximately 1 μg of individual and/or a combination of synthetic peptides were dot-blotted onto a nitrocellulose membrane and allowed to air dry for 30 min at 37° C. These dot-blots were fit into individual wells of a 96-well microtiter ELISA plate. Then, 100 μl of 2% ELISA-grade BSA (Sigma-Aldrich, St. Louis, Mo.) in PBS (eBSA-PBS), pH 7.4, was added and incubated for 2 hours at RT, after which 5 μl of a 1:1 dilution (v/v) of *T. vaginalis* negative- and positive-control women or men sera in PBS, pH 7.4, was added and incubated for 30 min at RT. The remainder of the procedure is as detailed above. Densitometric scans were produced using the ImageJ software (rsbweb.nih.gov/ij).

FIGS. 5A, 5B, 5C, and 5D present results from representative dot-blot reactions using positive control sera of women and men of 15-mer peptides for ALD (1a and 1b), ENO (2a and 2b), GAP (3a and 3b), and ACT (4a and 4b) as a positive control (XX). Reactivity was detected for each 15-mer peptide, albeit at different levels of spot intensities. No peptides were detectable using negative control sera for both women and men that were determined to be unreactive with the full-length proteins. These data suggest that some peptide-epitopes may be used as serodiagnostic targets.

Figure 6A:
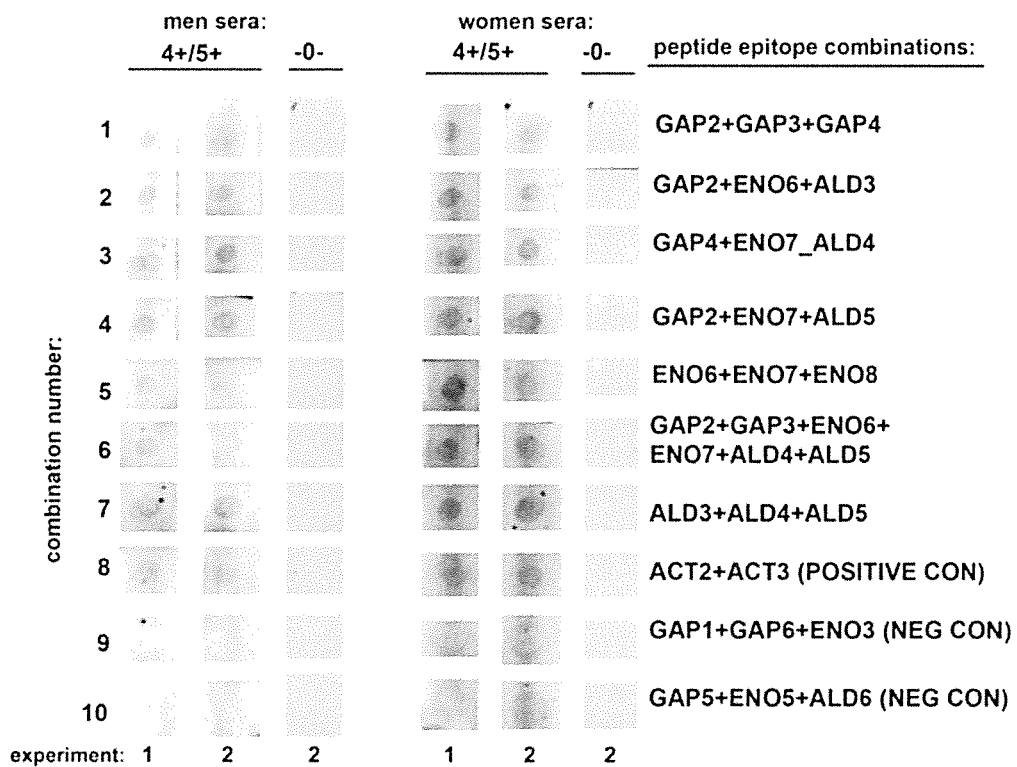
FIG. 6A shows representative duplicate dot blots of combinations of 15-mer epitopes.
Figure 6B:
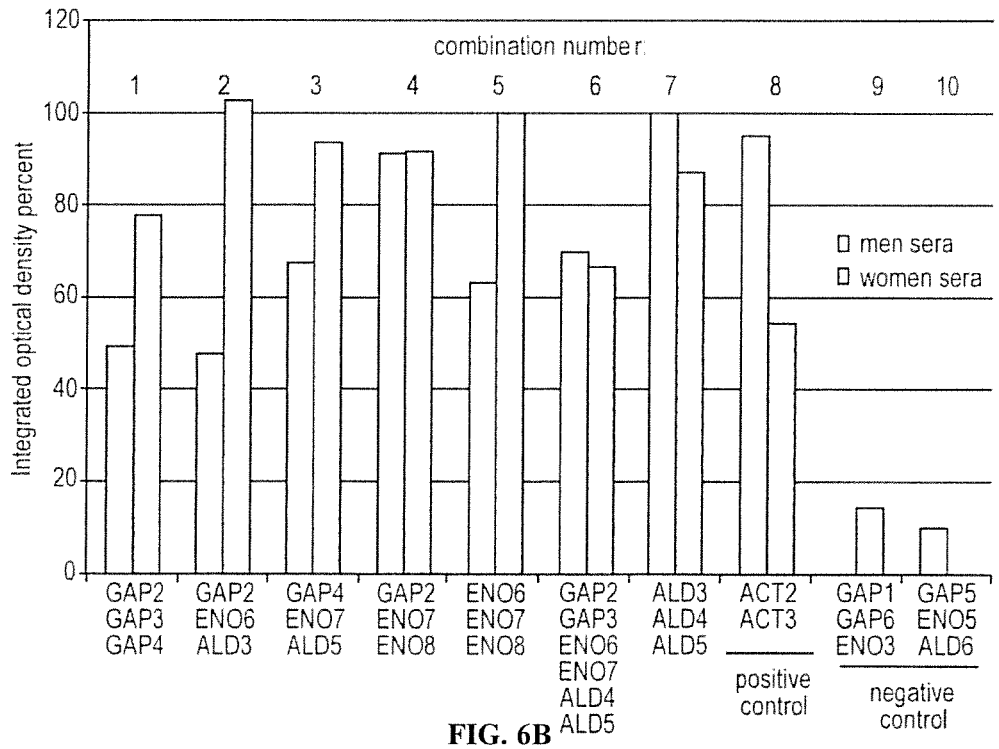
FIG. 6B shows densitometric scans of reactive dot blots from FIG. 4A.

We next performed dot-blots (FIG. 6A) using random combinations of the 15-mer peptides to determine whether an increased extent of reactivity was seen for women and men sera. We further wanted combinations of peptides that might give equal reactivity for both sera. FIG. 6B presents in duplicate the intensity of signal for each combination with the positive control women and men sera (labeled 4+/5+), and no detection of the peptide cocktails was evident with negative control sera (labeled -0-). Densitometric scan (bars 1 through 7) revealed overall better extent of reactions with combination of peptides compared to the individual peptides for both women and men sera (data not shown). The combined peptides ACT2 and ACT3 (bars 8) served as positive controls with known sera of men and women reactive with α-actinin, and the pooled peptides GAP1, GAP6 and ENO3 (bars 9) as well as GAP5, ENO5, and ALD6 (bars 10) showed no reactivity with negative control sera of both women and men sera.

Example 8. Identification of Immunogenic Epitopes of α-Enolase and GAPDH with High Sequence Identity to Human Protein Sequences From Tables 6 and 9 it was possible to identify three epitopes of α-enolase and one epitope of GAPDH with 62.5% to 78% identity to the human peptide sequences, as illustrated in Table 14. The peptide sequences were considered high identity if there was a difference in sequence by only two to three amino acids in an eight to nine linear amino acid sequence.

TABLE 14

Identification of *Trichomonas vaginalis* (Tv) peptide epitopes with high sequence identity to human (Hu) protein epitopes and with possible immune crossreactivity.

| | protein | amino acid sequence | epitope sequence | | female patient sera reaction | male patient sera reaction | MAb reactivity | identity (%) |
|---|---|---|---|---|---|---|---|---|
| SEQ ID NO: 25 | ENO | 94-101 | (Tv) | DKARYGGK | + | + | | 78 |
| SEQ ID NO: 103 | | | (Hu) | DKQRYLGK | | | | |
| SEQ ID NO: 29 | ENO | 245-252 | (Tv) | KYGLSAKN | | + | | 62.5 |
| SEQ ID NO: 104 | | | (Hu) | KYGKDATN | | | | |
| SEQ ID NO: 4 | ENO | 364-371 | (Tv) | DDLYTTNP | | | + | 75 |
| SEQ ID NO: 105 | | | (Hu) | DDLTVTNP | | | | |
| SEQ ID NO: 144 | GAP | 322-329 | (Tv) | LVKVLSWY | + | + | | 62.5 |
| SEQ ID NO: 106 | | | (Hu) | FVKLISWY | | | | |

Example 9. Production of Recombinant Protein Encoding Sequential Epitope Sequences of Aldolase, GAPDH, α-Enolase, and α-Actinin Separated by Amino Acid Spacers for Use in Serodiagnosis In this example, the epitopes identified in Tables 2-11 that are immunoreactive with seropositive sera of women and men for the proteins aldolase, GAPDH, α-enolase, and α-actinin are encoded within a plasmid construct so that the individual epitopes are within 15-mer peptides of the trichomonad protein. The epitopes may be in any random order so that, for example, the sequence of epitopes may include one for aldolase followed by one for α-actinin followed by one for α-enolase followed by one for aldolase, etcetera. Further, the number of epitopes may be just one each representative of each protein or as many as deemed necessary for each protein for optimal antibody detection in a serodiagnostic. The plasmid construct is then expressed in recombinant *E. coli*, and a recombinant protein is then made upon induction. This type of recombinant protein containing a series or an array of epitopes is referred to here as a String of Pearls (SOP) where each "pearl" is representative of the amino acid sequence within which is found an epitope as described. This recombinant protein can also be referred to interchangeably as a SOE or rSOE.

Figures 7A, 7B:
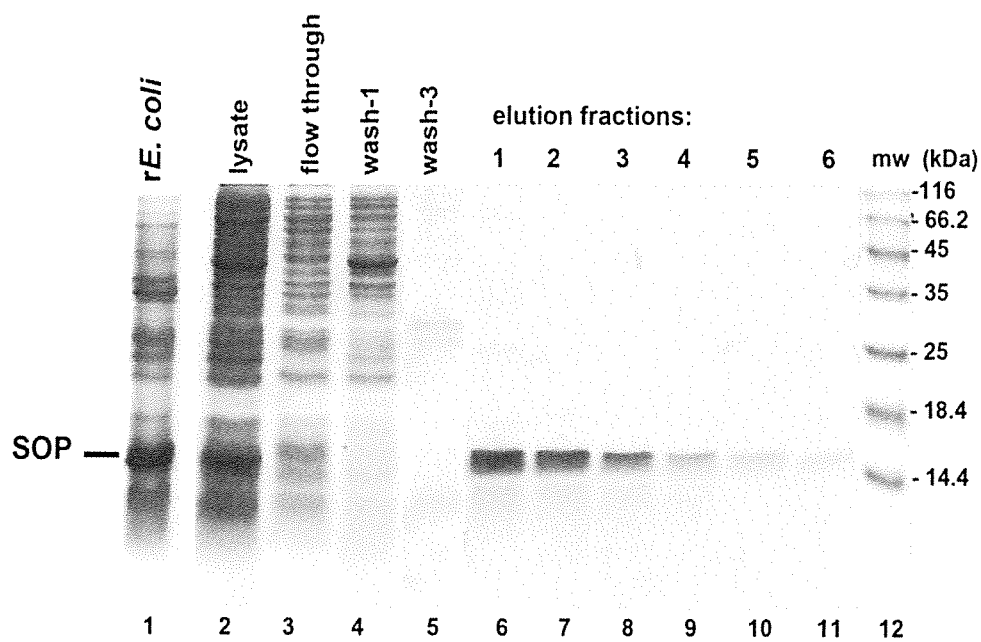
FIG. 7A shows the 111 amino acid sequence of an rSOE encoding 15-mer epitopes of GAP (GAPDH), ENO (enolase) and ALD (aldolase) proteins from *T. vaginalis*. The sequence is that of SEQ ID NO:145.
FIG. 7B shows SDS-PAGE and Coomassie-brilliant blue stained gels of recombinant *E. coli*, rSOE lysate, flow-through, washes and elution fractions.

FIG. 7A presents a simple example of an SOP encoding sequentially two epitopes of GAPDH, two epitopes of α-enolase, and two epitopes of aldolase. The sequences of these individual epitopes and 15-mer epitopes are among those listed in Table 13 above. The SOP sequence identity is also provided in SEQ ID NO:145. This and other recombinant SOP arrays of epitopes of the *T. vaginalis* proteins aldolase, GAPDH, α-enolase, and α-actinin purified similarly can then be immobilized on surfaces for probing and detection by immunoreactive sera of women and men. FIG. 7B shows purification of an SOP, with lysate, flow-through, washes, and elution fractions in SDS-PAGE gel with Coomassie-brilliant blue stain.

The SOP encoding for an array of six 15-mer amino acid sequences, two each of which contained epitopes for ALD, ENO, and GAP was 111 amino acids for an Mr of 13.35-kDa. The DNA encoding for the SOP with a His$_6$ tag at the carboxy terminus was cloned into a pET23b expression plasmid construct that was transformed into *E. coli* B121DE3. Recombinant *E. coli* (r*E. coli*) was stored as glycerol stocks at −70° C. until used, which were thawed and streaked onto Luria Broth (LB) agar plates containing 25 μg ampicillin (amp). Isolated colonies were inoculated into 200 ml fresh LB containing amp and incubated in a shaker incubator at 37° C. and 220 rpm. Following overnight growth, r*E. coli* were inoculated into fresh LB medium with amp and incubated for 3 hours at 37° C. at 220 rpm prior to addition of 1 mM IPTG and incubation an additional 3 hours. The r*E. coli* were centrifuged using a Sorvall SLA-1500 rotor at 8,000 rpm and 4° C. for 15 minutes. Supernatant was decanted, and the pellet was stored at −80° C. until used. At various time intervals, prior to and after IPTG addition, 1 ml of r*E. coli* were microfuged at 10,000 rpm for 15 minutes and pellets prepared for SDS-PAGE (34, 35) for analysis of recombinant SOP::His$_6$ fusion protein (12.2-kDa) expression after IPTG addition. Immunoblot analysis after SDS-PAGE, shown in FIG. 8, confirmed the synthesis of SOP::His$_6$ using as probe positive control sera of women and men that were seropositive to α-actinin as defined above.

ELISA was performed by immobilizing purified SOP protein onto 96-well, flat-bottom Nunc polysterene plates. Each well was coated with 100 μl containing 1 μg of SOP diluted in carbonate:bicarbonate buffer, pH 9.6, and the plates were incubated overnight at RT with gentle agitation. Each plate was then washed 3× with PBS-T. On the third wash the plates were incubated in PBS-T for 5 minutes at RT with gentle agitation prior to removing the PBS-T. The plates were then incubated upside down o/n at RT on paper towels before being covered with plastic wrap and stored at 4° C. until used. For testing, plates were washed twice with PBS-T. On the second wash the plates were incubated in PBS-T at RT for 5 minutes with gentle agitation and slap-dried. Each well was then blocked with 200 μl of eBSA-PBS for 2 hours at 37° C. Plates were then washed twice with PBS-T. On the second wash the plates were incubated in PBS-T at RT for 5 minutes with gentle agitation followed by removing the PBS-T. Next, 100 μl of a 1:25 dilution in eBSA-PBS of women and men sera was added to each well in duplicate and incubated at RT for 5 minutes with gentle agitation before incubation for 4 hours at 37° C. The plates were washed three times with PBS-T. On the third wash the plates were incubated in PBS-T for 5 minutes at RT with gentle agitation. After removal of the PBS-T, 100 μl of secondary horseradish peroxidase-conjugated goat-anti-human IgG (Fc-specific) diluted 1:1,500 in eBSA-PBS was added to each well and incubated at RT with gentle agitation for 5 minutes before incubation for 1 hour at 37° C. The plates were washed 3× with PBS-T, as above, prior to addition of 100 μl of color development solution, prepared according to the manufacturer's instructions well and incubated at RT with gentle agitation for 15 minutes. Absorbance values at 405-nm were obtained using Bio-Tek plate reader (Bio-Tek Instruments, Inc).

We performed assays to assess whether this novel recombinant protein is detectable with positive control sera of women and men, as above. FIG. 8A shows representative reactions by ELISA with SOP arrays immobilized onto individual wells of 96-well microtiter plates. Negative control sera of women and men had little to no reactivity as evidenced by low $A_{405\ nm}$ with the SOP in comparison to the strong signals (high $A_{405\ nm}$) obtained with positive sera of women and men. The SOP was undetectable when using an irrelevant MAb HA423 to α-actinin of $T.$ $vaginalis$ (XX) compared to the very strong reaction seen with a positive control MAb to hexa-histidine in the fusion recombinant protein.

Further, FIGS. 8B and 8C demonstrates that antibodies in positive sera of women and men react with the SOP array and are detected by dot-blots (FIG. 8B) and by immunoblot after SDS-PAGE and immunoblotting onto nitrocellulose (FIG. 8C). The Coomassie-brilliant blue stained gel is a duplicate from the SDS-PAGE used for immunoblotting of the SOP, and the Ponceau S-stained nitrocellulose is a duplicate included to show the transfer of the SOP protein onto nitrocellulose.

Example 9. Epitopes of Highly Immunogenic $T.$ $vaginalis$ α-Actinin Used as Serodiagnostic Targets for Both Women and Men Highly immunogenic α-actinin protein and protein fragments were characterized to further establish utility as a target for serodiagnosis of trichomonosis for both women and men. It is known that the sera of women with trichomonosis possess antibody reactive with numerous trichomonad proteins, including α-actinin (referred to as positive control women sera). Epitope mapping identified 13 peptide epitopes within α-actinin reactive to the positive control sera of women. Men sera highly-seropositive to the trichomonad parent α-actinin and the truncated version called ACT-P2 (positive control men sera) identified 5 epitopes that were a subset of those detected by positive control women sera. The amino acid sequences of the epitopes had little or no sequence identity to the human α-actinin homolog and to proteins of other microbial pathogens, including a related $Tritrichomonas$ $suis$ and yeasts $Candida$ $albicans$ and $Saccharomyces$ $cerevisiae$. Further, immobilized 15-mer peptides of representative epitopes are reactive to both positive control women and men sera.

A plasmid was constructed to encode an SOP array of all thirteen epitopes of α-actinin as shown in FIG. 9 (SEQ ID NO:146). This actinin SOP is expressed in $E.$ $coli$ as is the SOP presented above expressing epitopes of ALD, ENO, and GAP. In this case, the thirteen epitopes detected antibodies in the sera of women and men exposed to $T.$ $vaginalis$ are arranged sequentially within individual 15-mer peptides, which were separated from each other by a diglycine (-GG-). recombinant $E.$ $coli$ with the plasmid construct with the DNA sequence encoding this recombinant SOP of α-actinin is induced for expression of the protein. The α-actinin epitope protein is a fusion protein with a hexa-histidine sequence at the carboxy-terminus for purification as above by nickel-affinity chromatography. Purified α-actinin SOP can be immobilized for detection antibodies in the sera of women and men.

Materials and Methods

α-Actinin-P2 (ACT-P2) Expression and Purification.

The natural $T.$ $vaginalis$ α-actinin protein consists of 931-amino acids and is 106.2-kDa. This full-length highly immunogenic protein is used for examining the relation between seropositivity in men and prostate cancer. Subclones of the trichomonad α-actinin gene are made to determine the region of the protein most reactive with men sera. This subclone encoded a protein of 558-amino acid protein from the amino terminus, called ACT-P2. The coding region of ACT-P2 corresponding to amino acids 375 to 932 is PCR amplified and cloned in pET23b expression vector with the kanamycin resistance gene ($Kan^r$) for transformation of $E.$ $coli$ BL21DE3 cells. The resulting recombinant 558-amino acid sequence further comprises a C-terminal $His_6$ tag fusion protein of 63.5-kDa. Bacteria are grown on Luria Broth (LB) agar plates containing 25 μg/ml Kan, and r$E.$ $coli$ is incubated for 3 hours at 37° C. at 220 rpm prior to addition of 1 mM isopropylthiogalactoside and incubated for an additional 3 hours. The r$E.$ $coli$ are centrifuged using a Sorvall SLA-1500 rotor at 8,000 rpm and 4° C. for 15 minutes. and pellets stored at −80° C. until used. Synthesis of ACT-P2 is confirmed using as probe the murine monoclonal antibody (MAb) HA423 (27-29) to trichomonad α-actinin or MAb to $His_6$ (Advanced Targeting Systems, San Diego, Calif., USA).

For purification of ACT-P2, pellets of r$E.$ $coli$ are thawed for 15 min on ice and suspended in 10-ml lysis buffer (50 mM Tris, pH 8.0, 300 mM NaCl, 10 mM β-mercaptoethanol (β-ME), and 0.1% Triton-X100), and lysates are sonicated 10 times each at room temperature (RT) for 30 seconds (sec). Sonicates are centrifuged using a Sorvall SS-34 rotor at 8,000 rpm and 4° C. for 20 minutes (min), and supernatant is applied to a $Ni^{2+}$-NTA superflow affinity column according to the manufacturer's instructions (Qiagen Inc., Valencia, Calif., USA). Purified ACT-P2 protein is confirmed by SDS-PAGE and immunoblot using as probe MAb HA423, as above.

The Human ACTN1 Homolog.

The purified full-length human ACTN1 α-actinin homolog used in this study is the isoform B protein of 892 amino acids (~103-kDa) (Novus Biologicals, Littleton, Colo., USA). The soluble protein is in 74 mM Tris-HCl, pH 8.0, containing 10 mM reduced glutathione. For ELISA and immunoblot assays 1 μg of ACT-P2 and ACTN1 is used. ELISA is performed using wells of microtiter plates coated with ACT-P2 or ACTN1 as detailed below. SDS-PAGE for immunoblotting onto nitrocellulose for both ACT-P2 and ACTN1 is carried out using 7.5% acrylamide gels, as before (36, 37).

Positive Control Sera of Women and Men and Detection of Antibody to ACT-P2.

During the course of our research on *T. vaginalis* we have examined ~1,000 sera of women patients with trichomonosis and, more recently, up to 20,000 sera of men for seropositivity to trichomonad proteins and particularly α-actinin. We, therefore, were able to determine the extent of serum antibody to total *T. vaginalis* proteins, α-actinin, and ACT-P2 by ELISA (27-29). Individual, α-actinin-seropositive sera of women and men had identical or very similar reactivities to trichomonad proteins and α-actinin. This permitted us to pool the sera to have sufficient amounts for conducting epitope mapping experiments, as outlined below, and was considered positive control sera. Likewise, pooled seronegative sera of both women and men were considered negative control sera for parallel experiments conducted throughout.

Trichomonad Natural α-Actinin SPOTs Membrane Synthesis for Epitope Mapping.

Oligopeptides derived from the sequences of *T. vaginalis* α-actinin (GenBank accession number AAC72899) were synthesized on activated membranes using the SPOTs system (Sigma-Genosys, The Woodlands, Tex., USA). Five to 10 nmol of each peptide was covalently bound to a Whatman 50 cellulose support (Whatman, Maidstone, England) by the C-terminus using Fmoc-L amino acid chemistry and had an acetylated N-terminus. The oligopeptides were 11-mer amino acids in length and had a sequential overlap of eight amino acids. The SPOTs spanned the entire sequence of the protein.

Probing the α-Actinin SPOTs Membrane with Positive and Negative Control Sera and MAb HA423.

The membrane was initially washed with a small volume of 100% MeOH for 5 minutes to avoid precipitation of hydrophobic peptides during the following procedure. After washing 3× each for 10 minutes in 25 ml of TBS buffer (50 mM Tris-HCl, pH 8.0, 137 mM NaCl, and 2.7 mM KCl), the SPOTs membrane was incubated in Blocking Buffer (TBS containing 5% BSA) at RT for 2 hours. The membrane was incubated with a 1:10 dilution of negative or positive control sera of women and men, respectively, and incubated overnight at 4° C. The membrane was also probed with the MAb HA423 that detects α-actinin. After washing 3× each for 5 minutes each in TBS, the membrane was incubated with a 1:1,500 dilution of secondary anti-human antibody as above or anti-mouse IgG Fab (IgG fraction) prepared in Blocking Buffer. After washing 3× each in TBS at RT for 5 minutes each, bound antibodies were detected using color development reagent.

Immediately following color development and SPOT analysis, the membrane was regenerated by washing 3× with water with each wash for 10 minutes at RT with agitation. Bound antibody was stripped from the membrane by washing at least 4 times with each wash for 30 minutes with Regeneration Buffer I (62.5 mM Tris-HCl, pH 6.7, 2% SDS, and 100 mM ME) at 50° C. with agitation. The membrane was washed three times each for 20 minutes with 10×PBS at RT with agitation, after which the membrane was washed 3× each for 20 minutes with T-TBS buffer (TBS, pH 8.0, containing 0.05% Tween 20) at RT with agitation. This was followed by washing 3× each for 10 minutes with TBS at RT with agitation. The presence of any visible spots resulted in repeating the regeneration steps. As a control to show that the primary antibody was completely removed, the membrane was re-incubated with the appropriate secondary antibody and substrate solution and developed. Regeneration was continued until no reactivity was seen with secondary antibody.

The epitope amino acid sequences were determined based on reactivities of overlapping peptides, as shown above in Table 11. Epitope sequences were compared with other proteins by using the protein-protein basic local alignment search tool found on a page of the NCBI website. Amino acid sequence alignments of the proteins were performed with CLC Protein Workbench (Muehltal, Germany). Hydrophobicity plots and antigenicity plots were constructed using Lasergene MegAlign (DNASTAR, Madison, Wis.).

Synthesis and Reactivity of Individual α-Actinin Epitopes.

Three 15-mer peptide epitopes identified from SPOT membrane epitope mapping with low percent identity to other human pathogens as well as the α-actinin human homolog were synthesized in PEPscreen format (Sigma-Genosys). The reactivity of each peptide was tested with representative negative and positive control sera either individually or in combination. Approximately 10 µg of peptide was blotted onto nitrocellulose membranes and air dried overnight at RT. The epitope blots were then blocked with 2% e-BSA in PBS at 37 C for 2 hours followed by incubation with 1:25 dilution in PBS of negative or positive control women and men sera for ACT-P2 and incubated overnight at RT. This was followed by secondary antibody and color development, as above. All assays were performed in duplicate and repeated at least three times.

Results

Positive Control Sera of Women and Men does not Detect the Human α-Actinin Homolog Protein.

Figure 10:
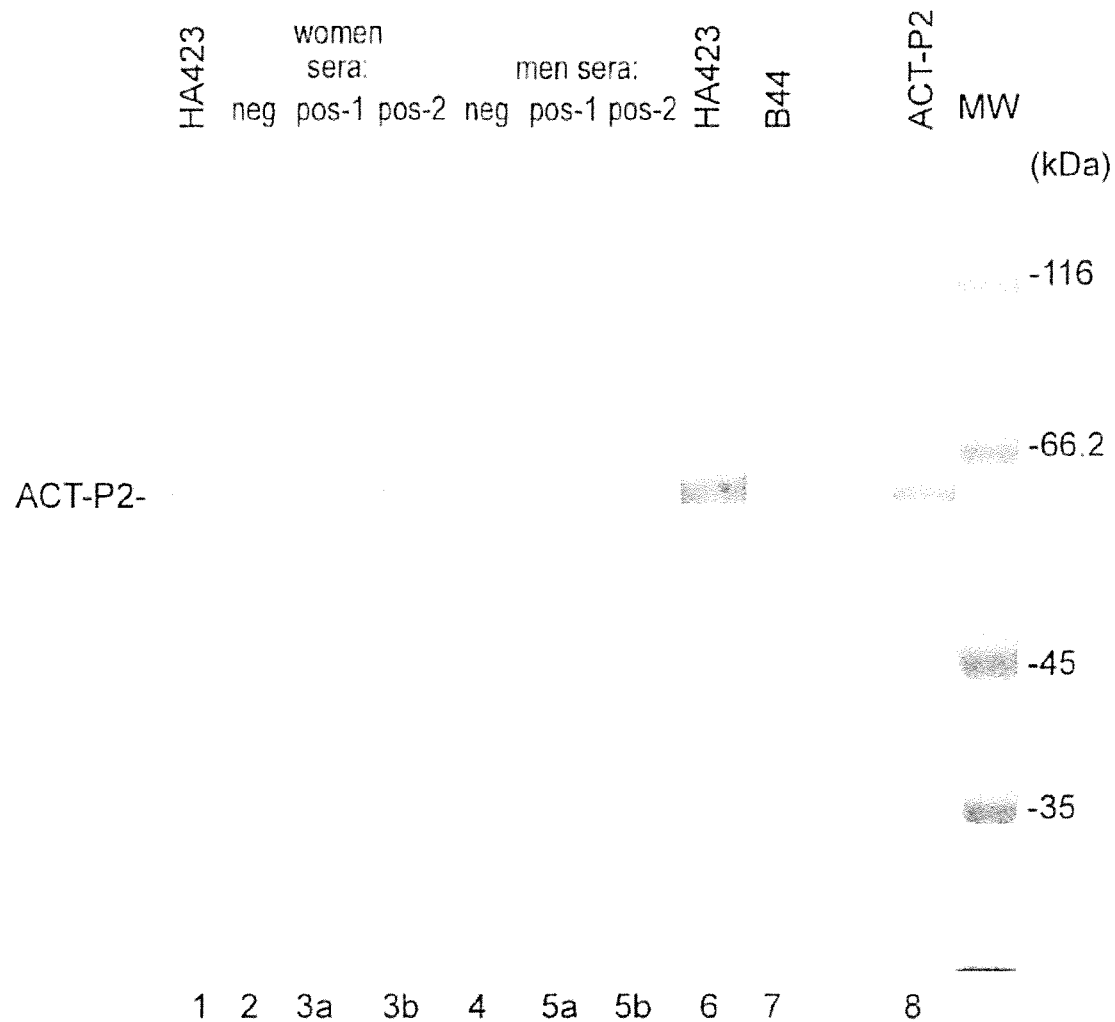
FIG. 10 shows immunoblot detection of ACT-P2 using IgG1 MAb HA423 and positive control sera from women and men.

Negative and positive control sera of women and men were used to probe immunoblots of ACT-P2. As can be seen in FIG. 10 positive (pos) control sera of women (lanes 3a and 3b) and of men (lanes 5a, and 5b) detected ACT-P2 in two separate experiments done at different times under identical experimental conditions. Negative (neg) control sera of women and of men gave no detectable bands (lanes 2 and 4, respectively). The IgG$_1$ MAb HA423 to the trichomonad α-actinin used as probe gave strong reactivity in separate experiments (lanes 1 and 6), and, not unexpectedly, an irrelevant IgG$_1$ MAb B44 reactive with trichomonad α-enolase as a negative control detected no protein band.

Figure 11A:
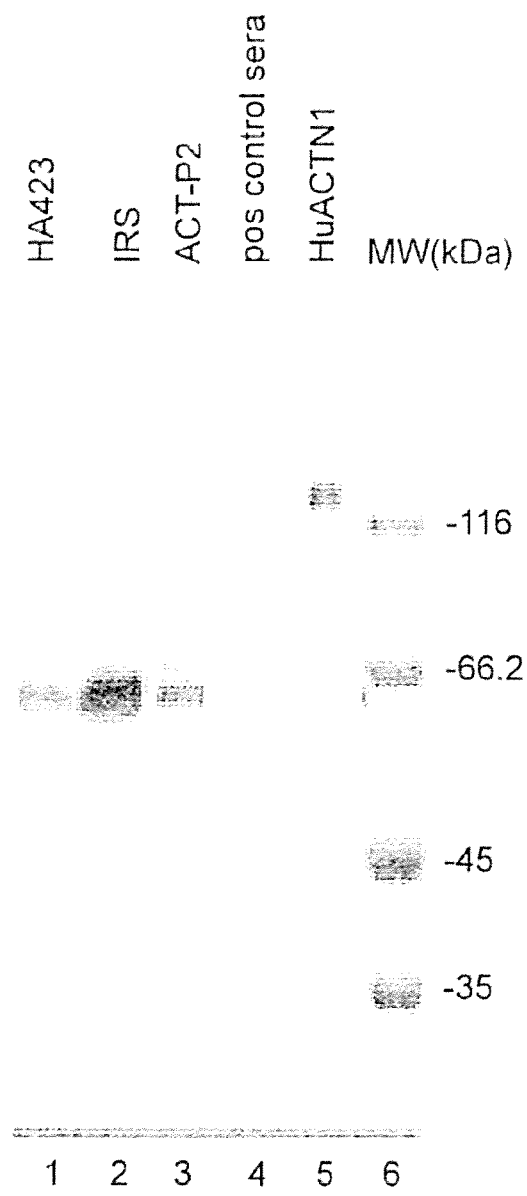
FIGS. 11A and 11B are gels showing that pooled positive control sera from both women and men are unreactive with HuACTNa and have antibodies to numerous trichomonad proteins.
Figure 11B:
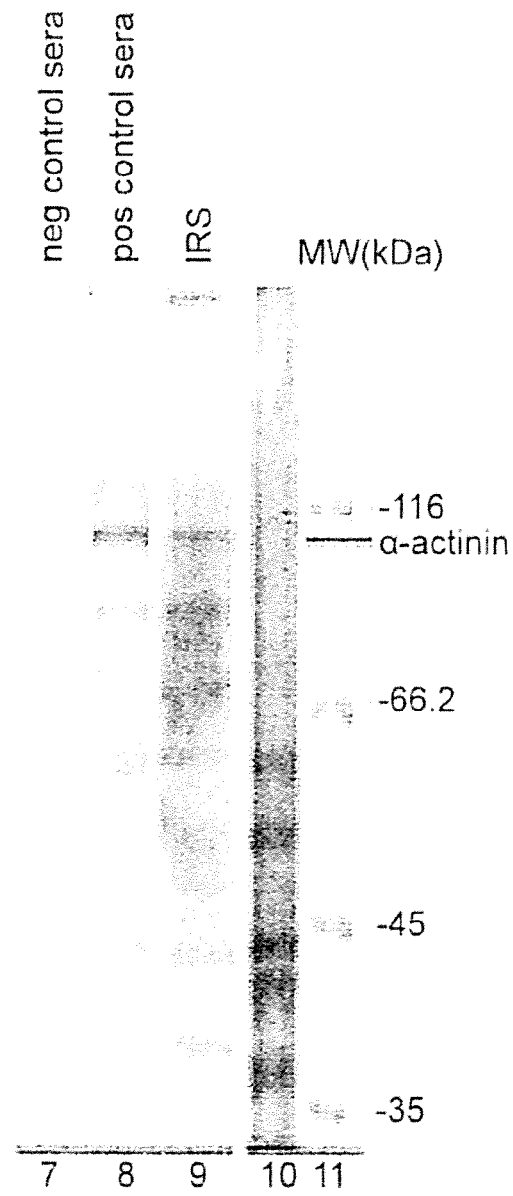

We next tested for immuno-crossreactivity purified, commercially-available human α-actinin (HuACTN1) with pooled positive control sera of women and men used in FIG. 10. FIG. 11A (lane 5) shows the intense stained band of 1 µg HuACTN1. Gels with the same amount of HuACTN1 were transferred onto nitrocellulose for immunoblotting. A duplicate blot with HuACTN1 was stained to insure transfer of the protein (not shown). The HuACTN1 was neither detected by the positive control sera (lane 4) nor HA423 (not shown). As above, 1 µg of ACT-P2 (lane 3) was readily detected by MAb HA423 (lane 1) and rabbit antiserum to total *T. vaginalis* proteins (IRS, lane2). We then tested by immunoblot using total proteins of *T. vaginalis* (lane 10), as before, whether the pooled positive control sera of both women and men detected numerous other trichomonad proteins. FIG. 11B shows that pooled negative control sera did not detect any trichomonad proteins by immunoblot (lane 7) whereas pooled positive control sera recognized numerous proteins (lane 8). As a control and not surprisingly, many trichomonad proteins in the total protein preparation were evident when blots were probed with IRS (lane 9). As with negative control sera of women and men (lane 7), no proteins were detected by control, prebleed normal rabbit serum. Finally, we tested for detection of non-denatured HuACTN1 coated onto wells of microtiter plates. Again, neither positive control sera of women and men nor MAb HA423 reacted to the HuACTN1-coated wells (not shown).

α-Actinin Epitopes React with Positive Control Sera of Women and Men and MAb HA423.

We next tested the positive control sera of women and men strongly reactive with ACT-P2 for IgG antibody to overlapping 11-mer peptides on a Custom SPOTs membrane (Materials and Methods). Table 5A of Example 7 lists the 13 epitopes and corresponding amino acid sequences labeled W1 through W13 recognized by women sera. M1 through M5 represent the subset of epitopes detected by men sera. The IgG$_1$ MAb HA423 detected the same epitope as W12/M4. Negative control sera of women and men and the MAbs B43 and B44 to trichomonad GAPDH and α-enolase, respectively, which were the same isotype as HA423, were unreactive with the SPOTs membrane.

FIG. 12A shows a representative reaction for epitope detection of 11-mer overlapping peptides (SEQ ID NO:162-165) for spots numbered 214 through 217. The highly reactive SPOTs 214 through 217 for positive control sera of women indicates the epitope sequence of 643-VEFKLNYK-VTY-653 (SEQ ID NO:163). (FIG. 12B). Likewise, the 216 and 217 peptides reactive with positive control sera of men suggest the sequence 649-YKVTYS-653 as the epitope. No reactivity was seen with negative control sera of either women or men. The MAb HA423 epitope is 643-VEFKL-NYKVTY-653 (SEQ ID NO:163). FIG. 12C shows the strong dot-blot reaction by positive control sera of women and men to ACT-P2 immobilized on nitrocellulose. We then synthesized 15-mer peptides overlapping W10/M2 (AQPLY DEAIAFKEEV) (SEQ ID NO:101) and W13/M5 (FKDTF KYFDKDKSNS) (SEQ ID NO:102), epitopes from Table 11 (epitopes underlined), and immobilized 1 µg of each peptide together and probed with positive control sera. The sera of both women and men reacted with the combined 15-mer peptide epitopes (FIG. 12D). FIG. 12E presents densitometric scans of the reactive spots and shows the elevated level of detection by men sera compared to women sera. Finally, FIG. 12F shows the reactivity of individual 15-mer peptides containing the epitopes of W9/M1

(SEQ ID NO: 100)
(SVNRHHSQLITYIKH),

W10/M2, and W13/M5 with positive control sera. FIG. 12G illustrates the densitometric scans that show men sera giving elevated intensities to W9/M1 and W10/M2 compared to women sera. The extent of detection was identical for both sera of women and men to the epitope W13/M5. Negative control sera of both women and men showed no reactions in these dot-blots of epitopes.

Hydrophobicity and Antigenicity Profiles of the Natural α-Actinin Sequence.

Figure 13:
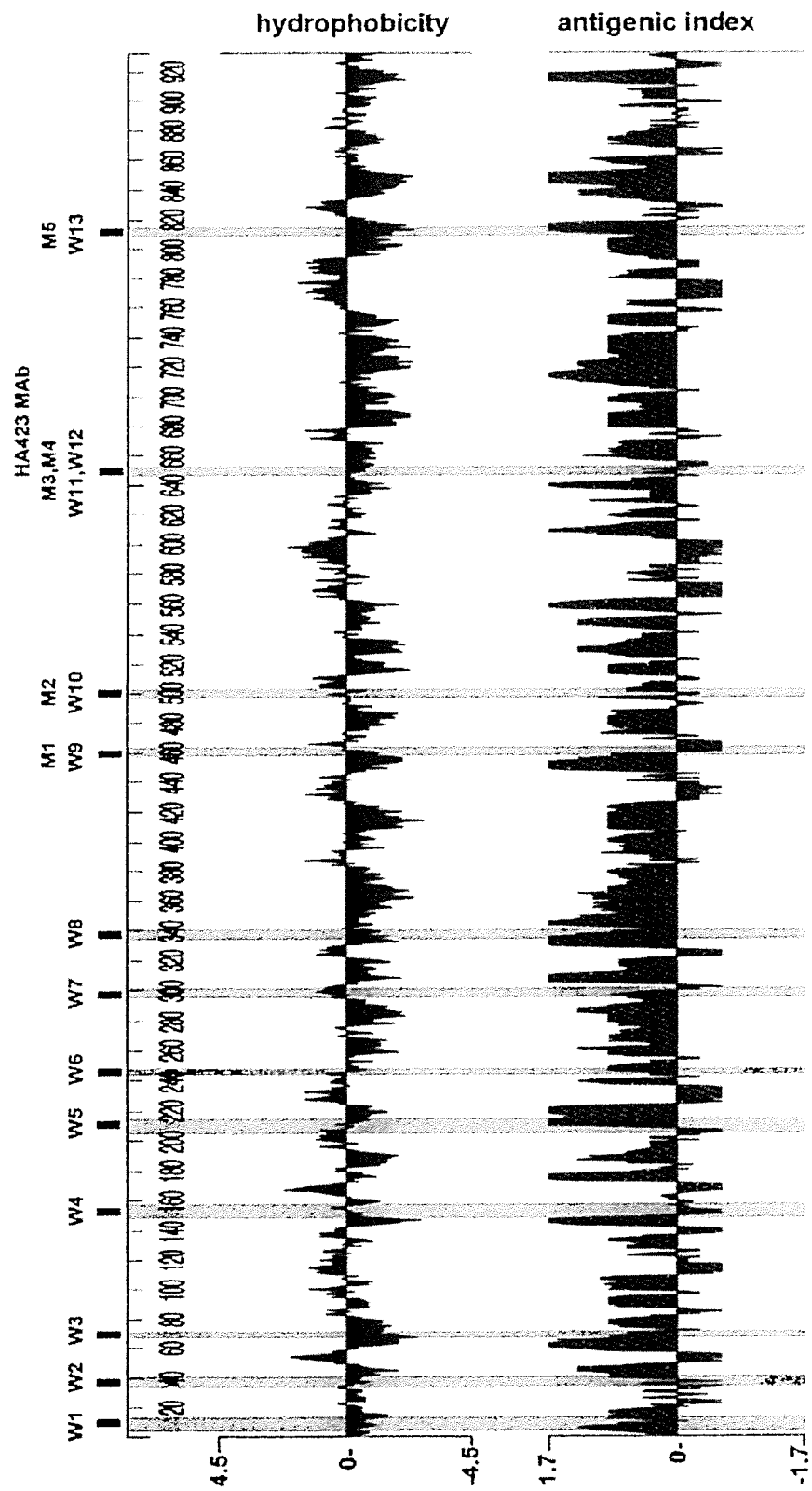
FIG. 13 shows a hydrophobicity plot and antigenicity profile for *T. vaginalis* α-actinin.

We then analyzed the immunoreactive epitopes of Table 11 for hydrophobicity and antigenicity. FIG. 13 demonstrates the mapping of the epitopes with the respective profiles and shows that most epitopes were hydrophilic and corresponded with predicted antigenicity. As representative examples, epitopes W3, W4, W8, HA423/M4/W12, and M5/W13 each gave prominent hydrophilic and antigenic characteristics that were not inconsistent with serum antibody detection.

Sequence Alignment of the T. vaginalis α-Actinin with Proteins of Other Representative Organisms and of the HuACTN1.

BLAST of T. vaginalis α-actinin amino acid sequence (SEQ ID NO:157) is presented in FIGS. 14A, 14B, 14C, and 14D and shows little amino acid percent identity with α-actinin-like proteins of different species. The low percent identity of amino acids is particularly noteworthy for the boxed epitope sequences indicated above the T. vaginalis amino acid sequence detected by both positive control sera of women and men. Table 12 summarizes the percent amino acid sequence identity comparisons for the individual epitopes compared with sequences for T. suis, a related trichomonad, and the yeasts C. albicans, and S. cerevisiae.

The organisms shown in FIGS. 14A, 14B, 14C, and 14D and Table 12 were chosen because of their relation to STIs and/or eukaryotic pathogens. The range of amino acid percent identity was from 0% to 25%. The percent amino acid identity for α-actinin of T. vaginalis compared with the HuACTN1 was 0% to 50%. Not unexpectedly, the seemingly high percent sequence identity of any epitope with the corresponding region of HuACTN1 decreased when neighboring amino acids were analyzed. Specific synthesized peptide epitopes of α-actinin with low to no amino acid sequence identity with other proteins were reactive with positive control sera of both women and men, as shown for representative epitopes in FIG. 12.

Discussion

Research in our laboratory led to the development of the lateral flow, immunochromatographic diagnostic for detection of trichomonad protein in female patients, and this diagnostic was commercialized and is currently in use in the United States and other countries (OSOM® Trichomonas Rapid Test, Sekisui Diagnostics, San Diego, Calif.). This diagnostic, developed in our laboratory, works on neither urine nor secretions obtained from male patients nor on urine spiked with lysates of total T. vaginalis proteins based on our analysis in the laboratory. Reports suggesting a relation between seropositivity to the ACT-P2 of T. vaginalis and prostate cancer reveal the need for a serum-based point-of-care diagnostic that utilizes a highly specific target. Our data show that the 558-amino acid ACT-P2 is a good target for detection of antibody in both women and men seropositive to T. vaginalis. This region of ACT-P2 was found to possess less homology with other α-actinin-related proteins, further reinforcing its diagnostic value. The fact that the epitopes detected by the positive control sera of men are located toward the C-terminus revealed why ACT-P2 was a good target for our earlier screening for serum antibody. It is noteworthy that there is absent or little identity between the peptide-epitope sequences with other proteins in databanks and among proteins for T. suis, C. albicans, and S. cerevisiae and the HuACTN1 of humans (Table 12 and FIGS. 14A, 14B, 14C, and 14D). This suggests strongly that high seropositivity is the result of exposure to T. vaginalis. Furthermore, of particular interest is that 15-mer synthetic peptide-epitopes found within ACT-P2 immobilized onto nitrocellulose were detected by sera of both positive control sera women and men reactive to α-actinin (FIG. 12). Perhaps not surprisingly, most of the peptide epitope amino acid sequences represented portions of the protein that were hydrophilic and antigenic (FIG. 4). The representative 15-mer synthetic peptides corresponding to W10/M2 and W13/M5 that were readily detected on immobilized surfaces were in fact highly hydrophilic (FIG. 12). This further suggests that the reactive 15-mer epitopes represent linear, readily detectable epitopes. A cocktail of or a recombinant protein encoding for a series of highly-reactive epitopes, such as a rSOE or SOP, represents diagnostic targets.

It is not surprising that α-actinin represents a target for serodiagnostic. This is one of the most immunogenic proteins of *T. vaginalis*. Its function is to associate with actin, which is important because of the dramatic and rapid morphologic transformation that this organism undergoes immediately following contact with vaginal epithelial cells, prostate epithelial cells (unpublished data), and extracellular matrix proteins, such as laminin and fibronectin. Indeed, recent transcriptomic and proteomic analyses has revealed the dramatic increased expression levels of α-actinin required for cytoskeletal rearrangements for morphological changes upon adherence to vaginal epithelial cells and binding to fibronectin. Further, equally elevated amounts of mRNA encoding for trichomonad GAPDH and α-enolase were found, and both of these proteins are surface ligands for binding fibronectin. There are four α-actinin human homologs, none of which are crossreactive with the MAb HA423 to the trichomonad α-actinin (FIG. 9 and Table 15) and with positive control sera of women and men. These human α-actinin proteins are known to have a less conserved central region, as is the case for all actin-binding proteins of the spectrin family.

Equally noteworthy is that the epitopes detected by MAb HA423 and positive control sera of women and men are invariant. Laboratory-adapted *T. vaginalis* isolates grown in batch culture for >20 years possess the MAb 423-immunoreactive α-actinin with the same $M_r$. Further, more than fifty fresh clinical isolates, one-half of which are the Type II P270 phenotypically-varying isolates with the dsRNA virus, all possess α-actinin detected by MAb and positive control sera of women and men. We have seen no relation between *T. vaginalis* with or without *Mycoplasma* and changes with α-actinin. Thus, this invariant and stable immunogenic protein appears suitable for a rapid serodiagnostic test for trichomonosis.

Of interest is the number of epitopes detected by the positive control sera of women patients compared to sera of men. This may be the result of different presentation of the protein(s) during immune surveillance that results from the unique urogenital regions of women in contrast to men. It is known to those of ordinary skill in the art that women patients with trichomonosis possess IgG antibody in the serum and vagina to numerous trichomonad proteins, perhaps indicating a more vigorous antibody response during infection compared to men. Studies by others demonstrated the highly immunogenic nature of and serum antibody response by women to α-actinin. Nonetheless, these data show that men respond to exposure to *T. vaginalis* by producing serum IgG antibody, especially to the epitopes located toward the carboxy-terminal region with the least identity to other known proteins. Importantly, what remains unknown is the temporal relationship between seropositivity with initial exposure to this STI, and this critical absence of clinical information perhaps may be corrected through future availability of a serodiagnostic for women and men. What is known, however, albeit in only a small sample size is that one week after treatment of women with trichomonosis the vaginal antibody to proteinases was not detected.

The literature is replete with examples of peptide epitopes utilized for diagnostics of infectious diseases. For example, rapid diagnostics for *Plasmodium falciparum* employ epitopes of histidine-rich proteins. Diagnosis of visceral leishmaniasis is performed with rapid antigen-based tests, and specific epitopes of the proteins p120 and p140 are used for detection of *Ehrlichia chaffeensis* and *E. canis*, respectively. This shows the value of characterization of immunogenic epitopes for developing specific targets for serodiagnosis.

In summary, our results present evidence for the validity of α-actinin and the truncated ACT-P2 as a target for serodiagnosis in both women and men exposed to *T. vaginalis*. This is important not only for screening men possibly exposed to this STI in relation to the possibility of prostate cancer development but for a more rapid, non-invasive test for women as well. This approach highlights the methods by which peptide epitopes of immunogens may be identified as targets for antibody detection for determining exposure to and infection by this significant STD pathogen.

Example 10. α-Actinin String-of-Pearls (KK-ACT-SOP) Epitopes, and SOE Sequences

Sequences are shown in Table 15, comprising 229 amino acids; pI=9.93; MW=27,207 Da.

TABLE 15

T. vaginalis α-Actinin epitopes, and SOE sequences

| | EPITOPE # | EPITOPE NAME | AA SEQUENCE |
|---|---|---|---|
| SEQ ID NO: 107 | 1 | W1 | SVRREGLLDDAWEKT |
| SEQ ID NO: 108 | 7 | W2 | LARQIQFETIETDFE |
| SEQ ID NO: 109 | 3 | W3 | PSKWHKQPKMMVQKR |
| SEQ ID NO: 110 | 4 | W4 | QGYEHVAVNNFTTSW |
| SEQ ID NO: 111 | 5 | W5 | GIYVYLDPEDVIDTT |
| SEQ ID NO: 112 | 6 | W6 | KIAAMADKIKRTVAI |
| SEQ ID NO: 113 | 7 | W7 | IPGIRGKLASVISYN |
| SEQ ID NO: 114 | 8 | W8 | CKSGNRPIPEIPQGL |
| SEQ ID NO: 100 | 9 | W9/M1 | SVNRHHSQLITYIKH |
| SEQ ID NO: 101 | 10 | W10/M2 | AQPLYDEAIAFKEEV |

TABLE 15-continued

T. vaginalis α-Actinin epitopes, and SOE sequences

| | EPITOPE # | EPITOPE NAME | AA SEQUENCE |
|---|---|---|---|
| SEQ ID NO: 117 | 11 | W11/M3 | ELVEFKLNYKVTYTY |
| SEQ ID NO: 118 | 17 | W12/M4/HA423 | EFKLNYKVTYTYSDA |
| SEQ ID NO: 102 | 13 | W13/M5 | FKDTFKYFDKDKSNS |
| SEQ ID NO: 120 | | | KK-SVRREGLLDDAWEKT-KK-LARQIQFETIETDFE-KK-PSKWHKQPKMMVQKR-KK-QGYEHVAVNNFTTSW-KK-GIYVYLDPEDVIDTT-KK-KIAAMADKIKRTVAI-KK-IPGIRGKLASVISYN-KK-CKSGNRPIPEIPQGL-KK-SVNRHHSQLITYIKH-KK-AQPLYDEAIAFKEEV-KK-ELVEFKLNYKVTYTY-KK-EFKLNYKVTYTYSDA-KK-FKDTFKYFDKDKSNS-KK-HHHHHH |
| SEQ ID NO: 120 | | | KKSVRREGLLDDAWEKTKKLARQIQFETIETDFEKKPSKWHKQPKMMVQKRKKQGYEHVAVNNFTTSWKKGIYVYLDPEDVIDTTKKKIAAMADKIKRTVAIKKIPGIRGKLASVISYNKKCKSGNRPIPEIPQGLKKSVNRHHSQLITYIKHKKAQPLYDEAIAFKEEVKKELVEFKLNYKVTYTYKKEFKLNYKVTYTYSDAKKEKDTFKYFDKDKSNSKKHHHHHH |
| SEQ ID NO: 12 | | | KKSVRREGLLDDAWEKTKKLARQIQFETIETDFEKKPSKWHKQPKMMVQKRKKQGYEHVAVNNFTTSWKKGIYVYLDPEDVIDTTKKKIAAMADKIKRTVAIKKIPGIRGKLASVISYNKKCKSGNRPIPEIPQGLKKSVNRHHSQLITYIKHKKAQPLYDEAIAFKEEVKKELVEFKLNYKVTYTYKKEFKLNYKVTYTYSDAKKFKDTFKYFDKDKSNSKKHHHHHH |

Example 11. Examples of *T. pallidum* Highly Immunogenic Peptides, 15-Mer Epitopes, and SOE as Targets for Serodetection, Shown in Table 16

Epitope sequences identified as SEQ ID NO: 121-126 are highly immunogenic (see Brinkman, Antoni, and Liu cited below). Additional immunogenic protein sequences for *T. pallidum* are provided in SEQ ID NO: 161-164. Based on this information, and using the methods of the disclosure, the SOE of SEQ ID NO: 127 was designed and synthesized. Experimental evidence shows that it is able to detect *T. pallidum* in a biological sample, and to elicit an immune response when injected into a subject. The $H_6$ (also referred to as hexa-His) at the amino terminal end of the SOE polypeptide is for purification of the SOE using Ni-NTA (n

TABLE 17

N. gonorrhoeae highly immunogenic peptides encoded in 15-mer epitopes, and SOE.

| | AA SEQUENCE |
|---|---|
| SEQ ID NO: 128 | FGSKIGFKGQEDLGN |
| SEQ ID NO: 129 | GFSGSVQYAPKDNSG |
| SEQ ID NO: 130 | GFFAQYAGLFQRYGE |
| SEQ ID NO: 131 | VEKLQVHRLVGGYDN |
| SEQ ID NO: 132 | NSHNSQTEVAATAAY |
| SEQ ID NO: 133 | NTYDQVVVGAEYDFS |
| SEQ ID NO: 134 | KK-FGSKIGFKGQEDLGN-<br>KK-GFSGSVQYAPKDNSG-<br>KK-GFFAQYAGLFQRYGE-<br>KK-VEKLQVHRLVGGYDN-<br>KK-NSHNSQTEVAATAAY-<br>KK-NTYDQVVVGAEYDFS-<br>KK-HHHHHH |

Example 13. Production of a SOE Chimeric Construct Using Epitopes of T. vaginalis Fructose-1,6-Biphosphate Aldolase, α-Enolase, and GAPDH without Sequence Identity to Bacterial, Fungal, Parasite, and Human Proteins

TABLE 18

List of synthetic peptides of representative T. vaginalis epitopes of ENO, GAP, and ALD Mabs for reactivity with immunoreactive women and men sera. ALD13 and ALD32 refer to MAbs. Immunogenic residues detected by women and men sera are underlined.

| | women/men epitope designation | amino acid sequence |
|---|---|---|
| SEQ ID NO: 166 | E-ALD13 | AEHDAIVKECIAEAA |
| SEQ ID NO: 167 | E-W3, E-M3 | TDGTVLKKNIGGNAS |

TABLE 18-continued

List of synthetic peptides of representative T. vaginalis epitopes of ENO, GAP, and ALD Mabs for reactivity with immunoreactive women and men sera. ALD13 and ALD32 refer to MAbs. Immunogenic residues detected by women and men sera are underlined.

| | women/men epitope designation | amino acid sequence |
|---|---|---|
| SEQ ID NO: 168 | E-M7 | ILVKKYGLSAKNLDEF |
| SEQ ID NO: 169 | E-M8 | ASSEFYDEEKKLYEV |
| SEQ ID NO: 170 | E-M9 | DYENWTKLNARLGQRV |
| SEQ ID NO: 171 | G-M1 | RASRKLYPKDIQVVA |
| SEQ ID NO: 172 | G-W1, G-ALD32 | NVYLLKYDTAHRAFP |
| SEQ ID NO: 173 | G-W3 | VVLESTGIFRTKAEK |
| SEQ ID NO: 174 | G-W6 | TLNNAFGIRNGFMTTV |

Figure 16:
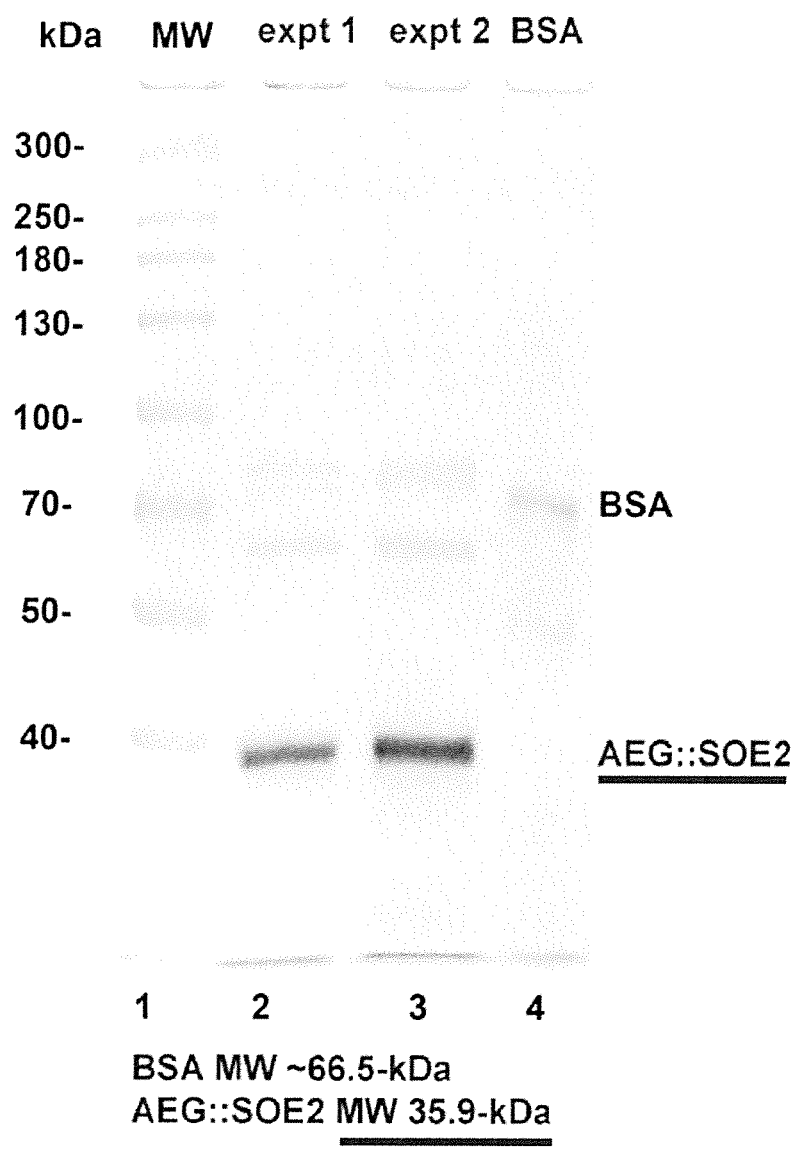
FIG. 16 shows a coomassie stained gel after SDS-PAGE of Ni-NTA-purified AEG:SOE2.
Figure 17:
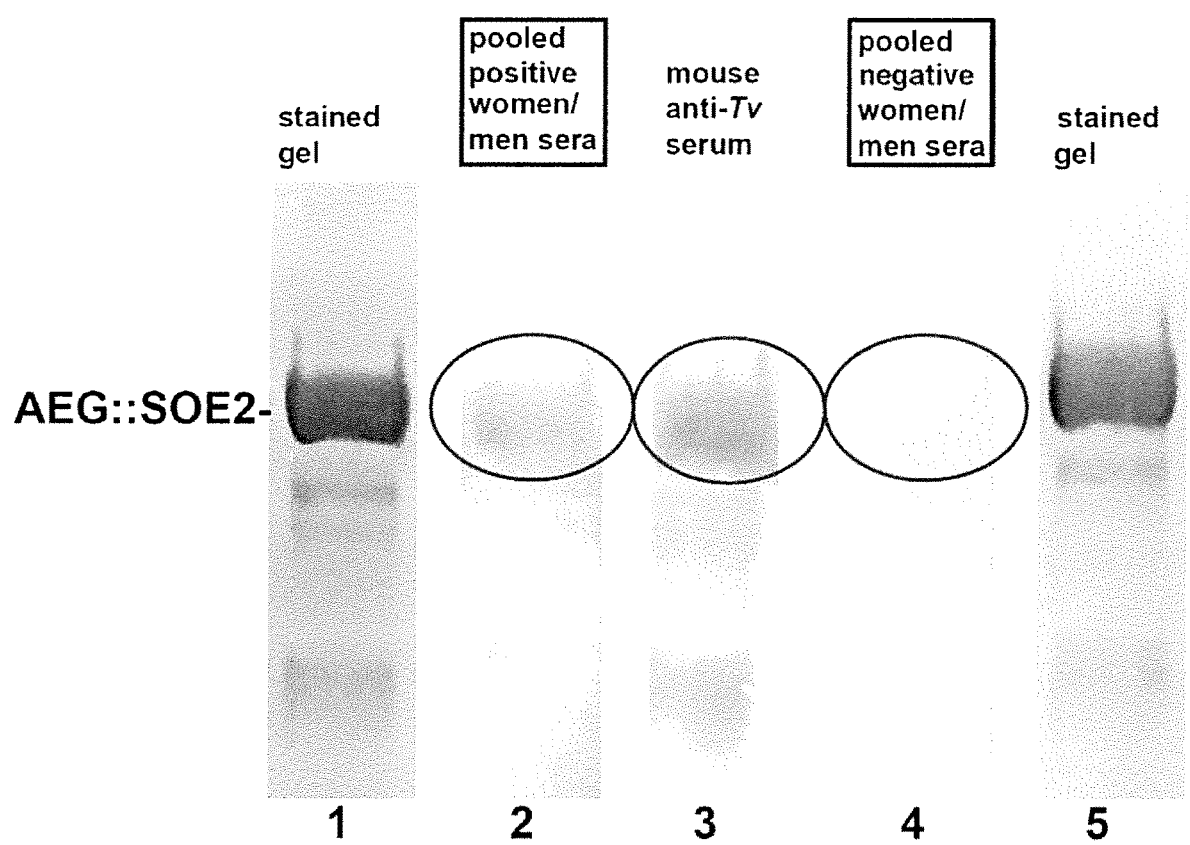
FIG. 17 shows an immunoblot of purified AEG:SOE2 on nitrocellulose probed with women/men sera and mouse anti-Tv serum.

The epitopes in Table 18 were combined with 9 additional epitopes as described herein to produce a SOE ("AEG: SOE2") having 18 epitopes linked with glutamic acid repeats (FIG. 15; SEQ ID NO: 175). The SOE has an isoelectric point of about 5.05 and a molecular weight of about 35.9 kDa (FIGS. 15-16). The SOE is reactive with pooled positive women/men sera and mouse anti-Tv serum but not with the pooled negative control women/men sera (FIG. 17).

The activity of the SOE was then compared to T. vaginalis α-actinin, an immunogenic trichomonad protein not found among other microorganisms (FIG. 19).

When compared to α-actinin, the SOE had a very high sensitivity, specificity, and predictive value when used as a serum diagnostic of T. vaginalis (FIG. 18).

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

The invention claimed is:

1. A method for detecting the presence of one or more *Trichomonas vaginalis* microorganisms in a biological sample of a subject, comprising the steps of:
    combining said biological sample with a polypeptide including a series of epitopes (SOE) which includes at least a plurality of epitopes selected from the group consisting of SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, and SEQ ID NO: 174, said epitopes being arranged as a linear array with each of said epitopes being connected by an amino acid linker, wherein said combining is performed under conditions whereby antigen-antibody complexes are permitted to form; and
    detecting formation of at least one antigen-antibody complex as an indication of a presence of at least one microorganism of said one or more *Trichomonas vaginalis* microorganisms in said biological sample.

2. The method of claim 1, wherein the SOE includes at least six epitopes.

3. The method of claim 1, wherein said *Trichomonas vaginalis* microorganisms are selected from the group consisting of *T. vaginalis* isolates T016, T068-II, UT40, and VB102.

4. The method of claim 1, wherein said detecting step is performed using an immunoassay.

5. The method of claim 4, wherein said immunoassay is an enzyme-linked immunosorbent assay (ELISA).

6. The method of claim 1, wherein said biological sample is selected from the group consisting of serum, plasma, blood, saliva, semen, cerebrospinal fluid, semen, prostatic fluid, urine, sputum, joint fluid, body cavity fluid, whole cells, cell extracts, tissue, biopsy material, aspirates, exudates, vaginal washings, pap smear samples, pap smear preparations, slide preparations, fixed cells, and tissue sections.

7. The method of claim 1, wherein said subject is selected from the group consisting of human, non-human primate, dog, cat, cattle, sheep, swine, horse, bird, mouse, and rat.

8. The method of claim 1, wherein the SOE has the sequence of SEQ ID NO: 175.

9. The method of claim 1, wherein the isoelectric point of the SOE is in a range from 4.90 to 5.10.

\* \* \* \* \*

SEQUENCE LISTING

<160> NUMBER OF SEQ ID NOS: 179

<210> SEQ ID NO 1
<211> LENGTH: 8
<212> TYPE: PRT
<213> ORGANISM: Trichomonas vaginalis

<400> SEQUENCE: 1

Arg Pro Asp Tyr Val Thr Val Glu
1               5

<210> SEQ ID NO 2
<211> LENGTH: 8
<212> TYPE: PRT
<213> ORGANISM: Trichomonas vaginalis

<400> SEQUENCE: 2

Lys His Thr Tyr Thr Arg Pro Glu

```
1               5

<210> SEQ ID NO 3
<211> LENGTH: 8
<212> TYPE: PRT
<213> ORGANISM: Trichomonas vaginalis

<400> SEQUENCE: 3

Glu Arg Ile Gln Lys Tyr Thr Arg
1               5

<210> SEQ ID NO 4
<211> LENGTH: 8
<212> TYPE: PRT
<213> ORGANISM: Trichomonas vaginalis

<400> SEQUENCE: 4

Asp Asp Leu Tyr Thr Thr Asn Pro
1               5

<210> SEQ ID NO 5
<211> LENGTH: 8
<212> TYPE: PRT
<213> ORGANISM: Trichomonas vaginalis

<400> SEQUENCE: 5

Ala Ile Val Lys Glu Cys Ile Ala
1               5

<210> SEQ ID NO 6
<211> LENGTH: 8
<212> TYPE: PRT
<213> ORGANISM: Trichomonas vaginalis

<400> SEQUENCE: 6

Leu Lys Glu His Asp Met Leu Ala
1               5

<210> SEQ ID NO 7
<211> LENGTH: 8
<212> TYPE: PRT
<213> ORGANISM: Trichomonas vaginalis

<400> SEQUENCE: 7

Tyr Leu Gly Arg Val Thr Leu Ala
1               5

<210> SEQ ID NO 8
<211> LENGTH: 8
<212> TYPE: PRT
<213> ORGANISM: Trichomonas vaginalis

<400> SEQUENCE: 8

Arg Arg Ala Arg Ala Ala Gly Met
1               5

<210> SEQ ID NO 9
<211> LENGTH: 8
<212> TYPE: PRT
<213> ORGANISM: Trichomonas vaginalis

<400> SEQUENCE: 9

Lys Ser Ile Gly Gly Arg Leu Gly
1               5
```

<210> SEQ ID NO 10
<211> LENGTH: 11
<212> TYPE: PRT
<213> ORGANISM: Trichomonas vaginalis

<400> SEQUENCE: 10

Tyr Leu Leu Lys Tyr Asp Thr Ala His Arg Ala
1               5                   10

<210> SEQ ID NO 11
<211> LENGTH: 5
<212> TYPE: PRT
<213> ORGANISM: Trichomonas vaginalis

<400> SEQUENCE: 11

Tyr Lys Val Thr Tyr
1               5

<210> SEQ ID NO 12
<211> LENGTH: 8
<212> TYPE: PRT
<213> ORGANISM: Trichomonas vaginalis

<400> SEQUENCE: 12

Ala Ile Ile Thr Ala Ser Val Lys
1               5

<210> SEQ ID NO 13
<211> LENGTH: 8
<212> TYPE: PRT
<213> ORGANISM: Trichomonas vaginalis

<400> SEQUENCE: 13

Ala Gly Ala Arg Lys Tyr Ala Asn
1               5

<210> SEQ ID NO 14
<211> LENGTH: 11
<212> TYPE: PRT
<213> ORGANISM: Trichomonas vaginalis

<400> SEQUENCE: 14

Arg Lys Tyr Ala Asn Gln Thr Met Leu Arg Tyr
1               5                   10

<210> SEQ ID NO 15
<211> LENGTH: 11
<212> TYPE: PRT
<213> ORGANISM: Trichomonas vaginalis

<400> SEQUENCE: 15

Pro Ile Val Leu His Leu Asp His Gly Asp Ser
1               5                   10

<210> SEQ ID NO 16
<211> LENGTH: 11
<212> TYPE: PRT
<213> ORGANISM: Trichomonas vaginalis

<400> SEQUENCE: 16

Tyr Thr Arg Pro Glu Glu Val Gln Asp Phe Val
1               5                   10

<210> SEQ ID NO 17

```
<211> LENGTH: 11
<212> TYPE: PRT
<213> ORGANISM: Trichomonas vaginalis

<400> SEQUENCE: 17

Thr Ser His Gly Ala Tyr Lys Phe Pro Pro Gly
1               5                   10

<210> SEQ ID NO 18
<211> LENGTH: 11
<212> TYPE: PRT
<213> ORGANISM: Trichomonas vaginalis

<400> SEQUENCE: 18

Ser Ile Pro Gln Glu Tyr Val Glu Met Val Asn
1               5                   10

<210> SEQ ID NO 19
<211> LENGTH: 11
<212> TYPE: PRT
<213> ORGANISM: Trichomonas vaginalis

<400> SEQUENCE: 19

Arg Met Val Met Thr Gly Thr Ile Arg Arg Leu
1               5                   10

<210> SEQ ID NO 20
<211> LENGTH: 8
<212> TYPE: PRT
<213> ORGANISM: Trichomonas vaginalis

<400> SEQUENCE: 20

Arg Gln Tyr Leu Gly Glu Ala Arg
1               5

<210> SEQ ID NO 21
<211> LENGTH: 8
<212> TYPE: PRT
<213> ORGANISM: Trichomonas vaginalis

<400> SEQUENCE: 21

Ala Arg Thr Lys Leu Thr Glu Met
1               5

<210> SEQ ID NO 22
<211> LENGTH: 8
<212> TYPE: PRT
<213> ORGANISM: Trichomonas vaginalis

<400> SEQUENCE: 22

Ala Ile Val Lys Glu Cys Ile Ala
1               5

<210> SEQ ID NO 23
<211> LENGTH: 8
<212> TYPE: PRT
<213> ORGANISM: Trichomonas vaginalis

<400> SEQUENCE: 23

Tyr Leu Gly Arg Val Thr Leu Ala
1               5

<210> SEQ ID NO 24
<211> LENGTH: 8
<212> TYPE: PRT
```

```
<213> ORGANISM: Trichomonas vaginalis

<400> SEQUENCE: 24

Leu Ala Ala Arg Ser Ser Ala Pro
1               5

<210> SEQ ID NO 25
<211> LENGTH: 8
<212> TYPE: PRT
<213> ORGANISM: Trichomonas vaginalis

<400> SEQUENCE: 25

Asp Lys Ala Arg Tyr Gly Gly Lys
1               5

<210> SEQ ID NO 26
<211> LENGTH: 8
<212> TYPE: PRT
<213> ORGANISM: Trichomonas vaginalis

<400> SEQUENCE: 26

Thr Val Leu Lys Lys Asn Ile Gly
1               5

<210> SEQ ID NO 27
<211> LENGTH: 11
<212> TYPE: PRT
<213> ORGANISM: Trichomonas vaginalis

<400> SEQUENCE: 27

Val Pro Lys Lys Phe Lys Leu Pro Ser Pro Phe
1               5                   10

<210> SEQ ID NO 28
<211> LENGTH: 8
<212> TYPE: PRT
<213> ORGANISM: Trichomonas vaginalis

<400> SEQUENCE: 28

Gly Gly Leu Leu Val Lys Lys Tyr
1               5

<210> SEQ ID NO 29
<211> LENGTH: 8
<212> TYPE: PRT
<213> ORGANISM: Trichomonas vaginalis

<400> SEQUENCE: 29

Lys Tyr Gly Leu Ser Ala Lys Asn
1               5

<210> SEQ ID NO 30
<211> LENGTH: 8
<212> TYPE: PRT
<213> ORGANISM: Trichomonas vaginalis

<400> SEQUENCE: 30

Phe Tyr Asp Glu Glu Lys Lys Leu
1               5

<210> SEQ ID NO 31
<211> LENGTH: 11
<212> TYPE: PRT
<213> ORGANISM: Trichomonas vaginalis
```

```
<400> SEQUENCE: 31

Lys Lys His Pro Ala Ile Val Ser Ile Glu Asp
1               5                   10

<210> SEQ ID NO 32
<211> LENGTH: 11
<212> TYPE: PRT
<213> ORGANISM: Trichomonas vaginalis

<400> SEQUENCE: 32

Glu Asn Trp Thr Lys Leu Asn Ala Arg Leu Gly
1               5                   10

<210> SEQ ID NO 33
<211> LENGTH: 8
<212> TYPE: PRT
<213> ORGANISM: Trichomonas vaginalis

<400> SEQUENCE: 33

Asp Asp Leu Tyr Thr Thr Asn Pro
1               5

<210> SEQ ID NO 34
<211> LENGTH: 8
<212> TYPE: PRT
<213> ORGANISM: Trichomonas vaginalis

<400> SEQUENCE: 34

Glu Arg Ile Gln Lys Tyr Thr Arg
1               5

<210> SEQ ID NO 35
<211> LENGTH: 8
<212> TYPE: PRT
<213> ORGANISM: Trichomonas vaginalis

<400> SEQUENCE: 35

Leu Lys Glu His Asp Met Leu Ala
1               5

<210> SEQ ID NO 36
<211> LENGTH: 5
<212> TYPE: PRT
<213> ORGANISM: Trichomonas vaginalis

<400> SEQUENCE: 36

Leu Tyr Pro Lys Asp
1               5

<210> SEQ ID NO 37
<211> LENGTH: 11
<212> TYPE: PRT
<213> ORGANISM: Trichomonas vaginalis

<400> SEQUENCE: 37

Tyr Leu Leu Lys Tyr Asp Thr Ala His Arg Ala
1               5                   10

<210> SEQ ID NO 38
<211> LENGTH: 11
<212> TYPE: PRT
<213> ORGANISM: Trichomonas vaginalis

<400> SEQUENCE: 38
```

```
Phe Thr Val Gly Glu Gly Ala Asp Lys Trp Val
1               5                   10
```

<210> SEQ ID NO 39
<211> LENGTH: 8
<212> TYPE: PRT
<213> ORGANISM: Trichomonas vaginalis

<400> SEQUENCE: 39

```
Lys Ser Ile Gly Gly Arg Leu Gly
1               5
```

<210> SEQ ID NO 40
<211> LENGTH: 8
<212> TYPE: PRT
<213> ORGANISM: Trichomonas vaginalis

<400> SEQUENCE: 40

```
Ser Thr Gly Ile Phe Arg Thr Lys
1               5
```

<210> SEQ ID NO 41
<211> LENGTH: 8
<212> TYPE: PRT
<213> ORGANISM: Trichomonas vaginalis

<400> SEQUENCE: 41

```
Ala Glu Gly Lys Ile Lys Lys Asp
1               5
```

<210> SEQ ID NO 42
<211> LENGTH: 8
<212> TYPE: PRT
<213> ORGANISM: Trichomonas vaginalis

<400> SEQUENCE: 42

```
His Leu Val Ser Gly Ala Lys Lys
1               5
```

<210> SEQ ID NO 43
<211> LENGTH: 5
<212> TYPE: PRT
<213> ORGANISM: Trichomonas vaginalis

<400> SEQUENCE: 43

```
Ser Asn Ala Ser Cys
1               5
```

<210> SEQ ID NO 44
<211> LENGTH: 8
<212> TYPE: PRT
<213> ORGANISM: Trichomonas vaginalis

<400> SEQUENCE: 44

```
Asn Ala Phe Gly Ile Arg Asn Gly
1               5
```

<210> SEQ ID NO 45
<211> LENGTH: 8
<212> TYPE: PRT
<213> ORGANISM: Trichomonas vaginalis

<400> SEQUENCE: 45

```
Arg Arg Ala Arg Ala Ala Gly Met
1               5
```

```
<210> SEQ ID NO 46
<211> LENGTH: 8
<212> TYPE: PRT
<213> ORGANISM: Trichomonas vaginalis

<400> SEQUENCE: 46

Thr Ser Thr Gly Ala Ala Ile Ala
1               5

<210> SEQ ID NO 47
<211> LENGTH: 5
<212> TYPE: PRT
<213> ORGANISM: Trichomonas vaginalis

<400> SEQUENCE: 47

Cys His Gly Leu Pro
1               5

<210> SEQ ID NO 48
<211> LENGTH: 11
<212> TYPE: PRT
<213> ORGANISM: Trichomonas vaginalis

<400> SEQUENCE: 48

Ser Leu Val Asp Leu Thr Val Asn Val Asn Ala
1               5                   10

<210> SEQ ID NO 49
<211> LENGTH: 8
<212> TYPE: PRT
<213> ORGANISM: Trichomonas vaginalis

<400> SEQUENCE: 49

Val Ser Ser Asp Ile Ile Gly Cys
1               5

<210> SEQ ID NO 50
<211> LENGTH: 8
<212> TYPE: PRT
<213> ORGANISM: Trichomonas vaginalis

<400> SEQUENCE: 50

Gly Cys Gln Tyr Ser Ser Ile Val
1               5

<210> SEQ ID NO 51
<211> LENGTH: 11
<212> TYPE: PRT
<213> ORGANISM: Trichomonas vaginalis

<400> SEQUENCE: 51

Tyr Ser Ser Ile Val Asp Ala Leu Ser Thr Lys
1               5                   10

<210> SEQ ID NO 52
<211> LENGTH: 10
<212> TYPE: PRT
<213> ORGANISM: Trichomonas vaginalis

<400> SEQUENCE: 52

Val Ser Trp Tyr Asp Asn Glu Trp Met Tyr
1               5                   10
```

```
<210> SEQ ID NO 53
<211> LENGTH: 5
<212> TYPE: PRT
<213> ORGANISM: Trichomonas vaginalis

<400> SEQUENCE: 53

Cys Arg Cys Ala Asp
1               5

<210> SEQ ID NO 54
<211> LENGTH: 5
<212> TYPE: PRT
<213> ORGANISM: Trichomonas suis

<400> SEQUENCE: 54

Leu Tyr Pro Lys Glu
1               5

<210> SEQ ID NO 55
<211> LENGTH: 11
<212> TYPE: PRT
<213> ORGANISM: Trichomonas suis

<400> SEQUENCE: 55

His Leu Leu Asn Tyr Asp Ser Ala His Gln Arg
1               5                   10

<210> SEQ ID NO 56
<211> LENGTH: 11
<212> TYPE: PRT
<213> ORGANISM: Trichomonas suis

<400> SEQUENCE: 56

Phe Glu Val Gly Thr Gly Ser Asp Lys Trp Val
1               5                   10

<210> SEQ ID NO 57
<211> LENGTH: 8
<212> TYPE: PRT
<213> ORGANISM: Trichomonas suis

<400> SEQUENCE: 57

Lys Asn Leu Thr Gly Arg Leu Gly
1               5

<210> SEQ ID NO 58
<211> LENGTH: 8
<212> TYPE: PRT
<213> ORGANISM: Trichomonas suis

<400> SEQUENCE: 58

Ser Thr Gly Leu Phe Arg Thr His
1               5

<210> SEQ ID NO 59
<211> LENGTH: 8
<212> TYPE: PRT
<213> ORGANISM: Trichomonas suis

<400> SEQUENCE: 59

His Leu Leu Ala Gly Ala Lys Lys
1               5

<210> SEQ ID NO 60
<211> LENGTH: 5
```

```
<212> TYPE: PRT
<213> ORGANISM: Trichomonas suis

<400> SEQUENCE: 60

Ser Asn Ala Ser Cys
1               5

<210> SEQ ID NO 61
<211> LENGTH: 8
<212> TYPE: PRT
<213> ORGANISM: Trichomonas suis

<400> SEQUENCE: 61

Val Leu Asn Asp Thr Phe Gly Ile
1               5

<210> SEQ ID NO 62
<211> LENGTH: 8
<212> TYPE: PRT
<213> ORGANISM: Trichomonas suis

<400> SEQUENCE: 62

Arg Arg Ala Arg Ala Ala Gly Met
1               5

<210> SEQ ID NO 63
<211> LENGTH: 11
<212> TYPE: PRT
<213> ORGANISM: Trichomonas suis

<400> SEQUENCE: 63

Ile Thr Gly Ser Leu Val Asp Ile Thr Val Asn
1               5                   10

<210> SEQ ID NO 64
<211> LENGTH: 12
<212> TYPE: PRT
<213> ORGANISM: Trichomonas suis

<400> SEQUENCE: 64

His Ser Ser Ile Val Asp Ser Leu Ser Thr Met Val
1               5                   10

<210> SEQ ID NO 65
<211> LENGTH: 8
<212> TYPE: PRT
<213> ORGANISM: Trichomonas suis

<400> SEQUENCE: 65

Leu Val Lys Val Leu Ser Trp Tyr
1               5

<210> SEQ ID NO 66
<211> LENGTH: 11
<212> TYPE: PRT
<213> ORGANISM: Trichomonas vaginalis

<400> SEQUENCE: 66

Arg Arg Glu Gly Leu Leu Asp Asp Ala Trp Glu
1               5                   10

<210> SEQ ID NO 67
<211> LENGTH: 8
<212> TYPE: PRT
<213> ORGANISM: Trichomonas vaginalis
```

<400> SEQUENCE: 67

Ile Gln Phe Glu Thr Ile Glu Thr
1               5

<210> SEQ ID NO 68
<211> LENGTH: 5
<212> TYPE: PRT
<213> ORGANISM: Trichomonas vaginalis

<400> SEQUENCE: 68

Lys Gln Pro Lys Met
1               5

<210> SEQ ID NO 69
<211> LENGTH: 11
<212> TYPE: PRT
<213> ORGANISM: Trichomonas vaginalis

<400> SEQUENCE: 69

Tyr Glu His Val Ala Val Asn Asn Phe Thr Thr
1               5                   10

<210> SEQ ID NO 70
<211> LENGTH: 11
<212> TYPE: PRT
<213> ORGANISM: Trichomonas vaginalis

<400> SEQUENCE: 70

Tyr Val Tyr Leu Asp Pro Glu Asp Val Ile Asp
1               5                   10

<210> SEQ ID NO 71
<211> LENGTH: 5
<212> TYPE: PRT
<213> ORGANISM: Trichomonas vaginalis

<400> SEQUENCE: 71

Ala Asp Lys Ile Lys
1               5

<210> SEQ ID NO 72
<211> LENGTH: 8
<212> TYPE: PRT
<213> ORGANISM: Trichomonas vaginalis

<400> SEQUENCE: 72

Arg Gly Lys Leu Ala Ser Val Ile
1               5

<210> SEQ ID NO 73
<211> LENGTH: 8
<212> TYPE: PRT
<213> ORGANISM: Trichomonas vaginalis

<400> SEQUENCE: 73

Asn Arg Pro Ile Pro Glu Ile Pro
1               5

<210> SEQ ID NO 74
<211> LENGTH: 8
<212> TYPE: PRT
<213> ORGANISM: Trichomonas vaginalis

<400> SEQUENCE: 74

```
His His Ser Gln Leu Ile Thr Tyr
1               5

<210> SEQ ID NO 75
<211> LENGTH: 8
<212> TYPE: PRT
<213> ORGANISM: Trichomonas vaginalis

<400> SEQUENCE: 75

Tyr Asp Glu Ala Ile Ala Phe Lys
1               5

<210> SEQ ID NO 76
<211> LENGTH: 5
<212> TYPE: PRT
<213> ORGANISM: Trichomonas vaginalis

<400> SEQUENCE: 76

Lys Leu Asn Tyr Lys
1               5

<210> SEQ ID NO 77
<211> LENGTH: 5
<212> TYPE: PRT
<213> ORGANISM: Trichomonas vaginalis

<400> SEQUENCE: 77

Tyr Lys Val Thr Tyr
1               5

<210> SEQ ID NO 78
<211> LENGTH: 5
<212> TYPE: PRT
<213> ORGANISM: Trichomonas vaginalis

<400> SEQUENCE: 78

Lys Tyr Phe Asp Lys
1               5

<210> SEQ ID NO 79
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 79

Glu Gln Leu Gln Ala Ile Ile Thr Ala Ser Val Lys Thr Glu Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 80

Glu Ala His Ser Arg Pro Asp Tyr Val Thr Val Glu Gly Glu Leu
1               5                   10                  15

<210> SEQ ID NO 81
<211> LENGTH: 15
<212> TYPE: PRT
<213> ORGANISM: Artificial Sequence
```

```
<220> FEATURE:
<223> OTHER INFORMATION: Synthetic Peptide

<400> SEQUENCE: 81

Glu Asp Asp Val Lys Ala Glu Lys His Thr Tyr Thr Arg Pro Glu
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 82

His Thr Tyr Thr Arg Pro Glu Glu Val Gln Asp Phe Val Ser Lys
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 83

Ser Ser Ser Ile Pro Gln Glu Tyr Val Glu Met Val Asn Lys Tyr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 84

Asp Gly Arg Met Val Met Thr Gly Thr Ile Arg Arg Leu Phe Val
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 85

Leu Gly Glu Ala Arg Thr Lys Leu Thr Glu Met Tyr Met Arg Lys
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 86

Val Lys Tyr Leu Gly Arg Val Thr Leu Ala Ala Arg Ser Ser Ala
1               5                   10                  15

<210> SEQ ID NO 87
<211> LENGTH: 15
<212> TYPE: PRT
<213> ORGANISM: Artificial Sequence
<220> FEATURE:
```

<223> OTHER INFORMATION: Synthetic Peptide

<400> SEQUENCE: 87

Val Thr Leu Ala Ala Arg Ser Ser Ala Pro Ser Gly Ala Ser Thr
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 88

Thr Asp Gly Thr Val Leu Lys Lys Asn Ile Gly Gly Asn Ala Cys
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 89

Asp Lys Val Pro Lys Lys Phe Lys Leu Pro Ser Pro Phe Phe Asn
1               5                   10                  15

<210> SEQ ID NO 90
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 90

Lys Leu Gly Gly Leu Leu Val Lys Lys Tyr Gly Leu Ser Ala Lys
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 91

Ser Ser Glu Phe Tyr Asp Glu Glu Lys Lys Leu Tyr Glu Val Glu
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 92

Asp Tyr Glu Asn Trp Thr Lys Leu Asn Ala Arg Leu Gly Gln Arg
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 93

Leu Tyr Thr Thr Asn Pro Ile Thr Ile Lys Lys Gly Leu Glu Gly
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 94

Arg Ala Cys Arg Lys Leu Tyr Pro Lys Asp Ile Gln Val Val Ala
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 95

Gln Glu Phe Thr Val Gly Glu Gly Ala Asp Lys Trp Val Val Lys
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 96

Trp Val Val Lys Ser Ile Gly Gly Arg Leu Gly Pro Ser Gln Leu
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 97

Lys Asp Ala Glu Gly Lys Ile Lys Lys Asp Asp Gly Tyr Asp Gly His
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 98

Ala Leu Pro Lys Val Cys His Gly Leu Pro Pro Lys Ser Leu Asp
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: Synthetic Peptide

```
<400> SEQUENCE: 99

Glu Trp Met Tyr Ser Cys Arg Cys Ala Asp Ile Phe His Arg Leu
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 100

Ser Val Asn Arg His His Ser Gln Leu Ile Thr Tyr Ile Lys His
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 101

Ala Gln Pro Leu Tyr Asp Glu Ala Ile Ala Phe Lys Glu Glu Val
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 102

Phe Lys Asp Thr Phe Lys Tyr Phe Asp Lys Asp Lys Ser Asn Ser
1               5                   10                  15

<210> SEQ ID NO 103
<211> LENGTH: 8
<212> TYPE: PRT
<213> ORGANISM: Homo sapiens

<400> SEQUENCE: 103

Asp Lys Gln Arg Tyr Leu Gly Lys
1               5

<210> SEQ ID NO 104
<211> LENGTH: 8
<212> TYPE: PRT
<213> ORGANISM: Homo sapiens

<400> SEQUENCE: 104

Lys Tyr Gly Lys Asp Ala Thr Asn
1               5

<210> SEQ ID NO 105
<211> LENGTH: 8
<212> TYPE: PRT
<213> ORGANISM: Homo sapiens

<400> SEQUENCE: 105

Asp Asp Leu Thr Val Thr Asn Pro
1               5

<210> SEQ ID NO 106
```

```
<211> LENGTH: 8
<212> TYPE: PRT
<213> ORGANISM: Homo sapiens

<400> SEQUENCE: 106

Phe Val Lys Leu Ile Ser Trp Tyr
1               5

<210> SEQ ID NO 107
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 107

Ser Val Arg Arg Glu Gly Leu Leu Asp Asp Ala Trp Glu Lys Thr
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 108

Leu Ala Arg Gln Ile Gln Phe Glu Thr Ile Glu Thr Asp Phe Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 109

Pro Ser Lys Trp His Lys Gln Pro Lys Met Met Val Gln Lys Arg
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 110

Gln Gly Tyr Glu His Val Ala Val Asn Asn Phe Thr Thr Ser Trp
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 111

Gly Ile Tyr Val Tyr Leu Asp Pro Glu Asp Val Ile Asp Thr Thr
1               5                   10                  15

<210> SEQ ID NO 112
<211> LENGTH: 15
<212> TYPE: PRT
<213> ORGANISM: Artificial Sequence
```

```
<220> FEATURE:
<223> OTHER INFORMATION: Synthetic Peptide

<400> SEQUENCE: 112

Lys Ile Ala Ala Met Ala Asp Lys Ile Lys Arg Thr Val Ala Ile
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 113

Ile Pro Gly Ile Arg Gly Lys Leu Ala Ser Val Ile Ser Tyr Asn
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 114

Cys Lys Ser Gly Asn Arg Pro Ile Pro Glu Ile Pro Gln Gly Leu
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 115

Ser Val Asn Arg His His Ser Gln Leu Ile Thr Tyr Ile Lys His
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 116

Ala Gln Pro Leu Tyr Asp Glu Ala Ile Ala Phe Lys Glu Glu Val
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 117

Glu Leu Val Glu Phe Lys Leu Asn Tyr Lys Val Thr Tyr Thr Tyr
1               5                   10                  15

<210> SEQ ID NO 118
<211> LENGTH: 15
<212> TYPE: PRT
<213> ORGANISM: Artificial Sequence
<220> FEATURE:
```

<223> OTHER INFORMATION: Synthetic Peptide

<400> SEQUENCE: 118

Glu Phe Lys Leu Asn Tyr Lys Val Thr Tyr Thr Tyr Ser Asp Ala
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 119

Phe Lys Asp Thr Phe Lys Tyr Phe Asp Lys Asp Lys Ser Asn Ser
1               5                   10                  15

<210> SEQ ID NO 120
<211> LENGTH: 229
<212> TYPE: PRT
<213> ORGANISM: Artificial Sequence
<220> FEATURE:
<223> OTHER INFORMATION: Synthetic Peptide

<400> SEQUENCE: 120

Lys Lys Ser Val Arg Arg Glu Gly Leu Leu Asp Asp Ala Trp Glu Lys
1               5                   10                  15

Thr Lys Lys Leu Ala Arg Gln Ile Gln Phe Glu Thr Ile Glu Thr Asp
                20                  25                  30

Phe Glu Lys Lys Pro Ser Lys Trp His Lys Gln Pro Lys Met Met Val
            35                  40                  45

Gln Lys Arg Lys Gln Gly Tyr Glu His Val Ala Val Asn Asn Phe
        50                  55                  60

Thr Thr Ser Trp Lys Lys Gly Ile Tyr Val Tyr Leu Asp Pro Glu Asp
65                  70                  75                  80

Val Ile Asp Thr Thr Lys Lys Ile Ala Ala Met Ala Asp Lys Ile
                85                  90                  95

Lys Arg Thr Val Ala Ile Lys Lys Ile Pro Gly Ile Arg Gly Lys Leu
                100                 105                 110

Ala Ser Val Ile Ser Tyr Asn Lys Lys Cys Lys Ser Gly Asn Arg Pro
            115                 120                 125

Ile Pro Glu Ile Pro Gln Gly Leu Lys Lys Ser Val Asn Arg His His
        130                 135                 140

Ser Gln Leu Ile Thr Tyr Ile Lys His Lys Lys Ala Gln Pro Leu Tyr
145                 150                 155                 160

Asp Glu Ala Ile Ala Phe Lys Glu Val Lys Lys Glu Leu Val Glu
                165                 170                 175

Phe Lys Leu Asn Tyr Lys Val Thr Tyr Thr Tyr Lys Lys Glu Phe Lys
                180                 185                 190

Leu Asn Tyr Lys Val Thr Tyr Thr Tyr Ser Ala Lys Lys Phe Lys
            195                 200                 205

Asp Thr Phe Lys Tyr Phe Asp Lys Asp Lys Ser Asn Ser Lys Lys His
        210                 215                 220

His His His His
225

<210> SEQ ID NO 121
<211> LENGTH: 16
<212> TYPE: PRT

<213> ORGANISM: Treponema pallidum

<400> SEQUENCE: 121

Leu Ser Thr Ser Leu Leu Thr Thr Cys Asp Phe Thr G

```
Phe Ala Lys Lys Ile Gln Ser Glu Val Pro Ile Lys Lys Leu Leu
            20                  25                  30

Ile Gly Gly Ser Arg Gly Tyr Gly Glu Ile Lys Leu Glu Lys Arg
        35                  40                  45

Pro Asp Leu Tyr Ala Ala Val Gly Glu Lys Lys Ala Ser Gly Ala Lys
    50                  55                  60

Glu Glu Ala Glu Lys Lys Ala Ala Glu Gln Arg Ala Leu Leu Lys Lys
65                  70                  75                  80

Glu Val Glu Asp Val Pro Lys Val Val Glu Pro Ala Ser Glu Arg Glu
                85                  90                  95

Gly Gly Glu Arg Lys Lys His His His His His His
            100                 105

<210> SEQ ID NO 128
<211> LENGTH: 15
<212> TYPE: PRT
<213> ORGANISM: Neisseria gonorrhoeae

<400> SEQUENCE: 128

Phe Gly Ser Lys Ile Gly Phe Lys Gly Gln Glu Asp Leu Gly Asn
1               5                   10                  15

<210> SEQ ID NO 129
<211> LENGTH: 15
<212> TYPE: PRT
<213> ORGANISM: Neisseria gonorrhoeae

<400> SEQUENCE: 129

Gly Phe Ser Gly Ser Val Gln Tyr Ala Pro Lys Asp Asn Ser Gly
1               5                   10                  15

<210> SEQ ID NO 130
<211> LENGTH: 15
<212> TYPE: PRT
<213> ORGANISM: Neisseria gonorrhoeae

<400> SEQUENCE: 130

Gly Phe Phe Ala Gln Tyr Ala Gly Leu Phe Gln Arg Tyr Gly Glu
1               5                   10                  15

<210> SEQ ID NO 131
<211> LENGTH: 15
<212> TYPE: PRT
<213> ORGANISM: Neisseria gonorrhoeae

<400> SEQUENCE: 131

Val Glu Lys Leu Gln Val His Arg Leu Val Gly Gly Tyr Asp Asn
1               5                   10                  15

<210> SEQ ID NO 132
<211> LENGTH: 15
<212> TYPE: PRT
<213> ORGANISM: Neisseria gonorrhoeae

<400> SEQUENCE: 132

Asn Ser His Asn Ser Gln Thr Glu Val Ala Ala Thr Ala Ala Tyr
1               5                   10                  15

<210> SEQ ID NO 133
<211> LENGTH: 15
<212> TYPE: PRT
<213> ORGANISM: Neisseria gonorrhoeae
```

<400> SEQUENCE: 133

Asn Thr Tyr Asp Gln Val Val Gly Ala Glu Tyr Asp Phe Ser
1               5                   10                  15

<210> SEQ ID NO 134
<211> LENGTH: 110
<212> TYPE: PRT
<213> ORGANISM: Artificial Sequence
<220> FEATURE:
<223> OTHER INFORMATION: Synthetic Peptide

<400> SEQUENCE: 134

Lys Lys Phe Gly Ser Lys Ile Gly Phe Lys Gly Gln Glu Asp Leu Gly
1               5                   10                  15

Asn Lys Lys Gly Phe Ser Gly Ser Val Gln Tyr Ala Pro Lys Asp Asn
            20                  25                  30

Ser Gly Lys Lys Gly Phe Phe Ala Gln Tyr Ala Gly Leu Phe Gln Arg
        35                  40                  45

Tyr Gly Glu Lys Lys Val Glu Lys Leu Gln Val His Arg Leu Val Gly
    50                  55                  60

Gly Tyr Asp Asn Lys Lys Asn Ser His Asn Ser Gln Thr Glu Val Ala
65                  70                  75                  80

Ala Thr Ala Ala Tyr Lys Lys Asn Thr Tyr Asp Gln Val Val Val Gly
                85                  90                  95

Ala Glu Tyr Asp Phe Ser Lys Lys His His His His His
            100                 105                 110

<210> SEQ ID NO 135
<211> LENGTH: 11
<212> TYPE: PRT
<213> ORGANISM: Trichomonas vaginalis

<400> SEQUENCE: 135

Asn Gly Gly Lys His Ala Gly Gly Asn Leu Lys
1               5                   10

<210> SEQ ID NO 136
<211> LENGTH: 11
<212> TYPE: PRT
<213> ORGANISM: Trichomonas vaginalis

<400> SEQUENCE: 136

Gln Leu Arg Met Val Ala Glu Val Tyr Gln Lys
1               5                   10

<210> SEQ ID NO 137
<211> LENGTH: 8
<212> TYPE: PRT
<213> ORGANISM: Trichomonas vaginalis

<400> SEQUENCE: 137

Asn Ala Arg Leu Gly Gln Arg Val
1               5

<210> SEQ ID NO 138
<211> LENGTH: 8
<212> TYPE: PRT
<213> ORGANISM: Trichomonas vaginalis

<400> SEQUENCE: 138

Asn Pro Ile Thr Ile Lys Lys Gly

```
<210> SEQ ID NO 139
<211> LENGTH: 5
<212> TYPE: PRT
<213> ORGANISM: Trichomonas vaginalis

<400> SEQUENCE: 139

Ser Gln Leu Pro Trp
1               5

<210> SEQ ID NO 140
<211> LENGTH: 8
<212> TYPE: PRT
<213> ORGANISM: Trichomonas vaginalis

<400> SEQUENCE: 140

Thr Leu Asn Asn Ala Phe Gly Ile
1               5

<210> SEQ ID NO 141
<211> LENGTH: 11
<212> TYPE: PRT
<213> ORGANISM: Trichomonas vaginalis

<400> SEQUENCE: 141

Lys Asp Leu Arg Arg Ala Arg Ala Ala Gly Met
1               5                   10

<210> SEQ ID NO 142
<211> LENGTH: 11
<212> TYPE: PRT
<213> ORGANISM: Trichomonas vaginalis

<400> SEQUENCE: 142

Ile Thr Gly Ser Leu Val Asp Leu Thr Val Asn
1               5                   10

<210> SEQ ID NO 143
<211> LENGTH: 8
<212> TYPE: PRT
<213> ORGANISM: Trichomonas vaginalis

<400> SEQUENCE: 143

Leu Val Lys Val Leu Ser Trp Tyr
1               5

<210> SEQ ID NO 144
<211> LENGTH: 8
<212> TYPE: PRT
<213> ORGANISM: Trichomonas vaginalis

<400> SEQUENCE: 144

Leu Val Lys Val Leu Ser Trp Tyr
1               5

<210> SEQ ID NO 145
<211> LENGTH: 111
<212> TYPE: PRT
<213> ORGANISM: Artificial Sequence
<220> FEATURE:
<223> OTHER INFORMATION: Synthetic Peptide

<400> SEQUENCE: 145

Met Lys Lys Gln Glu Phe Thr Val Gly Glu Gly Ala Asp Lys Trp Val
```

-continued

```
                1               5                  10                 15
Val Lys Lys Lys Trp Val Val Lys Ser Ile Gly Gly Arg Leu Gly Pro
                20                 25                 30

Ser Gln Leu Lys Lys Ser Ser Glu Phe Tyr Asp Glu Lys Lys Leu
                35                 40                 45

Tyr Glu Val Glu Lys Lys Asp Tyr Glu Asn Trp Thr Lys Leu Asn Ala
 50                 55                 60

Arg Leu Gly Gln Arg Lys Lys His Thr Tyr Thr Arg Pro Glu Val
 65                 70                 75                 80

Gln Asp Phe Val Ser Lys Lys Ser Ser Ile Pro Gln Glu Tyr
                85                 90                 95

Val Glu Met Val Asn Lys Tyr Lys Lys His His His His His His
                100                105                110
```

<210> SEQ ID NO 146
<211> LENGTH: 229
<212> TYPE: PRT
<213> ORGANISM: Artificial Sequence
<220> FEATURE:
<223> OTHER INFORMATION: Synthetic Peptide

<400> SEQUENCE: 146

```
Gly Gly Ser Val Arg Arg Glu Gly Leu Leu Asp Asp Ala Trp Glu Lys
 1               5                  10                 15

Thr Gly Gly Leu Ala Arg Gln Ile Gln Phe Glu Thr Ile Glu Thr Asp
                20                 25                 30

Phe Glu Gly Gly Pro Ser Lys Trp His Lys Gln Pro Lys Met Met Val
                35                 40                 45

Gln Lys Arg Gly Gly Gln Gly Tyr Glu His Val Ala Val Asn Asn Phe
 50                 55                 60

Thr Thr Ser Trp Gly Gly Ile Tyr Val Tyr Leu Asp Pro Glu Asp
 65                 70                 75                 80

Val Ile Asp Thr Thr Gly Gly Lys Ile Ala Ala Met Ala Asp Lys Ile
                85                 90                 95

Lys Arg Thr Val Ala Ile Gly Gly Ile Pro Gly Ile Arg Gly Lys Leu
                100                105                110

Ala Ser Val Ile Ser Tyr Asn Gly Gly Cys Lys Ser Gly Asn Arg Pro
                115                120                125

Ile Pro Glu Ile Pro Gln Gly Leu Gly Gly Ser Val Asn Arg His His
 130                135                140

Ser Gln Leu Ile Thr Tyr Ile Lys His Gly Gly Ala Gln Pro Leu Tyr
145                 150                155                160

Asp Glu Ala Ile Ala Phe Lys Glu Glu Val Gly Gly Glu Leu Val Glu
                165                170                175

Phe Lys Leu Asn Tyr Lys Val Thr Tyr Thr Tyr Gly Gly Glu Phe Lys
                180                185                190

Leu Asn Tyr Lys Val Thr Tyr Thr Tyr Ser Asp Ala Gly Gly Phe Lys
                195                200                205

Asp Thr Phe Lys Tyr Phe Asp Lys Asp Lys Ser Asn Ser Gly Gly His
                210                215                220

His His His His His
225
```

<210> SEQ ID NO 147
<211> LENGTH: 328
<212> TYPE: PRT

<213> ORGANISM: Trichomonas vaginalis

<400> SEQUENCE: 147

Met Ala Val Ser Tyr Lys Ser Leu Gly Leu Val Asn Ser Lys Asp Ile
1               5                   10                  15

Phe Ala Lys Ala Val Asn Gly Gly Tyr Ala Ile Pro Gly Tyr Asn Phe
            20                  25                  30

Ser Asn Leu Glu Gln Leu Gln Ala Ile Ile Thr Ala Ser Val Lys Thr
        35                  40                  45

Glu Ser Pro Val Ile Leu Gln Val Ser Ala Gly Ala Arg Lys Tyr Ala
50                  55                  60

Asn Gln Thr Met Leu Arg Tyr Met Ala Gln Gly Ala Ala Glu Phe Ala
65                  70                  75                  80

Lys Glu Ile His Pro Glu His Lys Leu Ile Pro Ile Val Leu His Leu
                85                  90                  95

Asp His Gly Asp Ser Phe Glu Leu Cys Lys Ser Cys Ile Asp Leu Gly
            100                 105                 110

Phe Ser Ser Val Met Ile Asp Gly Ser His His Pro Tyr Asp Glu Asn
        115                 120                 125

Val Ala Leu Thr Lys Lys Val Val Glu Tyr Ala His Ser Arg Pro Asp
130                 135                 140

Tyr Val Thr Val Glu Gly Glu Leu Gly Val Leu Ala Gly Val Glu Asp
145                 150                 155                 160

Asp Val Lys Ala Glu Lys His Thr Tyr Thr Arg Pro Glu Glu Val Gln
                165                 170                 175

Asp Phe Val Ser Lys Thr Gly Val Asp Ser Leu Ala Ile Ala Ile Gly
            180                 185                 190

Thr Ser His Gly Ala Tyr Lys Phe Pro Pro Gly Thr Lys Ala Glu Ile
        195                 200                 205

Arg Leu Asp Ile Leu His Glu Ile Gly Lys Lys Leu Pro Gly Phe Pro
210                 215                 220

Ile Val Leu His Gly Ser Ser Ser Ile Pro Gln Glu Tyr Val Glu Met
225                 230                 235                 240

Val Asn Lys Tyr Gly Gly His Met Pro Glu Ala Val Gly Ile Pro Glu
                245                 250                 255

His Gln Leu Arg Glu Ala Ser Lys Ser Ala Val Cys Lys Ile Asn Ile
            260                 265                 270

Asp Ser Asp Gly Arg Met Val Met Thr Gly Thr Ile Arg Arg Leu Phe
        275                 280                 285

Val Glu His Pro Asp Trp Phe Asp Pro Arg Gln Tyr Leu Gly Glu Ala
290                 295                 300

Arg Thr Lys Leu Thr Glu Met Tyr Met Arg Lys Asp Gln Glu Val Leu
305                 310                 315                 320

Gly Cys Ala Gly His Ala Phe Asp
                325

<210> SEQ ID NO 148
<211> LENGTH: 332
<212> TYPE: PRT
<213> ORGANISM: Treponema pallidum

<400> SEQUENCE: 148

Met Thr Ser Tyr Lys Ala Leu Gly Leu Val Asn Thr Lys Asp Leu Phe
1               5                   10                  15

Ala Lys Ala Val Lys Gly Gly Tyr Ala Ile Pro Ala Tyr Asn Phe Asn

```
            20                  25                  30
Asn Leu Glu Gln Leu Gln Ala Ile Ile Gln Ala Cys Val Glu Thr Arg
        35                  40                  45

Ser Pro Val Ile Leu Gln Val Ser Ser Gly Ala Arg Lys Tyr Ala Asn
    50                  55                  60

Ala Thr Leu Leu Arg Asn Met Ala Arg Gly Ala Val Glu Tyr Ala His
65                  70                  75                  80

Glu Leu Gly Val Asp Ile Pro Ile Val Leu His Leu Asp His Gly Asp
                85                  90                  95

Ser Leu Glu Leu Cys Ile Asp Cys Ile Glu Ser Gly Phe Ser Ser Val
            100                 105                 110

Met Ile Asp Gly Ser Ala Leu Pro Tyr Asp Glu Asn Val Ala Leu Ser
        115                 120                 125

Arg Lys Val Cys Glu Tyr Ala His Ala Arg Ala Asp Tyr Val Thr Val
    130                 135                 140

Glu Gly Glu Leu Gly Val Leu Ala Gly Val Glu Asp Val Val Ala
145                 150                 155                 160

Glu Lys Ser His Tyr Thr Met Pro Asp Glu Val Glu Asp Phe Val Lys
                165                 170                 175

Lys Thr Gly Val Asp Ser Leu Ala Ile Ser Ile Gly Thr Ser His Gly
            180                 185                 190

Arg Ala Lys Phe Thr Pro Glu Gln Cys Thr Arg Asn Ala Asp Gly Val
        195                 200                 205

Leu Ile Pro Pro Pro Leu Arg Phe Asp Ile Leu Ala Glu Ile Glu Lys
    210                 215                 220

Arg Ile Pro Gly Phe Pro Ile Val Leu His Gly Ala Ser Ser Val Pro
225                 230                 235                 240

Val Glu Tyr Val Arg Glu Val Glu Arg Tyr Gly Gly Asn Leu Pro Asp
                245                 250                 255

Ser Val Gly Ile Pro Glu Glu Gln Leu Arg Lys Ala Ala Lys Ser Ala
            260                 265                 270

Val Cys Lys Val Asn Ile Asp Ser Asp Gly Arg Leu Ala Met Thr Ala
        275                 280                 285

Ala Ile Arg Arg Val Leu Thr Thr Lys Val Asp Glu Phe Asp Pro Arg
    290                 295                 300

Lys Tyr Leu Gly Pro Ala Arg Asp Glu Leu Lys Lys Leu Tyr Met His
305                 310                 315                 320

Lys Asn Lys Glu Val Leu Gly Ser Ala Gly Arg Ala
                325                 330

<210> SEQ ID NO 149
<211> LENGTH: 354
<212> TYPE: PRT
<213> ORGANISM: Neisseria gonorrhoeae

<400> SEQUENCE: 149

Met Ala Leu Val Ser Met Arg Gln Leu Leu Asp His Ala Ala Glu Asn
1               5                   10                  15

Ser Tyr Gly Leu Pro Ala Phe Asn Val Asn Asn Leu Glu Gln Met Arg
            20                  25                  30

Ala Ile Met Glu Ala Ala Asp Gln Val Asn Ala Pro Val Ile Val Gln
        35                  40                  45

Ala Ser Ala Gly Ala Arg Lys Tyr Ala Gly Ala Pro Phe Leu Arg His
    50                  55                  60
```

Leu Ile Leu Ala Ala Val Glu Glu Phe Pro His Ile Pro Val Val Met
65                  70                  75                  80

His Gln Asp His Gly Ala Ser Pro Asp Val Cys Gln Arg Ser Ile Gln
                85                  90                  95

Leu Gly Phe Ser Ser Val Met Met Asp Gly Ser Leu Leu Glu Asp Gly
            100                 105                 110

Lys Thr Pro Ser Ser Tyr Glu Tyr Asn Val Asn Ala Thr Arg Thr Val
            115                 120                 125

Val Asn Phe Ser His Ala Cys Gly Val Ser Val Glu Gly Glu Ile Gly
            130                 135                 140

Val Leu Gly Asn Leu Glu Thr Gly Glu Ala Gly Glu Glu Asp Gly Val
145                 150                 155                 160

Gly Ala Ala Gly Lys Leu Ser His Asp Gln Met Leu Thr Ser Val Glu
                165                 170                 175

Asp Ala Val Arg Phe Val Lys Asp Thr Gly Val Asp Ala Leu Ala Ile
            180                 185                 190

Ala Val Gly Thr Ser His Gly Ala Tyr Lys Phe Thr Arg Pro Pro Thr
            195                 200                 205

Gly Asp Val Leu Arg Ile Asp Arg Ile Lys Glu Ile His Gln Ala Leu
210                 215                 220

Pro Asn Thr His Ile Val Met His Gly Ser Ser Val Pro Gln Glu
225                 230                 235                 240

Trp Leu Lys Val Ile Asn Glu Tyr Gly Gly Asn Ile Gly Glu Thr Tyr
                245                 250                 255

Gly Val Pro Val Glu Glu Ile Val Glu Gly Ile Lys His Gly Val Arg
            260                 265                 270

Lys Val Asn Ile Asp Thr Asp Leu Arg Leu Ala Ser Thr Gly Ala Val
            275                 280                 285

Arg Arg Tyr Leu Ala Glu Asn Pro Ser Asp Phe Asp Pro Arg Lys Tyr
            290                 295                 300

Leu Gly Lys Thr Ile Glu Ala Met Lys Gln Ile Cys Leu Asp Arg Tyr
305                 310                 315                 320

Leu Ala Phe Gly Cys Glu Gly Gln Ala Gly Lys Ile Lys Pro Val Ser
                325                 330                 335

Leu Glu Lys Met Ala Ser Arg Tyr Ala Lys Gly Glu Leu Asn Gln Ile
            340                 345                 350

Val Lys

<210> SEQ ID NO 150
<211> LENGTH: 293
<212> TYPE: PRT
<213> ORGANISM: Streptococcus pyogenes

<400> SEQUENCE: 150

Met Ala Ile Val Ser Ala Glu Lys Phe Val Gln Ala Ala Arg Glu Asn
1               5                   10                  15

Gly Tyr Ala Val Gly Gly Phe Asn Thr Asn Asn Leu Glu Trp Thr Gln
            20                  25                  30

Ala Ile Leu Arg Ala Ala Glu Ala Lys Gln Ala Pro Val Leu Ile Gln
        35                  40                  45

Thr Ser Met Gly Ala Ala Lys Tyr Met Gly Gly Tyr Lys Val Cys Gln
    50                  55                  60

Ser Leu Ile Thr Asn Leu Val Glu Ser Met Gly Ile Thr Val Pro Val
65                  70                  75                  80

```
Ala Ile His Leu Asp His Gly His Tyr Glu Asp Ala Leu Glu Cys Ile
             85                  90                  95

Glu Val Gly Tyr Thr Ser Ile Met Phe Asp Gly Ser His Leu Pro Val
            100                 105                 110

Glu Glu Asn Leu Ala Lys Thr Ala Glu Val Val Lys Ile Ala His Ala
            115                 120                 125

Lys Gly Val Ser Val Glu Ala Glu Val Gly Thr Ile Gly Gly Glu Glu
            130                 135             140

Asp Gly Ile Ile Gly Lys Gly Glu Leu Ala Pro Ile Glu Asp Ala Lys
145             150                 155                 160

Ala Met Val Glu Thr Gly Ile Asp Phe Leu Ala Gly Ile Gly Asn
            165                 170                 175

Ile His Gly Pro Tyr Pro Glu Asn Trp Glu Gly Leu Ala Leu Asp His
            180                 185                 190

Leu Glu Lys Leu Thr Ala Ala Val Pro Gly Phe Pro Ile Val Leu His
            195                 200                 205

Gly Gly Ser Gly Ile Pro Asp Asp Gln Ile Lys Glu Ala Ile Arg Leu
            210                 215                 220

Gly Val Ala Lys Val Asn Val Asn Thr Glu Ser Gln Ile Ala Phe Ser
225             230                 235                 240

Asn Ala Thr Arg Glu Phe Ala Arg Asn Tyr Glu Ala Asn Glu Ala Glu
            245                 250                 255

Tyr Asp Gly Lys Lys Leu Phe Asp Pro Arg Lys Phe Leu Ala Pro Gly
            260                 265                 270

Met Lys Ala Val Gln Gly Ala Val Glu Glu Arg Ile Asp Val Phe Gly
            275                 280                 285

Ser Ala Asn Lys Ala
            290

<210> SEQ ID NO 151
<211> LENGTH: 293
<212> TYPE: PRT
<213> ORGANISM: Streptococcus pneumoniae

<400> SEQUENCE: 151

Met Ala Ile Val Ser Ala Glu Lys Phe Val Gln Ala Ala Arg Asp Asn
1               5                   10                  15

Gly Tyr Ala Val Gly Gly Phe Asn Thr Asn Asn Leu Glu Trp Thr Gln
            20                  25                  30

Ala Ile Leu Arg Ala Ala Glu Ala Lys Lys Ala Pro Val Leu Ile Gln
            35                  40                  45

Thr Ser Met Gly Ala Ala Lys Tyr Met Gly Gly Tyr Lys Val Ala Arg
        50                  55                  60

Asn Leu Ile Ala Asn Leu Val Glu Ser Met Gly Ile Thr Val Pro Val
65                  70                  75                  80

Ala Ile His Leu Asp His Gly His Tyr Glu Asp Ala Leu Glu Cys Ile
            85                  90                  95

Glu Val Gly Tyr Thr Ser Ile Met Phe Asp Gly Ser His Leu Pro Val
            100                 105                 110

Glu Glu Asn Leu Lys Leu Ala Lys Glu Val Val Glu Lys Ala His Ala
            115                 120                 125

Lys Gly Ile Ser Val Glu Ala Glu Val Gly Thr Ile Gly Gly Glu Glu
            130                 135                 140

Asp Gly Ile Ile Gly Lys Gly Glu Leu Ala Pro Ile Glu Asp Ala Lys
145             150                 155                 160
```

```
Ala Met Val Glu Thr Gly Ile Asp Phe Leu Ala Ala Gly Ile Gly Asn
            165                 170                 175

Ile His Gly Pro Tyr Pro Val Asn Trp Glu Gly Leu Asp Leu Asp His
            180                 185                 190

Leu Gln Lys Leu Thr Glu Ala Leu Pro Gly Phe Pro Ile Val Leu His
            195                 200                 205

Gly Gly Ser Gly Ile Pro Asp Glu Gln Ile Gln Ala Ala Ile Lys Leu
            210                 215                 220

Gly Val Ala Lys Val Asn Val Asn Thr Glu Cys Gln Ile Ala Phe Ala
225                 230                 235                 240

Asn Ala Thr Arg Lys Phe Ala Arg Asp Tyr Glu Ala Asn Glu Ala Glu
            245                 250                 255

Tyr Asp Lys Lys Lys Leu Phe Asp Pro Arg Lys Phe Leu Ala Asp Gly
            260                 265                 270

Val Lys Ala Ile Gln Ala Ser Val Glu Glu Arg Ile Asp Val Phe Gly
            275                 280                 285

Ser Glu Gly Lys Ala
            290

<210> SEQ ID NO 152
<211> LENGTH: 286
<212> TYPE: PRT
<213> ORGANISM: Staphylococcus aureus

<400> SEQUENCE: 152

Met Pro Leu Val Ser Met Lys Glu Met Leu Ile Asp Ala Lys Glu Asn
1               5                   10                  15

Gly Tyr Ala Val Gly Gln Tyr Asn Ile Asn Asn Leu Glu Phe Thr Gln
            20                  25                  30

Ala Ile Leu Glu Ala Ser Gln Glu Glu Asn Ala Pro Val Ile Leu Gly
            35                  40                  45

Val Ser Glu Gly Ala Ala Arg Tyr Met Ser Gly Phe Tyr Thr Ile Val
        50                  55                  60

Lys Met Val Glu Gly Leu Met His Asp Leu Asn Ile Thr Ile Pro Val
65                  70                  75                  80

Ala Ile His Leu Asp His Gly Ser Ser Phe Glu Lys Cys Lys Glu Ala
            85                  90                  95

Ile Asp Ala Gly Phe Thr Ser Val Met Ile Asp Ala Ser His Ser Pro
            100                 105                 110

Phe Glu Glu Asn Val Ala Thr Thr Lys Lys Val Val Glu Tyr Ala His
            115                 120                 125

Glu Lys Gly Val Ser Val Glu Ala Glu Leu Gly Thr Val Gly Gly Gln
            130                 135                 140

Glu Asp Asp Val Val Ala Asp Gly Ile Ile Tyr Ala Asp Pro Lys Glu
145                 150                 155                 160

Cys Gln Glu Leu Val Glu Lys Thr Gly Ile Asp Ala Leu Ala Pro Ala
            165                 170                 175

Leu Gly Ser Val His Gly Pro Tyr Lys Gly Glu Pro Lys Leu Gly Phe
            180                 185                 190

Lys Glu Met Glu Glu Ile Gly Leu Ser Thr Gly Leu Pro Leu Val Leu
            195                 200                 205

His Gly Gly Thr Gly Ile Pro Thr Lys Asp Ile Gln Lys Ala Ile Pro
            210                 215                 220

Phe Gly Thr Ala Lys Ile Asn Val Asn Thr Glu Asn Gln Ile Ala Ser
```

```
          225                 230                 235                 240
Ala Lys Ala Val Arg Asp Val Leu Asn Asn Asp Lys Glu Val Tyr Asp
                    245                 250                 255

Pro Arg Lys Tyr Leu Gly Pro Ala Arg Glu Ala Ile Lys Glu Thr Val
            260                 265                 270

Lys Gly Lys Ile Lys Glu Phe Gly Thr Ser Asn Arg Ala Lys
            275                 280                 285

<210> SEQ ID NO 153
<211> LENGTH: 350
<212> TYPE: PRT
<213> ORGANISM: Escherichia coli

<400> SEQUENCE: 153

Met Thr Asp Ile Ala Gln Leu Leu Gly Lys Asp Ala Asp Asn Leu Leu
1               5                   10                  15

Gln His Arg Cys Met Thr Ile Pro Ser Asp Gln Leu Tyr Leu Pro Gly
                20                  25                  30

His Asp Tyr Val Asp Arg Val Met Ile Asp Asn Asn Arg Pro Pro Ala
            35                  40                  45

Val Leu Arg Asn Met Gln Thr Leu Tyr Asn Thr Gly Arg Leu Ala Gly
        50                  55                  60

Thr Gly Tyr Leu Ser Ile Leu Pro Val Asp Gln Gly Val Glu His Ser
65                  70                  75                  80

Ala Gly Ala Ser Phe Ala Ala Asn Pro Leu Tyr Phe Asp Pro Lys Asn
                85                  90                  95

Ile Val Glu Leu Ala Ile Glu Ala Gly Cys Asn Cys Val Ala Ser Thr
            100                 105                 110

Tyr Gly Val Leu Ala Ser Val Ser Arg Arg Tyr Ala His Arg Ile Pro
        115                 120                 125

Phe Leu Val Lys Leu Asn His Asn Glu Thr Leu Ser Tyr Pro Asn Thr
130                 135                 140

Tyr Asp Gln Thr Leu Tyr Ala Ser Val Glu Gln Ala Phe Asn Met Gly
145                 150                 155                 160

Ala Val Ala Val Gly Ala Thr Ile Tyr Phe Gly Ser Glu Glu Ser Arg
                165                 170                 175

Arg Gln Ile Glu Glu Ile Ser Ala Ala Phe Glu Arg Ala His Glu Leu
            180                 185                 190

Gly Met Val Thr Val Leu Trp Ala Tyr Leu Arg Asn Ser Ala Phe Lys
        195                 200                 205

Lys Asp Gly Val Asp Tyr His Val Ser Ala Asp Leu Thr Gly Gln Ala
210                 215                 220

Asn His Leu Ala Ala Thr Ile Gly Ala Asp Ile Val Lys Gln Lys Met
225                 230                 235                 240

Ala Glu Asn Asn Gly Gly Tyr Lys Ala Ile Asn Tyr Gly Tyr Thr Asp
                245                 250                 255

Asp Arg Val Tyr Ser Lys Leu Thr Ser Glu Asn Pro Ile Asp Leu Val
            260                 265                 270

Arg Tyr Gln Leu Ala Asn Cys Tyr Met Gly Arg Ala Gly Leu Ile Asn
        275                 280                 285

Ser Gly Gly Ala Ala Gly Gly Glu Thr Asp Leu Ser Asp Ala Val Arg
290                 295                 300

Thr Ala Val Ile Asn Lys Arg Ala Gly Gly Met Gly Leu Ile Leu Gly
305                 310                 315                 320
```

```
Arg Lys Ala Phe Lys Ser Met Ala Asp Gly Val Lys Leu Ile Asn
                325                 330                 335

Ala Val Gln Asp Val Tyr Leu Asp Ser Lys Ile Thr Ile Ala
            340                 345                 350

<210> SEQ ID NO 154
<211> LENGTH: 359
<212> TYPE: PRT
<213> ORGANISM: Candida albicans

<400> SEQUENCE: 154

Met Ala Pro Pro Ala Val Leu Ser Lys Ser Gly Val Ile Tyr Gly Lys
1               5                   10                  15

Asp Val Lys Asp Leu Phe Asp Tyr Ala Gln Glu Lys Gly Phe Ala Ile
            20                  25                  30

Pro Ala Ile Asn Val Thr Ser Ser Thr Val Val Ala Ala Leu Glu
        35                  40                  45

Ala Ala Arg Asp Asn Lys Ala Pro Ile Ile Leu Gln Thr Ser Gln Gly
50                  55                  60

Gly Ala Ala Tyr Phe Ala Gly Lys Gly Val Asp Asn Lys Asp Gln Ala
65                  70                  75                  80

Ala Ser Ile Ala Gly Ser Ile Ala Ala His Tyr Ile Arg Ala Ile
                85                  90                  95

Ala Pro Thr Tyr Gly Ile Pro Val Val Leu His Thr Asp His Cys Ala
            100                 105                 110

Lys Lys Leu Leu Pro Trp Phe Asp Gly Met Leu Lys Ala Asp Glu Glu
        115                 120                 125

Phe Phe Ala Lys Thr Gly Thr Pro Leu Phe Ser Ser His Met Leu Asp
130                 135                 140

Leu Ser Glu Glu Thr Asp Asp Glu Asn Ile Ala Thr Cys Ala Lys Tyr
145                 150                 155                 160

Phe Glu Arg Met Ala Lys Met Gly Gln Trp Leu Glu Met Glu Ile Gly
                165                 170                 175

Ile Thr Gly Gly Glu Glu Asp Gly Val Asn Asn Glu His Val Glu Lys
            180                 185                 190

Asp Ala Leu Tyr Thr Ser Pro Glu Thr Val Phe Ala Val Tyr Glu Ser
        195                 200                 205

Leu His Lys Ile Ser Pro Asn Phe Ser Ile Ala Ala Phe Gly Asn
210                 215                 220

Val His Gly Val Tyr Lys Pro Gly Asn Val Gln Leu Arg Pro Glu Ile
225                 230                 235                 240

Leu Gly Asp His Gln Val Tyr Ala Lys Lys Gln Ile Gly Thr Asp Ala
                245                 250                 255

Lys His Pro Leu Tyr Leu Val Phe His Gly Gly Ser Gly Ser Thr Gln
            260                 265                 270

Glu Glu Phe Asn Thr Ala Ile Lys Asn Gly Val Val Lys Val Asn Leu
        275                 280                 285

Asp Thr Asp Cys Gln Tyr Ala Tyr Leu Thr Gly Ile Arg Asp Tyr Val
290                 295                 300

Thr Asn Lys Ile Glu Tyr Leu Lys Ala Pro Val Gly Asn Pro Glu Gly
305                 310                 315                 320

Ala Asp Lys Pro Asn Lys Lys Tyr Phe Asp Pro Arg Val Trp Val Arg
                325                 330                 335

Glu Gly Glu Lys Thr Met Ser Lys Arg Ile Ala Glu Ala Leu Asp Ile
            340                 345                 350
```

Phe His Thr Lys Gly Gln Leu
                355

<210> SEQ ID NO 155
<211> LENGTH: 359
<212> TYPE: PRT
<213> ORGANISM: Saccharomyces cerevisiae

<400> SEQUENCE: 155

Met Gly Val Glu Gln Ile Leu Lys Arg Lys Thr Gly Val Ile Val Gly
1               5                   10                  15

Glu Asp Val His Asn Leu Phe Thr Tyr Ala Lys Glu His Lys Phe Ala
            20                  25                  30

Ile Pro Ala Ile Asn Val Thr Ser Ser Thr Ala Val Ala Ala Leu
        35                  40                  45

Glu Ala Ala Arg Asp Ser Lys Ser Pro Ile Ile Leu Gln Thr Ser Asn
    50                  55                  60

Gly Gly Ala Ala Tyr Phe Ala Gly Lys Gly Ile Ser Asn Glu Gly Gln
65                  70                  75                  80

Asn Ala Ser Ile Lys Gly Ala Ile Ala Ala His Tyr Ile Arg Ser
                85                  90                  95

Ile Ala Pro Ala Tyr Gly Ile Pro Val Val Leu His Ser Asp His Cys
            100                 105                 110

Ala Lys Lys Leu Leu Pro Trp Phe Asp Gly Met Leu Glu Ala Asp Glu
        115                 120                 125

Ala Tyr Phe Lys Glu His Gly Glu Pro Leu Phe Ser Ser His Met Leu
    130                 135                 140

Asp Leu Ser Glu Glu Thr Asp Glu Glu Asn Ile Ser Thr Cys Val Lys
145                 150                 155                 160

Tyr Phe Lys Arg Met Ala Ala Met Asp Gln Trp Leu Glu Met Glu Ile
                165                 170                 175

Gly Ile Thr Gly Gly Glu Glu Asp Gly Val Asn Asn Glu Asn Ala Asp
            180                 185                 190

Lys Glu Asp Leu Tyr Thr Lys Pro Glu Gln Val Tyr Asn Val Tyr Lys
        195                 200                 205

Ala Leu His Pro Ile Ser Pro Asn Phe Ser Ile Ala Ala Phe Gly
    210                 215                 220

Asn Cys His Gly Leu Tyr Ala Gly Asp Ile Ala Leu Arg Pro Glu Ile
225                 230                 235                 240

Leu Ala Glu His Gln Lys Tyr Thr Arg Glu Gln Val Gly Cys Lys Glu
                245                 250                 255

Glu Lys Pro Leu Phe Leu Val Phe His Gly Gly Ser Gly Ser Thr Val
            260                 265                 270

Gln Glu Phe His Thr Gly Ile Asp Asn Gly Val Val Lys Val Asn Leu
        275                 280                 285

Asp Thr Asp Cys Gln Tyr Ala Tyr Leu Thr Gly Ile Arg Asp Tyr Val
    290                 295                 300

Leu Asn Lys Lys Asp Tyr Ile Met Ser Pro Val Gly Asn Pro Glu Gly
305                 310                 315                 320

Pro Glu Lys Pro Asn Lys Lys Phe Phe Asp Pro Arg Val Trp Val Arg
                325                 330                 335

Glu Gly Glu Lys Thr Met Gly Ala Lys Ile Thr Lys Ser Leu Glu Thr
            340                 345                 350

Phe Arg Thr Thr Asn Thr Leu

<210> SEQ ID NO 156
<211> LENGTH: 931
<212> TYPE: PRT
<213> ORGANISM: Trichomonas vaginalis

<400> SEQUENCE: 156

Met Ser Val Arg Arg Glu Gly Leu Leu Asp Asp Ala Trp Glu Lys Thr
1               5                   10                  15

Gln Ile Lys Val Phe Ser Arg Trp Val Gln Lys Gln Leu Leu Ala Arg
            20                  25                  30

Gln Ile Gln Phe Glu Thr Ile Glu Thr Asp Phe Glu Asp Gly Thr Lys
        35                  40                  45

Leu Leu Asn Leu Leu Glu Ile Ile Gly Lys Glu Pro Met Pro Ser Lys
    50                  55                  60

Trp His Lys Gln Pro Lys Met Met Val Gln Lys Arg Glu Asn Val Asp
65                  70                  75                  80

Leu Ala Leu Lys Tyr Ile Asn Glu Val Lys Lys Ile Arg Thr Val Gly
                85                  90                  95

Ile Gly Ala Asp Asp Ile Ile Asn Lys Asn Leu Lys Leu Thr Leu Gly
            100                 105                 110

Leu Thr Trp Thr Cys Ile Asn Lys Phe Met Ile Glu Glu Ile Ser Val
        115                 120                 125

Glu Glu Ala Thr Ala Arg Asp Ala Leu Leu Leu Trp Ala Lys Lys Asn
    130                 135                 140

Thr Gln Gly Tyr Glu His Val Ala Val Asn Asn Phe Thr Thr Ser Trp
145                 150                 155                 160

Asn Thr Gly Leu Ala Phe Ala Ala Leu Ile Asn Lys Phe Arg Pro Asn
                165                 170                 175

Leu Leu Asp Tyr Ser Ala Leu Asp Tyr Asn Asp His Lys Gly Ala Cys
            180                 185                 190

Glu Lys Ala Phe Ala Ala Cys Lys Glu Leu Gly Ile Tyr Val Tyr Leu
        195                 200                 205

Asp Pro Glu Asp Val Ile Asp Thr Thr Pro Asp Glu Lys Ser Val Val
    210                 215                 220

Thr Gln Val Ala Glu Phe Phe His Phe Phe Ala Ser Glu Ser Lys Ile
225                 230                 235                 240

Ala Ala Met Ala Asp Lys Ile Lys Arg Thr Val Ala Ile Gln Lys Gln
                245                 250                 255

Ile Asp Glu Leu Lys Asn Thr Tyr Ile Glu Asp Ala Lys Ala Ala Ile
            260                 265                 270

Glu Lys Met Thr Val Glu Asp Glu Lys Leu Lys Ala Asp Asp Tyr Glu
        275                 280                 285

Lys Thr Ile Pro Gly Ile Arg Gly Lys Leu Ala Ser Val Ile Ser Tyr
    290                 295                 300

Asn Arg Asp Ile Arg Pro Glu Ile Val Asp His Arg Ala Lys Ala Met
305                 310                 315                 320

Arg Ser Trp Ala Ala Leu Val Thr Lys Cys Lys Ser Gly Asn Arg Pro
                325                 330                 335

Ile Pro Glu Ile Pro Gln Gly Leu Glu Pro Glu Ala Leu Thr Asn Lys
            340                 345                 350

Phe Asn Glu Ile Glu Gln Thr Ser Thr Thr Arg Arg Asp Glu Leu Thr
        355                 360                 365

-continued

```
Gln Glu Leu Asn Asp Met Ile Lys Lys Val Glu Asp Phe Met Ala
    370                 375                 380
Lys Cys Met Asp Ile Ile Asn Lys Cys Asp Ala Ile His Glu Val
385                 390                 395                 400
Lys Thr Ile Glu Gly Thr Thr Ala Glu Lys Lys Asp Lys Val Glu Gln
                405                 410                 415
Lys Leu His Glu Ala Glu Asp Leu Gln Pro Ala Leu Ala Glu Leu Thr
            420                 425                 430
Pro Leu Phe Gln Glu Leu Val Glu Leu Arg Ile Asn Thr Leu Ser Ser
        435                 440                 445
Gln Thr Asp Asp Ser Val Asn Arg His His Ser Gln Leu Ile Thr Tyr
    450                 455                 460
Ile Lys His Leu Leu Glu Gln Leu Asn Gly Lys Leu Phe Glu Thr
465                 470                 475                 480
Asn Glu Ala Arg Ile Asn Glu Tyr Asn Ala Leu Ala Gln Pro Leu Tyr
                485                 490                 495
Asp Glu Ala Ile Ala Phe Lys Glu Val Leu Ala Ile Ser Gly Glu
            500                 505                 510
Leu Arg Glu Arg Arg Thr Gln Phe Leu Ala Lys Gln Ala Glu Ala Pro
        515                 520                 525
Thr Lys Arg Glu His Val Asn Glu Ile Asp Pro Ile Phe Asp Gly Leu
    530                 535                 540
Glu Lys Asp Ser Leu His Leu Arg Val Asn His Ser Pro Thr Glu Ile
545                 550                 555                 560
Arg Asn Val Tyr Ala Val Thr Leu Gln His Ile Ile Thr Glu Leu Asn
                565                 570                 575
Lys Ile Phe Glu Glu Met Val Ala Asn Phe Asp Ala Thr Ala Val Pro
            580                 585                 590
Ile Ile Asp Gly Ile Thr Ala Leu Val Thr Ser Ser His Gln Ile Pro
        595                 600                 605
Gly Asp Ala Ala Ala Val Lys Ala Gln Val Glu Glu Asn Leu Ala Ser
    610                 615                 620
Leu Asp Gly Phe Ala Glu Lys Ile Gln Ala Leu Gln Asp Pro Tyr Asn
625                 630                 635                 640
Glu Leu Val Glu Phe Lys Leu Asn Tyr Lys Val Thr Tyr Thr Tyr Ser
                645                 650                 655
Asp Ala Thr Gly Glu Leu Asp Gln Ala Arg Leu Asp Leu Lys Gln Ile
            660                 665                 670
Ile Leu Ala Lys Lys Thr Phe Leu Glu Glu Glu Arg Lys Ala Arg
        675                 680                 685
Ile Asn Asn Tyr Thr Val Lys Ala Asp Glu His Met Asn Glu Ala His
    690                 695                 700
Ala Leu Asp Gly Lys Ile Asn Ser Val Asp Gly Glu Leu Glu Pro Lys
705                 710                 715                 720
Arg Gln Lys Leu Tyr Glu Val Arg Glu Val Asn Ala Lys Lys Glu
                725                 730                 735
Lys Ala Ala Glu Glu Leu Thr Pro Ile Tyr Glu Asp Leu Glu Lys Asp
            740                 745                 750
Gln Leu His Leu Glu Ile Thr Thr Pro Ala Ser Ile Asn Ile Phe
        755                 760                 765
Phe Glu Asn Leu Ile Ala His Ile Asp Thr Leu Val Lys Glu Ile Asp
    770                 775                 780
Ala Ala Ile Ala Ala Ala Lys Gly Leu Glu Ile Ser Glu Glu Glu Leu
```

```
                785                 790                 795                 800
Asn Glu Phe Lys Asp Thr Phe Lys Tyr Phe Asp Lys Asp Lys Ser Asn
                    805                 810                 815

Ser Leu Glu Tyr Phe Glu Leu Lys Ala Cys Leu Thr Ala Leu Gly Glu
                    820                 825                 830

Asp Ile Thr Asp Gly Gln Ala Lys Glu Tyr Cys Lys Lys Tyr Asn Ser
                    835                 840                 845

Lys Gly Glu Gly Thr Ala Leu Glu Phe Asp Asp Tyr Val Arg Phe Met
                    850                 855                 860

Leu Asp His Phe Ser Lys Ala Glu Thr Thr Glu Thr Thr Met Glu Ala
865                 870                 875                 880

Phe Lys Ala Ile Ala Gln Asn Gln Pro Val Leu Thr Asp Ala Gln Leu
                    885                 890                 895

Asp Gln Tyr Phe Ser Ala Glu Asp Ala Ala Tyr Leu Arg Ser Gln Leu
                    900                 905                 910

Lys Gln Gly Glu Asn Gly Tyr Glu Phe Ala Asp Trp Val Asn Ser Leu
                    915                 920                 925

Tyr Asn His
    930

<210> SEQ ID NO 157
<211> LENGTH: 894
<212> TYPE: PRT
<213> ORGANISM: Homo sapiens

<400> SEQUENCE: 157

Met Asn Gln Ile Glu Pro Gly Val Gln Tyr Asn Tyr Val Tyr Asp Glu
1               5                   10                  15

Asp Glu Tyr Met Ile Gln Glu Glu Glu Trp Asp Arg Asp Leu Leu Leu
                20                  25                  30

Asp Pro Ala Trp Glu Lys Gln Gln Arg Lys Thr Phe Thr Ala Trp Cys
            35                  40                  45

Asn Ser His Leu Arg Lys Ala Gly Thr Gln Ile Glu Asn Ile Glu Glu
        50                  55                  60

Asp Phe Arg Asn Gly Leu Lys Leu Met Leu Leu Leu Glu Val Ile Ser
65                  70                  75                  80

Gly Glu Arg Leu Pro Lys Pro Asp Arg Gly Lys Met Arg Phe His Lys
                85                  90                  95

Ile Ala Asn Val Asn Lys Ala Leu Asp Tyr Ile Ala Ser Lys Gly Val
                    100                 105                 110

Lys Leu Val Ser Ile Gly Ala Glu Glu Ile Val Asp Gly Asn Val Lys
                115                 120                 125

Met Thr Leu Gly Met Ile Trp Thr Ile Ile Leu Arg Phe Ala Ile Gln
130                 135                 140

Asp Ile Ser Val Glu Glu Thr Ser Ala Lys Glu Gly Leu Leu Leu Trp
145                 150                 155                 160

Cys Gln Arg Lys Thr Ala Pro Tyr Arg Asn Val Asn Ile Gln Asn Phe
                    165                 170                 175

His Thr Ser Trp Lys Asp Gly Leu Gly Leu Cys Ala Leu Ile His Arg
                    180                 185                 190

His Arg Pro Asp Leu Ile Asp Tyr Ser Lys Leu Asn Lys Asp Asp Pro
                195                 200                 205

Ile Gly Asn Ile Asn Leu Ala Met Glu Ile Ala Glu Lys His Leu Asp
            210                 215                 220
```

```
Ile Pro Lys Met Leu Asp Ala Glu Asp Ile Val Asn Thr Pro Lys Pro
225                 230                 235                 240

Asp Glu Arg Ala Ile Met Thr Tyr Val Ser Cys Phe Tyr His Ala Phe
            245                 250                 255

Ala Gly Ala Glu Gln Ala Glu Thr Ala Ala Asn Arg Ile Cys Lys Val
        260                 265                 270

Leu Ala Val Asn Gln Glu Asn Glu Arg Leu Met Glu Glu Tyr Glu Arg
    275                 280                 285

Leu Ala Ser Glu Leu Leu Glu Trp Ile Arg Arg Thr Ile Pro Trp Leu
    290                 295                 300

Glu Asn Arg Thr Pro Glu Lys Thr Met Gln Ala Met Gln Lys Lys Leu
305                 310                 315                 320

Glu Asp Phe Arg Asp Tyr Arg Arg Lys His Lys Pro Pro Lys Val Gln
                325                 330                 335

Glu Lys Cys Gln Leu Glu Ile Asn Phe Asn Thr Leu Gln Thr Lys Leu
            340                 345                 350

Arg Ile Ser Asn Arg Pro Ala Phe Met Pro Ser Glu Gly Lys Met Val
        355                 360                 365

Ser Asp Ile Ala Gly Ala Trp Gln Arg Leu Glu Gln Ala Glu Lys Gly
    370                 375                 380

Tyr Glu Glu Trp Leu Leu Asn Glu Ile Arg Arg Leu Glu Arg Leu Glu
385                 390                 395                 400

His Leu Ala Glu Lys Phe Arg Gln Lys Ala Ser Thr His Glu Thr Trp
                405                 410                 415

Ala Tyr Gly Lys Glu Gln Ile Leu Leu Gln Lys Asp Tyr Glu Ser Ala
            420                 425                 430

Ser Leu Thr Glu Val Arg Ala Leu Leu Arg Lys His Glu Ala Phe Glu
        435                 440                 445

Ser Asp Leu Ala Ala His Gln Asp Arg Val Glu Gln Ile Ala Ala Ile
    450                 455                 460

Ala Gln Glu Leu Asn Glu Leu Asp Tyr His Asp Ala Val Asn Val Asn
465                 470                 475                 480

Asp Arg Cys Gln Lys Ile Cys Asp Gln Trp Asp Arg Leu Gly Thr Leu
                485                 490                 495

Thr Gln Lys Arg Arg Glu Ala Leu Glu Arg Met Glu Lys Leu Leu Glu
            500                 505                 510

Thr Ile Asp Gln Leu His Leu Glu Phe Ala Lys Arg Ala Ala Pro Phe
        515                 520                 525

Asn Asn Trp Met Glu Gly Ala Met Glu Asp Leu Gln Asp Met Phe Ile
    530                 535                 540

Val His Ser Ile Glu Glu Ile Gln Ser Leu Ile Thr Ala His Glu Gln
545                 550                 555                 560

Phe Lys Ala Thr Leu Pro Glu Ala Asp Gly Glu Arg Gln Ser Ile Met
                565                 570                 575

Ala Ile Gln Asn Glu Val Glu Lys Val Ile Gln Ser Tyr Asn Ile Arg
            580                 585                 590

Ile Ser Ser Ser Asn Pro Tyr Ser Thr Val Thr Met Asp Glu Leu Arg
        595                 600                 605

Thr Lys Trp Asp Lys Val Lys Gln Leu Val Pro Ile Arg Asp Gln Ser
    610                 615                 620

Leu Gln Glu Glu Leu Ala Arg Gln His Ala Asn Glu Arg Leu Arg Arg
625                 630                 635                 640

Gln Phe Ala Ala Gln Ala Asn Ala Ile Gly Pro Trp Ile Gln Asn Lys
```

```
            645                 650                 655
Met Glu Glu Ile Ala Arg Ser Ser Ile Gln Ile Thr Gly Ala Leu Glu
            660                 665                 670

Asp Gln Met Asn Gln Leu Lys Gln Tyr Glu His Asn Ile Ile Asn Tyr
            675                 680                 685

Lys Asn Asn Ile Asp Lys Leu Glu Gly Asp His Gln Leu Ile Gln Glu
            690                 695                 700

Ala Leu Val Phe Asp Asn Lys His Thr Asn Tyr Thr Met Glu His Ile
705                 710                 715                 720

Arg Val Gly Trp Glu Leu Leu Leu Thr Thr Ile Ala Arg Thr Ile Asn
                    725                 730                 735

Glu Val Glu Thr Gln Ile Leu Thr Arg Asp Ala Lys Gly Ile Thr Gln
                    740                 745                 750

Glu Gln Met Asn Glu Phe Arg Ala Ser Phe Asn His Phe Asp Arg Arg
            755                 760                 765

Lys Asn Gly Leu Met Asp His Glu Asp Phe Arg Ala Cys Leu Ile Ser
            770                 775                 780

Met Gly Tyr Asp Leu Gly Glu Ala Glu Phe Ala Arg Ile Met Thr Leu
785                 790                 795                 800

Val Asp Pro Asn Gly Gln Gly Thr Val Thr Phe Gln Ser Phe Ile Asp
                    805                 810                 815

Phe Met Thr Arg Glu Thr Ala Asp Thr Asp Thr Ala Glu Gln Val Ile
                    820                 825                 830

Ala Ser Phe Arg Ile Leu Ala Ser Asp Lys Pro Tyr Ile Leu Ala Glu
            835                 840                 845

Glu Leu Arg Arg Glu Leu Pro Pro Asp Gln Ala Gln Tyr Cys Ile Lys
            850                 855                 860

Arg Met Pro Ala Tyr Ser Gly Pro Gly Ser Val Pro Gly Ala Leu Asp
865                 870                 875                 880

Tyr Ala Ala Phe Ser Ser Ala Leu Tyr Gly Glu Ser Asp Leu
                    885                 890

<210> SEQ ID NO 158
<211> LENGTH: 482
<212> TYPE: PRT
<213> ORGANISM: Treponema pallidum

<400> SEQUENCE: 158

Met Arg Arg Arg Val Cys Thr Val Val Arg Ala Val Cys Leu Leu
1               5                   10                  15

Ser Thr Ser Leu Leu Thr Thr Cys Asp Phe Thr Gly Ile Phe Ala Ala
                20                  25                  30

Ile Gln Ser Glu Val Pro Ile Lys Thr Pro Ser Ile Pro Gly Ala Ile
            35                  40                  45

Tyr Gly Leu Val Lys Ala Gly Ser Lys Leu Tyr Ala Thr Asn Gly Arg
        50                  55                  60

Leu Trp Glu Lys Glu Leu Asn Gly Thr Glu Ser Trp Gln Lys Val Ser
65                  70                  75                  80

Ser Ser Ser Val Pro Thr Asp Ser Asp Lys Lys Val Met Ser Ile Ala
                    85                  90                  95

Thr Asp Gly Thr Asn Phe Val Leu Ala Cys Val Pro Gly Thr Gly Val
                100                 105                 110

Tyr Lys His Cys Val Asn Gly Ala Val Gly Ser Ser Thr Ala Ala
            115                 120                 125
```

```
Ser Gly Ser Thr Glu Thr Cys Ser Asn His Ala Thr Leu Val Gly Gly
    130                 135                 140

Thr Ser Thr Pro Phe Trp Ile Val Pro Gly Thr Gly Ser Asn Gly
145                 150                 155                 160

Asn Cys Gly Cys Gly Ala Gly Gly Gly Ser Ser Ser Ser Ser
                165                 170                 175

Ser Cys Ile His Ile Trp Leu Val Pro Ala Gly Thr Gly Ser Asn Gly
                180                 185                 190

Asn Cys Gly Cys Gly Ala Gly Gly Gly Ser Ser Ser Ser Ser
                195                 200                 205

Ser Cys Ile His Ile Lys Lys Glu Asp Thr Gly Glu Gln Phe Leu Asp
210                 215                 220

Arg Gly Glu Gly Tyr Val Val Thr Thr Lys His Leu Tyr Thr Lys Asn
225                 230                 235                 240

Gly Ser Ser Ser Ala Gly Pro Ala Pro Cys Pro Gly Gly Gly Gly
                245                 250                 255

Ser Ser Gly Gly Gly Ser Ser Gln Tyr Thr Lys Asp Ser Cys Phe
                260                 265                 270

Phe Ser Thr Pro Ile Leu Ala Ser Val Ser Asp Gly Cys Tyr His Tyr
    275                 280                 285

Ile Leu Thr Lys Glu Lys Val Tyr Cys Arg Lys Gln Asn Ala Ala Ser
    290                 295                 300

Ser Ala Ala Ser Ser Pro Ala Ser Cys Pro Ser Ser Pro Ser Ser Ser
305                 310                 315                 320

Ser Ser Ser Ser Thr Asn Ala Gly Cys Glu Val Glu His Gly Val Asp
                325                 330                 335

Asp Pro Leu Cys Leu Ala Ile Phe Lys His Asn Gly Cys Glu Tyr Leu
                340                 345                 350

Leu Ile Gly Gly Ser Arg Gly Tyr Gly Glu Ile Lys Leu Glu Ala Ser
                355                 360                 365

Ser Ser Gly Thr Asn Gly Thr Cys Met Arg Leu Lys Glu Ser Asn Val
                370                 375                 380

His Lys Ser Pro Asp Gln Trp Asp Glu Ser Ser Pro Thr Pro Lys Ala
385                 390                 395                 400

Ser Ala Glu Gln Tyr Arg Gly Thr Val Gly Arg Phe Ala Val Gln Lys
                405                 410                 415

Ile Tyr Val Val Glu Lys Asn Gly Gly Asn Gly Val Ala Ala Gly
                420                 425                 430

Gly Ala Gly Cys Pro Ala Ser Ala Ser Ser Thr Asn Gly Thr Ala Gly
                435                 440                 445

Ser Thr Gln Arg Pro Asp Leu Tyr Ala Ala Val Gly Glu Ser Ser Asp
450                 455                 460

Ser Tyr Thr Gly Leu Trp Lys Phe Asp Thr Thr Thr Cys Ser Trp Asn
465                 470                 475                 480

Arg Glu

<210> SEQ ID NO 159
<211> LENGTH: 345
<212> TYPE: PRT
<213> ORGANISM: Treponema pallidum

<400> SEQUENCE: 159

Met Asn Ala His Thr Leu Val Tyr Ser Gly Val Ala Leu Ala Cys Ala
1               5                   10                  15
```

```
Ala Met Leu Gly Ser Cys Ala Ser Gly Ala Lys Glu Glu Ala Lys
            20                  25                  30

Lys Ala Ala Glu Gln Arg Ala Leu Leu Val Glu Ser Ala His Ala Asp
        35                  40                  45

Arg Arg Leu Met Glu Ala Arg Ile Gly Ala Gln Glu Ser Gly Ala Asp
    50                  55                  60

Thr Gln His Pro Glu Leu Phe Ser Gln Ile Gln Asp Val Glu Arg Gln
65                  70                  75                  80

Ser Thr Asp Ala Lys Ile Glu Gly Asp Leu Lys Ala Ala Gly Val
                85                  90                  95

Ala Ser Glu Ala Ala Asp Lys Tyr Glu Ile Leu Arg Asn Arg Val Glu
            100                 105                 110

Val Ala Asp Leu Gln Ser Lys Ile Gln Thr His Gln Leu Ala Gln Tyr
        115                 120                 125

Asp Gly Asp Ser Ala Asn Ala Ala Glu Glu Ser Trp Lys Lys Ala Leu
    130                 135                 140

Glu Leu Tyr Glu Thr Asp Ser Ala Gln Cys Leu Gln Ser Thr Val Glu
145                 150                 155                 160

Ala Leu Glu Ser Tyr Arg Lys Val Ala His Glu Gly Phe Gly Arg Leu
                165                 170                 175

Leu Pro Asp Met Lys Ala Arg Ala Gly Ala Ala Lys Thr Asp Val Gly
            180                 185                 190

Gly Leu Lys Val Ala Val Glu Leu Arg Pro Gln Leu Glu Glu Ala Asp
        195                 200                 205

Ser Gln Tyr Gln Glu Ala Arg Glu Ala Glu Val Asn Ala Arg Ala
    210                 215                 220

Lys Ala Phe Ser Gly Tyr His Arg Ala Leu Glu Ile Tyr Thr Glu Leu
225                 230                 235                 240

Gly Lys Val Val Arg Leu Lys Lys Thr Glu Ala Glu Lys Ala Leu Gln
                245                 250                 255

Ser Ala Lys Thr Lys Gln Lys Ala Ser Ser Asp Leu Ala Arg Ser Ala
            260                 265                 270

Asp Lys Ser Ala Pro Leu Pro Glu Asn Ala Gln Gly Phe Ser Lys Glu
        275                 280                 285

Pro Ile Glu Val Glu Pro Leu Pro Asn Asp Arg Leu Asn Thr Thr Gln
    290                 295                 300

Ala Asp Glu Ser Ala Pro Ile Pro Ile Ser Asp Thr Ser Ser Pro Ser
305                 310                 315                 320

Arg Val Gln Ser Arg Gly Val Glu Asp Gly Gly Arg Ser Pro Lys Ser
                325                 330                 335

Ser Met Asn Glu Glu Gly Ala Ser Arg
            340                 345

<210> SEQ ID NO 160
<211> LENGTH: 320
<212> TYPE: PRT
<213> ORGANISM: Treponema pallidum

<400> SEQUENCE: 160

Arg Asp Pro Leu Ser Ser Pro Pro Ala Gly His Thr Pro Glu Tyr
1               5                   10                  15

Arg Asp Thr Val Ile Phe Asp Asp Pro Arg Leu Val Ser Pro Leu Ser
            20                  25                  30

Arg Glu Val Glu Asp Ala Pro Lys Val Val Glu Pro Ala Ser Glu Arg
        35                  40                  45
```

```
Glu Gly Gly Glu Arg Glu Val Glu Asp Ala Pro Lys Val Val Glu Pro
    50                  55                  60

Ala Ser Glu Arg Glu Gly Gly Glu Arg Glu Val Glu Asp Val Pro Lys
65                  70                  75                  80

Val Val Glu Pro Ala Ser Glu Arg Glu Gly Gly Glu Arg Glu Val Glu
                85                  90                  95

Asp Ala Pro Lys Val Val Glu Pro Ala Ser Glu Arg Glu Gly Gly Glu
                100                 105                 110

Arg Glu Val Glu Asp Val Pro Lys Val Val Glu Pro Ala Ser Glu Arg
        115                 120                 125

Glu Gly Gly Glu Arg Glu Val Glu Asp Val Pro Lys Val Val Glu Pro
    130                 135                 140

Ala Ser Glu Arg Glu Gly Gly Glu Arg Glu Val Glu Asp Ala Pro Lys
145                 150                 155                 160

Val Val Glu Pro Ala Ser Glu Arg Glu Gly Gly Glu Arg Glu Val Glu
                165                 170                 175

Asp Ala Pro Lys Val Val Glu Pro Ala Ser Glu Arg Glu Gly Gly Glu
                180                 185                 190

Arg Glu Val Glu Asp Val Pro Lys Val Val Glu Pro Ala Ser Glu Arg
        195                 200                 205

Glu Gly Gly Glu Arg Glu Val Glu Asp Val Pro Lys Val Val Glu Pro
    210                 215                 220

Ala Ser Glu Arg Glu Gly Gly Glu Arg Glu Val Glu Asp Val Pro Lys
225                 230                 235                 240

Val Val Glu Pro Ala Ser Glu Arg Glu Gly Gly Glu Arg Glu Val Glu
                245                 250                 255

Asp Val Pro Lys Val Val Glu Pro Ala Ser Glu Arg Glu Gly Gly Glu
                260                 265                 270

Arg Glu Val Glu Asp Val Pro Gly Val Val Glu Pro Ala Ser Gly His
        275                 280                 285

Glu Gly Gly Glu Arg Glu Val Glu Asp Val Pro Gly Val Val Glu Pro
    290                 295                 300

Ala Ser Gly His Glu Gly Gly Glu Arg Glu Val Ala Ser Gln His Thr
305                 310                 315                 320

<210> SEQ ID NO 161
<211> LENGTH: 348
<212> TYPE: PRT
<213> ORGANISM: Neisseria gonorrhoeae

<400> SEQUENCE: 161

Met Lys Lys Ser Leu Ile Ala Leu Thr Leu Ala Ala Leu Pro Val Ala
1               5                   10                  15

Ala Thr Ala Asp Val Thr Leu Tyr Gly Ala Ile Lys Ala Gly Val Gln
                20                  25                  30

Thr Tyr Arg Ser Val Glu His Arg Glu Gly Lys Val Val Gly Val Glu
        35                  40                  45

Thr Gly Ser Glu Ile Ser Asp Phe Gly Ser Lys Ile Gly Phe Lys Gly
    50                  55                  60

Gln Glu Asp Leu Gly Asn Gly Leu Lys Ala Val Trp Gln Leu Glu Gln
65                  70                  75                  80

Gly Ala Ser Val Ala Gly Thr Asn Thr Gly Trp Gly Asn Lys Gln Ser
                85                  90                  95

Phe Val Gly Leu Lys Gly Gly Phe Gly Thr Ile Arg Val Gly Ser Leu
```

```
            100                 105                 110
Asn Ser Pro Leu Lys Asn Thr Gly Ala Asn Val Asn Ala Trp Glu Ser
            115                 120                 125

Gly Lys Tyr Thr Gly Glu Phe Leu Glu Ile Ser Lys Met Ala Gly Arg
        130                 135                 140

Glu His Arg Tyr Leu Ser Ala Arg Tyr Asp Ser Pro Glu Phe Ala Gly
145                 150                 155                 160

Phe Ser Gly Ser Val Gln Tyr Ala Pro Lys Asp Asn Ser Gly Ser Asn
                165                 170                 175

Gly Glu Ser Tyr His Val Gly Leu Asn Tyr Arg Asn Gly Phe Phe
            180                 185                 190

Ala Gln Tyr Ala Gly Leu Phe Gln Arg Tyr Gly Glu Gly Thr Lys Lys
        195                 200                 205

Ile Glu Tyr Asn Ser Gln Ser Tyr Ser Ile Pro Ser Leu Phe Val Glu
            210                 215                 220

Lys Leu Gln Val His Arg Leu Val Gly Gly Tyr Asp Asn Asn Ala Leu
225                 230                 235                 240

Tyr Ala Ser Val Ala Ala Gln Gln Asp Ala Lys Leu Tyr Gly Thr
                245                 250                 255

Trp Arg Ala Asn Ser His Asn Ser Gln Thr Glu Val Ala Ala Thr Ala
        260                 265                 270

Ala Tyr Arg Phe Gly Asn Leu Thr Pro Arg Val Ser Tyr Ala His Gly
            275                 280                 285

Phe Lys Gly Ser Val His Ser Ala Asp Tyr Asp Asn Thr Tyr Asp Gln
        290                 295                 300

Val Val Val Gly Ala Glu Tyr Asp Phe Ser Lys Arg Thr Ser Ala Leu
305                 310                 315                 320

Val Ser Ala Gly Trp Leu Gln Glu Gly Lys Gly Ala Glu Lys Ile Val
                325                 330                 335

Ser Thr Ala Ser Ala Val Val Leu Arg His Lys Phe
            340                 345

<210> SEQ ID NO 162
<211> LENGTH: 11
<212> TYPE: PRT
<213> ORGANISM: Trichomonas vaginalis

<400> SEQUENCE: 162

Asn Glu Leu Val Glu Phe Lys Leu Asn Tyr Lys
1               5                   10

<210> SEQ ID NO 163
<211> LENGTH: 11
<212> TYPE: PRT
<213> ORGANISM: Trichomonas vaginalis

<400> SEQUENCE: 163

Val Glu Phe Lys Leu Asn Tyr Lys Val Thr Tyr
1               5                   10

<210> SEQ ID NO 164
<211> LENGTH: 11
<212> TYPE: PRT
<213> ORGANISM: Trichomonas vaginalis

<400> SEQUENCE: 164

Lys Leu Asn Tyr Lys Val Thr Tyr Thr Tyr Ser
1               5                   10
```

<210> SEQ ID NO 165
<211> LENGTH: 11
<212> TYPE: PRT
<213> ORGANISM: Trichomonas vaginalis

<400> SEQUENCE: 165

Tyr Lys Val Thr Tyr Thr Tyr Ser Asp Ala Thr
1               5                   10

<210> SEQ ID NO 166
<211> LENGTH: 15
<212> TYPE: PRT
<213> ORGANISM: Trichomonas vaginalis

<400> SEQUENCE: 166

Ala Glu His Asp Ala Ile Val Lys Glu Cys Ile Ala Glu Ala Ala
1               5                   10                  15

<210> SEQ ID NO 167
<211> LENGTH: 15
<212> TYPE: PRT
<213> ORGANISM: Trichomonas vaginalis

<400> SEQUENCE: 167

Thr Asp Gly Thr Val Leu Lys Lys Asn Ile Gly Gly Asn Ala Ser
1               5                   10                  15

<210> SEQ ID NO 168
<211> LENGTH: 16
<212> TYPE: PRT
<213> ORGANISM: Trichomonas vaginalis

<400> SEQUENCE: 168

Ile Leu Val Lys Lys Tyr Gly Leu Ser Ala Lys Asn Leu Asp Glu Phe
1               5                   10                  15

<210> SEQ ID NO 169
<211> LENGTH: 15
<212> TYPE: PRT
<213> ORGANISM: Trichomonas vaginalis

<400> SEQUENCE: 169

Ala Ser Ser Glu Phe Tyr Asp Glu Glu Lys Lys Leu Tyr Glu Val
1               5                   10                  15

<210> SEQ ID NO 170
<211> LENGTH: 16
<212> TYPE: PRT
<213> ORGANISM: Trichomonas vaginalis

<400> SEQUENCE: 170

Asp Tyr Glu Asn Trp Thr Lys Leu Asn Ala Arg Leu Gly Gln Arg Val
1               5                   10                  15

<210> SEQ ID NO 171
<211> LENGTH: 15
<212> TYPE: PRT
<213> ORGANISM: Trichomonas vaginalis

<400> SEQUENCE: 171

Arg Ala Ser Arg Lys Leu Tyr Pro Lys Asp Ile Gln Val Val Ala
1               5                   10                  15

-continued

```
<210> SEQ ID NO 172
<211> LENGTH: 15
<212> TYPE: PRT
<213> ORGANISM: Trichomonas vaginalis

<400> SEQUENCE: 172

Asn Val Tyr Leu Leu Lys Tyr Asp Thr Ala His Arg Ala Phe Pro
1               5                   10                  15

<210> SEQ ID NO 173
<211> LENGTH: 15
<212> TYPE: PRT
<213> ORGANISM: Trichomonas vaginalis

<400> SEQUENCE: 173

Val Val Leu Glu Ser Thr Gly Ile Phe Arg Thr Lys Ala Glu Lys
1               5                   10                  15

<210> SEQ ID NO 174
<211> LENGTH: 16
<212> TYPE: PRT
<213> ORGANISM: Trichomonas vaginalis

<400> SEQUENCE: 174

Thr Leu Asn Asn Ala Phe Gly Ile Arg Asn Gly Phe Met Thr Thr Val
1               5                   10                  15

<210> SEQ ID NO 175
<211> LENGTH: 316
<212> TYPE: PRT
<213> ORGANISM: Artificial Sequence
<220> FEATURE:
<223> OTHER INFORMATION: Synthetic SOE

<400> SEQUENCE: 175

Glu Glu His Thr Tyr Thr Arg Pro Glu Glu Val Gln Asp Phe Val Ser
1               5                   10                  15

Lys Glu Glu Leu Gly Gly Ala Arg Thr Lys Leu Thr Glu Met Tyr Met
            20                  25                  30

Arg Lys Glu Glu Ala Glu His Asp Ala Ile Val Lys Glu Cys Ile Ala
        35                  40                  45

Glu Ala Ala Glu Glu Val Lys Tyr Leu Gly Arg Val Thr Leu Ala Ala
    50                  55                  60

Arg Ser Ser Ala Glu Glu Val Thr Leu Ala Ala Arg Ser Ser Ala Pro
65                  70                  75                  80

Ser Gly Ala Ser Thr Glu Glu Thr Asp Gly Thr Val Leu Lys Lys Asn
                85                  90                  95

Ile Gly Gly Asn Ala Ser Glu Glu Asp Lys Val Pro Lys Lys Phe Lys
            100                 105                 110

Leu Pro Ser Pro Phe Phe Asn Glu Glu Lys Leu Gly Gly Leu Leu Val
        115                 120                 125

Lys Lys Tyr Gly Leu Ser Ala Lys Glu Glu Ile Leu Val Lys Lys Tyr
    130                 135                 140

Gly Leu Ser Ala Lys Asn Leu Asp Glu Phe Glu Glu Ala Ser Ser Glu
145                 150                 155                 160

Phe Tyr Asp Glu Glu Lys Lys Leu Tyr Glu Val Glu Glu Asp Tyr Glu
                165                 170                 175

Asn Trp Thr Lys Leu Asn Ala Arg Leu Gly Gln Arg Val Glu Glu Arg
            180                 185                 190

Ala Ser Arg Lys Leu Tyr Pro Lys Asp Ile Gln Val Val Ala Glu Glu
```

```
            195                 200                 205
Asn Val Tyr Leu Leu Lys Tyr Asp Thr Ala His Arg Ala Phe Pro Glu
    210                 215                 220

Glu Gln Glu Phe Thr Val Gly Glu Gly Ala Asp Lys Trp Val Val Lys
225                 230                 235                 240

Glu Glu Trp Val Val Lys Ser Ile Gly Gly Arg Leu Gly Pro Ser Gln
                    245                 250                 255

Leu Glu Glu Val Val Leu Glu Ser Thr Gly Ile Phe Arg Thr Lys Ala
                260                 265                 270

Glu Lys Glu Glu Lys Asp Ala Glu Gly Lys Ile Lys Lys Asp Asp Gly
            275                 280                 285

Tyr Asp Gly His Glu Glu Thr Leu Asn Asn Ala Phe Gly Ile Arg Asn
    290                 295                 300

Gly Phe Met Thr Thr Val His His His His His
305                 310                 315

<210> SEQ ID NO 176
<211> LENGTH: 189
<212> TYPE: PRT
<213> ORGANISM: Homo sapiens

<400> SEQUENCE: 176

Met Ile Phe Cys Ser Thr Cys Asn Asn Thr Gln Arg Thr Ala Leu Leu
1               5                   10                  15

Leu Arg Asn Leu Gly Phe Thr Ala Ile Pro Leu His Gly Gln Met Ser
                20                  25                  30

Gln Ser Lys Arg Leu Gly Ser Leu Asn Lys Phe Lys Ala Lys Ala Arg
            35                  40                  45

Ser Ile Leu Leu Ala Thr Asp Val Ala Ser Arg Gly Leu Asp Ile Pro
        50                  55                  60

His Val Asp Val Val Asn Phe Asp Ile Pro Thr His Ser Lys Asp
65                  70                  75                  80

Tyr Ile His Arg Val Gly Arg Thr Ala Arg Ala Gly Arg Ser Gly Lys
                85                  90                  95

Ala Ile Thr Phe Val Thr Gln Tyr Asp Val Glu Leu Phe Gln Arg Ile
            100                 105                 110

Glu His Leu Ile Gly Lys Lys Leu Pro Gly Phe Pro Thr Gln Asp Asp
        115                 120                 125

Glu Val Met Met Leu Thr Glu Arg Val Ala Glu Ala Gln Arg Phe Ala
130                 135                 140

Arg Met Glu Leu Arg Glu His Gly Glu Lys Lys Lys Arg Ser Arg Glu
145                 150                 155                 160

Asp Ala Gly Asp Asn Asp Asp Thr Glu Gly Ala Ile Gly Val Arg Asn
                165                 170                 175

Lys Val Ala Gly Gly Lys Met Lys Lys Arg Lys Gly Arg
            180                 185

<210> SEQ ID NO 177
<211> LENGTH: 351
<212> TYPE: PRT
<213> ORGANISM: Trichomonas suis

<400> SEQUENCE: 177

Val Lys Asp Arg Asn Asp Glu Gln Arg Arg Ala Arg Phe Glu Lys Tyr
1               5                   10                  15

Tyr Ser Gln Leu Asp Lys Asp Gly Ser Gly His Leu Asn Tyr Glu Glu
```

```
            20                  25                  30
Phe Lys Lys Phe Leu Val Thr Tyr Asn Lys Lys Glu Met Pro Glu Lys
             35                  40                  45

Gln Tyr Glu Phe Phe Phe Arg Gly Ala Asp Ile Asp Ala Gly Gly Ser
     50                  55                  60

Ile Gly Lys Glu Glu Leu Leu Phe Thr Leu Val Glu Ala Leu Tyr Lys
 65                  70                  75                  80

Asn Asp Gln Leu Tyr Ile Asn Lys Leu Phe Phe Arg Ala Val Asp Lys
                 85                  90                  95

Asp Arg Ser Arg Glu Ile Glu Ala Asp Glu Phe Val Val Met Ala Glu
            100                 105                 110

Leu Asn Gly Arg Glu Met Ser Lys Glu Asp Ala Ala Ala Gln Ile Glu
        115                 120                 125

Arg Leu Thr Gly Gly Lys Lys Thr Leu Thr Phe Pro Gln Met His Lys
    130                 135                 140

Ala Leu Thr Gly Gly Glu Val Pro Glu Asp Thr Asp Pro Tyr Asp Gly
145                 150                 155                 160

Lys Leu Asp Gly Gly Val Gln Thr Arg Gly Val Pro Glu Pro Lys Pro
                165                 170                 175

Leu Gly Ile Ala Ser Ser Glu Ala Glu Lys Glu Gly Ile Lys Thr Leu
            180                 185                 190

Ile Ser Lys Phe Asp Lys Ser Gly Asn Gly Lys Leu Glu Phe Asp Glu
        195                 200                 205

Phe Leu Gly Phe Met Lys Val Asn Leu Glu Asn Pro Glu Gln Glu Val
    210                 215                 220

Glu Ala Lys Asp Leu Asn Leu Lys Lys Cys Ala Ser Tyr Thr Thr Asp
225                 230                 235                 240

Leu Asp Gly Ser His Asn Leu Asp Ala Ser Glu Ile Ile Glu Cys Leu
                245                 250                 255

Ser Ala Trp Lys Thr Gly Asp Phe Lys Trp Ile Thr Lys Met Ile Phe
            260                 265                 270

Arg Gly Ala Asp Lys Asp Asn Ser Arg Lys Val Ser Val Ala Glu Met
        275                 280                 285

Lys Asp Ala Val Gln Asn Val Met Gly Lys Thr Phe Thr Pro Glu Glu
    290                 295                 300

Phe Thr Ala Gln Cys Lys Leu Glu Phe Gly Ala Asn Lys Lys Glu Leu
305                 310                 315                 320

Glu Phe Trp Glu Phe Tyr Lys Leu Ile Thr Gly Glu Thr Ile Asp Lys
                325                 330                 335

Ala Thr Asp Pro Tyr Asp Gly Lys Leu Pro Ala Glu Lys Ser Lys
            340                 345                 350

<210> SEQ ID NO 178
<211> LENGTH: 564
<212> TYPE: PRT
<213> ORGANISM: Candida albicans

<400> SEQUENCE: 178

Met Phe Gln Lys Gln Lys Val Ser Pro Trp Glu Tyr Leu Gln Glu Ala
1               5                  10                  15

Thr Leu Val Lys Trp Val Asn Thr Lys Leu Ile Glu Asp Thr Leu Ser
            20                  25                  30

Pro Gln Thr Pro Thr Ser Ser Cys Lys Asn Ile Ser Glu Thr Ile Asn
        35                  40                  45
```

```
Asn Leu Thr Ser Asp Leu His Asp Ser Leu Val Leu Thr Lys Leu Val
 50                  55                  60

Asn Arg Leu Ile Tyr Glu Val Thr Leu Asn Pro Asp His Pro Met Asn
 65                  70                  75                  80

Lys Lys Ala Asn Leu Tyr Tyr Leu Thr Pro Ile Tyr Thr Lys Pro Thr
                 85                  90                  95

Phe Lys Leu Gln Lys Leu Glu Asn Leu Ser Asp Leu Leu Lys Phe Leu
                100                 105                 110

Asn Leu Ile Leu Ser Ile Asn Val Ser Ser Ile Ser Pro Glu Asn Ile
            115                 120                 125

Phe Asp Gly Asp Leu Lys Leu Thr Leu Gly Leu Val Trp Ser Leu Phe
130                 135                 140

Ile Phe Asn Thr Ala Ser Val Phe Pro Gly Thr Pro Thr Tyr Ser Gly
145                 150                 155                 160

Ile Lys Thr Ile Leu Leu Lys Trp Ile Asn Gly Ile Leu Thr Asp Thr
                165                 170                 175

Ser Ile Arg Asn Phe Ser Lys Asp Trp Ala Asn Glu Pro Glu Thr Ile
            180                 185                 190

Leu Cys Glu Ile Ile Ser Asn Tyr Asp Ala Asn Ile Pro Cys Gly Met
        195                 200                 205

Asn Leu Ser Glu Leu Leu Asp Tyr Leu Glu Glu Ser Ile Ala Phe Pro
210                 215                 220

Lys Leu Ile Glu Pro Asp Asp Phe Gln Tyr Asn Asp Glu Lys Cys Leu
225                 230                 235                 240

Ile Val Phe Leu Val Glu Leu Tyr Lys Ile Phe Glu Ile Glu Lys Ser
                245                 250                 255

Tyr Asn Asn Val Ala Val Asp Asn Ser Leu Gly Phe Asp Gln Val Ile
            260                 265                 270

Thr Ala Thr Val Glu Ile Phe Lys Leu Lys Ser Lys Tyr Glu Ser Glu
        275                 280                 285

Ala Leu Lys Leu Ser Asn Gln Leu Asn Thr Leu Ile Asn Gln Leu Ser
290                 295                 300

Leu Asp Ile Ser Asp Leu Lys Asn Asp Phe Thr Met Asp Ile Leu Ser
305                 310                 315                 320

Cys Leu Lys Leu Leu Glu Asp Ser Ile Leu Asp Ser Thr Lys Leu Thr
                325                 330                 335

Pro Phe Gln Asn Ser Phe Asn His Leu Asn Val Lys Leu Thr Ser Leu
            340                 345                 350

Val Asn Ile Leu Gln Arg Phe Gln Asn Phe Arg Phe Glu Ile Lys Ser
        355                 360                 365

Glu Leu Val Tyr Gln Ser Tyr Pro Gln Ile Ile Gln Ile Leu Gly Ser
370                 375                 380

Ile Lys Ser Met Leu Gln Ser Phe Gly Asp Ile Asp Tyr Ile Pro Ala
385                 390                 395                 400

Ser Lys Thr Leu Asn Ile Asp Pro Ile Ser Thr Lys Leu Glu Gln Leu
                405                 410                 415

Ile Thr Leu Asp Ser Leu Ile Leu Ala Glu Ile Ser Glu Val Ile Leu
            420                 425                 430

Asn Thr Asn Ser Glu Glu Leu Phe Ile Lys Leu Ser Lys Leu Lys Asp
        435                 440                 445

Val Lys Thr Lys His Lys Ser Val Lys Thr Glu Cys Glu Thr Thr Ile
450                 455                 460

Glu Tyr Phe Leu Gly Phe Phe Arg Lys Leu Glu Met Phe Glu Ser Ser
```

```
                465                 470                 475                 480
Leu Gln Ser Ser Pro Pro Leu Lys Tyr Phe Glu Ala Arg Asp Pro Pro
                    485                 490                 495

Asp Phe Asp Ile Thr Pro Asp Ile Phe Asn Gln Phe Lys Thr Val Ile
                500                 505                 510

Leu Arg His Asn Asn Cys His His Asp Lys Phe Arg Val Leu Gln Glu
                515                 520                 525

Gln Phe Val Pro Ser Asp Phe Ser Asn Thr Thr Leu Glu Phe Phe Thr
            530                 535                 540

Arg Leu Ile Pro Ile Lys Ala Ser Pro Ile Ser Ser Asn Asp Ser Ser
545                 550                 555                 560

Phe Asp Leu Thr

<210> SEQ ID NO 179
<211> LENGTH: 599
<212> TYPE: PRT
<213> ORGANISM: Saccharomyces cerevisiae

<400> SEQUENCE: 179

Met Asn Ile Val Lys Leu Gln Val Arg Lys Phe Pro Ile Leu Thr Gln
1               5                   10                  15

Glu Asp Leu Phe Ser Thr Ile Glu Lys Phe Arg Ala Ile Asp Leu Asp
                20                  25                  30

Asp Lys Gly Trp Val Glu Lys Gln Ala Leu Glu Ala Val Ser Lys
            35                  40                  45

Asp Gly Asp Ala Thr Tyr Asp Glu Ala Arg Glu Thr Leu Lys His Val
        50                  55                  60

Gly Val Asp Ala Ser Gly Arg Val Glu Leu Asp Asp Tyr Val Gly Leu
65                  70                  75                  80

Val Ala Lys Leu Arg Glu Ser Lys Thr Gly Ala Ala Pro Gln Thr Thr
                85                  90                  95

Phe Asn Val Ala Pro Asn Ser Thr Pro Ile Val Ser Thr Ala Ala Thr
            100                 105                 110

Gly Leu Gln His Lys Gly Lys Gly Thr Gln Ala Lys Ile Ile Val Ala
        115                 120                 125

Gly Ser Gln Thr Gly Thr Thr His Thr Ile Asn Glu Glu Arg Arg
    130                 135                 140

Glu Phe Thr Lys His Ile Asn Ser Val Leu Ala Gly Asp Gln Asp Ile
145                 150                 155                 160

Gly Asp Leu Leu Pro Phe Pro Thr Asp Thr Phe Gln Leu Phe Asp Glu
                165                 170                 175

Cys Arg Asp Gly Leu Val Leu Ser Lys Leu Ile Asn Asp Ser Val Pro
            180                 185                 190

Asp Thr Ile Asp Asp Thr Arg Val Leu Asn Trp Pro Lys Lys Gly Lys
        195                 200                 205

Glu Leu Asn Asn Phe Gln Ala Ser Glu Asn Ala Asn Ile Val Ile Asn
    210                 215                 220

Ser Ala Lys Ala Ile Gly Cys Val Val Asn Val His Ser Glu Asp
225                 230                 235                 240

Ile Ile Glu Gly Arg Glu His Leu Ile Leu Gly Leu Ile Trp Gln Ile
                245                 250                 255

Ile Arg Arg Gly Leu Leu Ser Lys Ile Asp Ile Lys Leu His Pro Glu
            260                 265                 270

Leu Tyr Arg Leu Leu Glu Asp Asp Glu Thr Leu Glu Gln Phe Leu Arg
```

```
                     275                 280                 285
Leu Pro Pro Glu Gln Ile Leu Leu Arg Trp Phe Asn Tyr His Leu Lys
    290                 295                 300

Gln Ala Asn Trp Asn Arg Arg Val Thr Asn Phe Ser Lys Asp Val Ser
305             310                 315                     320

Asp Gly Glu Asn Tyr Thr Ile Leu Leu Asn Gln Leu Asp Pro Ala Leu
                325                 330                 335

Cys Ser Lys Ala Pro Leu Gln Thr Thr Asp Leu Met Glu Arg Ala Glu
            340             345                 350

Gln Val Leu Gln Asn Ala Glu Lys Leu Asp Cys Arg Lys Tyr Leu Thr
        355                 360             365

Pro Ser Ser Leu Val Ala Gly Asn Pro Lys Leu Asn Leu Ala Phe Val
    370             375             380

Ala His Leu Phe Asn Thr His Pro Gly Leu Glu Pro Ile Gln Glu Glu
385             390                 395                     400

Glu Lys Pro Glu Ile Glu Glu Phe Asp Ala Glu Gly Glu Arg Glu Ala
                405             410              415

Arg Val Phe Thr Leu Trp Leu Asn Ser Leu Asp Val Asp Pro Pro Val
            420             425             430

Ile Ser Leu Phe Asp Asp Leu Lys Asp Gly Leu Ile Leu Leu Gln Ala
        435             440             445

Tyr Glu Lys Val Met Pro Gly Ala Val Asp Phe Lys His Val Asn Lys
    450             455             460

Arg Pro Ala Ser Gly Ala Glu Ile Ser Arg Phe Lys Ala Leu Glu Asn
465             470             475                     480

Thr Asn Tyr Ala Val Asp Leu Gly Arg Ala Lys Gly Phe Ser Leu Val
            485             490             495

Gly Ile Glu Gly Ser Asp Ile Val Asp Gly Asn Lys Leu Leu Leu Gly
            500             505             510

Leu Val Trp Gln Leu Met Arg Arg Asn Ile Ser Ile Thr Met Lys Thr
        515             520             525

Leu Ser Ser Ser Gly Arg Asp Met Ser Asp Ser Gln Ile Leu Lys Trp
    530             535             540

Ala Gln Asp Gln Val Thr Lys Gly Gly Lys Asn Ser Thr Ile Arg Ser
545             550             555                     560

Phe Lys Asp Gln Ala Leu Ser Asn Ala His Phe Leu Leu Asp Val Leu
            565             570             575

Asn Gly Ile Ala Pro Gly Tyr Val Asp Tyr Asp Leu Val Thr Pro Gly
            580             585             590

Asn Thr Glu Glu Glu Arg Tyr
            595
```